US011033731B2

(12) United States Patent
Jeffery et al.

(10) Patent No.: US 11,033,731 B2
(45) Date of Patent: Jun. 15, 2021

(54) METHODS AND APPARATUSES FOR TRANSDERMAL ELECTRICAL STIMULATION

(71) Applicant: Thync Global, Inc., Los Gatos, CA (US)

(72) Inventors: Douglas Jeffery, San Jose, CA (US); Wing Law, Cupertino, CA (US); Jay Frederick Hamlin, Santa Cruz, CA (US); Remi Demers, Saint-Nicolas, CA (US); Rafal Piersiak, Los Gatos, CA (US)

(73) Assignee: Thync Global, Inc., Los Gatos, CA (US)

( * ) Notice: Subject to any disclaimer, the term of this patent is extended or adjusted under 35 U.S.C. 154(b) by 312 days.

(21) Appl. No.: 15/169,445

(22) Filed: May 31, 2016

(65) Prior Publication Data

US 2016/0346530 A1 Dec. 1, 2016

Related U.S. Application Data

(60) Provisional application No. 62/213,949, filed on Sep. 3, 2015, provisional application No. 62/200,256, filed
(Continued)

(51) Int. Cl.
*A61N 1/04* (2006.01)
*A61N 1/36* (2006.01)
(Continued)

(52) U.S. Cl.
CPC ........... *A61N 1/0492* (2013.01); *A61M 21/02* (2013.01); *A61N 1/048* (2013.01); *A61N 1/0456* (2013.01);
(Continued)

(58) Field of Classification Search
CPC ............................ A61N 1/0492; A61N 1/0456
See application file for complete search history.

(56) References Cited

U.S. PATENT DOCUMENTS 3,255,753 A 6/1966 Wing
3,388,699 A 1/1968 Webb et al.
(Continued)

FOREIGN PATENT DOCUMENTS

CN 1204268 A 1/1999
CN 1607970 A 4/2005
(Continued)

OTHER PUBLICATIONS

Axelgaard Manufacturing Co. Ltd.; Little Pals® (product information); 2 pgs.; printed Feb. 11, 2013 from http://www.axelgaard.com/prod_little-pals.html.
(Continued)

*Primary Examiner* — Rex R Holmes
*Assistant Examiner* — Jennifer L Ghand
(74) *Attorney, Agent, or Firm* — Shay Glenn LLP

(57) ABSTRACT

Methods and apparatuses for transdermal electrical stimulation. Described herein are single-use or limited-use TES apparatuses and methods of using them that include an integrated (e.g., flex-circuit) electrode assembly and controller apparatus including a waveform generator and power supply. Also described herein are TES apparatuses including a cord or wire having current control circuitry and configured to connect a mobile computing device (e.g., smartphone or wearable electronics) to an electrode assembly. Finally, also described herein are intermediate apparatuses including a flex-circuit electrode assembly including a waveform generator but receiving power from a cable connected to a mobile computing device.

36 Claims, 39 Drawing Sheets

Related U.S. Application Data on Aug. 3, 2015, provisional application No. 62/190,211, filed on Jul. 8, 2015, provisional application No. 62/168,615, filed on May 29, 2015.

(51) Int. Cl.
  *A61M 21/02* (2006.01)
  *A61N 1/05* (2006.01)
  *A61M 21/00* (2006.01)
  *A61M 16/06* (2006.01)

(52) U.S. Cl.
  CPC ..... *A61N 1/36025* (2013.01); *A61N 1/36031* (2017.08); *A61N 1/36034* (2017.08); *A61M 16/0688* (2014.02); *A61M 2021/0072* (2013.01); *A61M 2205/3306* (2013.01); *A61M 2205/3324* (2013.01); *A61M 2205/3375* (2013.01); *A61M 2210/0687* (2013.01); *A61M 2230/10* (2013.01); *A61M 2230/63* (2013.01); *A61N 1/0488* (2013.01); *A61N 1/0526* (2013.01)

(56) References Cited

U.S. PATENT DOCUMENTS

| | | |
|---|---|---|
| 3,620,219 A | 11/1971 | Barker |
| 3,648,708 A | 3/1972 | Haeri |
| 3,762,396 A | 10/1973 | Ballentine et al. |
| 4,418,687 A | 12/1983 | Matsumoto et al. |
| 4,431,000 A | 2/1984 | Butler et al. |
| 4,646,744 A | 3/1987 | Capel |
| 4,664,117 A | 5/1987 | Beck |
| 4,865,048 A | 9/1989 | Eckerson |
| 5,144,952 A | 9/1992 | Frachet et al. |
| 5,183,041 A | 2/1993 | Toriu et al. |
| 5,335,657 A | 8/1994 | Terry et al. |
| 5,342,410 A | 8/1994 | Braverman |
| 5,397,338 A | 3/1995 | Grey et al. |
| 5,476,481 A | 12/1995 | Schondorf |
| 5,487,759 A | 1/1996 | Bastyr et al. |
| 5,514,175 A | 5/1996 | Kim et al. |
| 5,540,736 A | 7/1996 | Haimovich et al. |
| 5,573,552 A | 11/1996 | Hansjurgens |
| 5,578,065 A | 11/1996 | Hattori et al. |
| 5,593,427 A | 1/1997 | Gliner et al. |
| 5,738,647 A | 4/1998 | Bernhard et al. |
| 5,792,067 A | 8/1998 | Karell |
| 6,066,163 A | 5/2000 | John |
| 6,280,454 B1 | 8/2001 | Wang |
| 6,324,432 B1 | 11/2001 | Rigaux et al. |
| 6,445,955 B1 | 9/2002 | Michelson et al. |
| 6,463,328 B1 | 10/2002 | John |
| 6,516,227 B1 | 2/2003 | Meadows et al. |
| 6,526,318 B1 | 2/2003 | Ansarinia |
| 6,567,702 B1 | 5/2003 | Nekhendzy et al. |
| 6,731,987 B1 | 5/2004 | McAdams et al. |
| 6,983,184 B2 | 1/2006 | Price |
| 7,120,499 B2 | 10/2006 | Thrope et al. |
| 7,146,217 B2 | 12/2006 | Firlik et al. |
| 7,263,501 B2 | 8/2007 | Tirinato et al. |
| 7,376,467 B2 | 5/2008 | Thrope et al. |
| 7,422,555 B2 | 9/2008 | Zabara |
| 7,577,481 B2 | 8/2009 | Firlik et al. |
| 7,660,636 B2 | 2/2010 | Castel et al. |
| 7,801,600 B1 | 9/2010 | Carbunaru et al. |
| 7,891,615 B2 | 2/2011 | Bevirt |
| 7,949,403 B2 | 5/2011 | Palermo et al. |
| 8,029,431 B2 | 10/2011 | Tononi |
| 8,034,294 B1 | 10/2011 | Goldberg |
| 8,086,318 B2 | 12/2011 | Strother et al. |
| 8,097,926 B2 | 1/2012 | De Graff et al. |
| 8,116,875 B2 | 2/2012 | Osypka et al. |
| 8,121,695 B2 | 2/2012 | Gliner et al. |
| 8,150,537 B2 | 4/2012 | Tanaka et al. |
| 8,190,248 B2 | 5/2012 | Besio et al. |
| 8,197,276 B2 | 6/2012 | Egloff et al. |
| 8,204,601 B2 | 6/2012 | Moyer et al. |
| 8,239,030 B1 | 8/2012 | Hagedorn et al. |
| 8,265,761 B2 | 9/2012 | Siever |
| 8,280,502 B2 | 10/2012 | Hargrove et al. |
| 8,346,337 B2 | 1/2013 | Heller et al. |
| 8,380,315 B2 | 2/2013 | DeGiorgio et al. |
| 8,428,738 B2 | 4/2013 | Valencia |
| 8,463,383 B2 | 6/2013 | Sakai et al. |
| 8,494,625 B2 | 7/2013 | Hargrove |
| 8,494,627 B2 | 7/2013 | Bikson et al. |
| 8,506,469 B2 | 8/2013 | Dietrich et al. |
| 8,532,758 B2 | 9/2013 | Silverstone |
| 8,560,075 B2 | 10/2013 | Covalin |
| 8,571,651 B2 | 10/2013 | Ben-Ezra et al. |
| 8,583,238 B1 | 11/2013 | Heldman et al. |
| 8,583,256 B2 | 11/2013 | Tracey et al. |
| 8,612,005 B2 | 12/2013 | Rezai et al. |
| 8,639,343 B2 | 1/2014 | De Vos |
| 8,660,644 B2 | 2/2014 | Jaax et al. |
| 8,688,239 B2 | 4/2014 | Hartlep et al. |
| 8,843,210 B2 | 9/2014 | Simon et al. |
| 8,874,219 B2 | 10/2014 | Trier et al. |
| 8,903,494 B2 | 12/2014 | Goldwasser et al. |
| 8,983,621 B2 | 3/2015 | Hou et al. |
| 9,002,458 B2 | 4/2015 | Pal et al. |
| 9,014,811 B2 | 4/2015 | Pal et al. |
| 9,067,054 B2 | 6/2015 | Simon et al. |
| 9,168,374 B2 | 10/2015 | Su |
| 9,205,258 B2 | 12/2015 | Simon et al. |
| 9,233,244 B2 | 1/2016 | Pal et al. |
| 9,248,292 B2 | 2/2016 | Trier et al. |
| 9,333,334 B2 | 5/2016 | Jeffery et al. |
| 9,364,674 B2 | 6/2016 | Cook et al. |
| 9,393,401 B2 | 7/2016 | Goldwasser et al. |
| 9,393,430 B2 | 7/2016 | Demers et al. |
| 9,415,219 B2 | 8/2016 | Simon et al. |
| 9,446,242 B2 | 9/2016 | Griffith |
| 9,474,905 B2 | 10/2016 | Doan et al. |
| 9,655,772 B2 | 5/2017 | Smith et al. |
| 9,656,076 B2 | 5/2017 | Trier et al. |
| 9,700,725 B2 | 7/2017 | Zhu |
| 9,731,116 B2 | 8/2017 | Chen |
| 9,744,347 B2 | 8/2017 | Chen et al. |
| 9,764,133 B2 | 9/2017 | Thomas et al. |
| 9,782,587 B2 | 10/2017 | Trier et al. |
| 2001/0000187 A1 | 4/2001 | Peckham et al. |
| 2002/0116036 A1 | 8/2002 | Daignault et al. |
| 2003/0088279 A1 | 5/2003 | Rissmann et al. |
| 2003/0134545 A1 | 7/2003 | McAdams et al. |
| 2003/0171685 A1 | 9/2003 | Lesser et al. |
| 2003/0225323 A1 | 12/2003 | Kiani et al. |
| 2004/0019370 A1 | 1/2004 | Gliner et al. |
| 2004/0098065 A1 | 5/2004 | Hagglof et al. |
| 2004/0158305 A1 | 8/2004 | Axelgaard |
| 2004/0267333 A1 | 12/2004 | Kronberg |
| 2005/0165460 A1 | 7/2005 | Erfan |
| 2005/0267388 A1 | 12/2005 | Hanna |
| 2005/0283259 A1 | 12/2005 | Wolpow |
| 2006/0047215 A1 | 3/2006 | Newman et al. |
| 2006/0064139 A1 | 3/2006 | Chung et al. |
| 2006/0149119 A1 | 7/2006 | Wang |
| 2006/0190057 A1 | 8/2006 | Reese |
| 2006/0195159 A1 | 8/2006 | Bradley et al. |
| 2006/0206163 A1 | 9/2006 | Wahlstrand et al. |
| 2006/0247985 A1 | 11/2006 | Liamos et al. |
| 2007/0053466 A1 | 3/2007 | Klostermann |
| 2007/0088419 A1 | 4/2007 | Fiorina et al. |
| 2007/0097593 A1 | 5/2007 | Armstrong |
| 2007/0100275 A1 | 5/2007 | Fischer et al. |
| 2007/0173890 A1 | 7/2007 | Armstrong |
| 2007/0213790 A1 | 9/2007 | Nolan et al. |
| 2007/0276451 A1 | 11/2007 | Rigaux |
| 2008/0015641 A1 | 1/2008 | Armstrong et al. |
| 2008/0045882 A1 | 2/2008 | Finsterwald |
| 2008/0071626 A1 | 3/2008 | Hill |
| 2008/0097564 A1 | 4/2008 | Lathrop |
| 2008/0132974 A1 | 6/2008 | Strother et al. |

(56) References Cited

U.S. PATENT DOCUMENTS

| | | |
|---|---|---|
| 2008/0207985 A1 | 8/2008 | Farone |
| 2008/0208266 A1 | 8/2008 | Lesser et al. |
| 2008/0215113 A1 | 9/2008 | Pawlowicz |
| 2008/0275293 A1 | 11/2008 | Lattner et al. |
| 2008/0281368 A1 | 11/2008 | Bulkes et al. |
| 2008/0319505 A1 | 12/2008 | Boyden et al. |
| 2009/0048642 A1 | 2/2009 | Goroszeniuk |
| 2009/0054952 A1 | 2/2009 | Glukhovsky et al. |
| 2009/0076559 A1 | 3/2009 | Libbos et al. |
| 2009/0099623 A1 | 4/2009 | Bentwich |
| 2009/0112280 A1 | 4/2009 | Wingeier et al. |
| 2009/0177243 A1 | 7/2009 | Lebedev et al. |
| 2009/0210028 A1 | 8/2009 | Rigaux et al. |
| 2009/0240303 A1 | 9/2009 | Wahlstrand et al. |
| 2009/0270947 A1 | 10/2009 | Stone et al. |
| 2009/0287108 A1 | 11/2009 | Levy |
| 2010/0042180 A1* | 2/2010 | Mueller .............. A61N 1/0456 607/46 |
| 2010/0057154 A1 | 3/2010 | Dietrich et al. |
| 2010/0076533 A1 | 3/2010 | Dar et al. |
| 2010/0094375 A1 | 4/2010 | Donders et al. |
| 2010/0145399 A1 | 6/2010 | Johari et al. |
| 2010/0145428 A1 | 6/2010 | Cameron et al. |
| 2010/0152817 A1 | 6/2010 | Gillbe |
| 2010/0222734 A1 | 9/2010 | Jayes et al. |
| 2010/0256436 A1 | 10/2010 | Partsch et al. |
| 2010/0318168 A1 | 12/2010 | Bignetti |
| 2011/0029045 A1 | 2/2011 | Cevette et al. |
| 2011/0034756 A1 | 2/2011 | Hacking et al. |
| 2011/0077660 A1 | 3/2011 | Janik et al. |
| 2011/0082326 A1 | 4/2011 | Mishelevich et al. |
| 2011/0082515 A1 | 4/2011 | Libbus et al. |
| 2011/0093033 A1 | 4/2011 | Nekhendzy |
| 2011/0112394 A1 | 5/2011 | Mishelevich |
| 2011/0112590 A1 | 5/2011 | Wu et al. |
| 2011/0114191 A1 | 5/2011 | Wheater et al. |
| 2011/0137381 A1 | 6/2011 | Lee et al. |
| 2011/0144716 A1 | 6/2011 | Bikson et al. |
| 2011/0160811 A1 | 6/2011 | Walker |
| 2011/0172752 A1 | 7/2011 | Bingham et al. |
| 2011/0190846 A1 | 8/2011 | Ruffini et al. |
| 2011/0230701 A1 | 9/2011 | Simon et al. |
| 2011/0230702 A1 | 9/2011 | Honour |
| 2011/0230938 A1 | 9/2011 | Simon et al. |
| 2011/0270345 A1 | 11/2011 | Johnston et al. |
| 2011/0276112 A1 | 11/2011 | Simon et al. |
| 2011/0288610 A1 | 11/2011 | Brocke |
| 2011/0301683 A1 | 12/2011 | Axelgaard |
| 2011/0307029 A1 | 12/2011 | Hargrove |
| 2011/0319950 A1 | 12/2011 | Sullivan |
| 2012/0016431 A1 | 1/2012 | Paul et al. |
| 2012/0029591 A1 | 2/2012 | Simon et al. |
| 2012/0029601 A1 | 2/2012 | Simon et al. |
| 2012/0109251 A1 | 5/2012 | Lebedev et al. |
| 2012/0149973 A1 | 6/2012 | Holloway |
| 2012/0165759 A1 | 6/2012 | Rogers et al. |
| 2012/0182924 A1 | 7/2012 | Gaines et al. |
| 2012/0184801 A1 | 7/2012 | Simon et al. |
| 2012/0185020 A1 | 7/2012 | Simon et al. |
| 2012/0209340 A1 | 8/2012 | Escribano |
| 2012/0209346 A1 | 8/2012 | Bikson et al. |
| 2012/0245409 A1 | 9/2012 | Liang |
| 2012/0245653 A1 | 9/2012 | Bikson et al. |
| 2012/0296390 A1 | 11/2012 | Nakashima et al. |
| 2012/0302912 A1 | 11/2012 | Moffitt et al. |
| 2012/0306628 A1 | 12/2012 | Singhal |
| 2013/0035734 A1 | 2/2013 | Soler et al. |
| 2013/0041235 A1 | 2/2013 | Rogers et al. |
| 2013/0060304 A1 | 3/2013 | La Tendresse et al. |
| 2013/0066395 A1 | 3/2013 | Simon et al. |
| 2013/0079659 A1 | 3/2013 | Akhadov et al. |
| 2013/0096641 A1 | 4/2013 | Strother et al. |
| 2013/0131551 A1 | 5/2013 | Raghunathan et al. |
| 2013/0158627 A1 | 6/2013 | Gozani et al. |
| 2013/0184779 A1 | 7/2013 | Bikson et al. |
| 2013/0204315 A1 | 8/2013 | Wongsarnpigoon et al. |
| 2013/0226275 A1 | 8/2013 | Duncan |
| 2013/0253613 A1 | 9/2013 | Salahovic et al. |
| 2013/0267761 A1 | 10/2013 | Bentwich |
| 2013/0282095 A1 | 10/2013 | Mignolet et al. |
| 2013/0304175 A1 | 11/2013 | Voegele et al. |
| 2013/0318168 A1 | 11/2013 | Demain et al. |
| 2013/0325096 A1 | 12/2013 | Dupelle et al. |
| 2013/0333094 A1 | 12/2013 | Rogers et al. |
| 2014/0031895 A1 | 1/2014 | Rahimi et al. |
| 2014/0128939 A1 | 5/2014 | Embrey et al. |
| 2014/0128944 A1 | 5/2014 | Stern et al. |
| 2014/0163645 A1 | 6/2014 | Dinsmoor et al. |
| 2014/0182350 A1 | 7/2014 | Bhavaraju et al. |
| 2014/0186807 A1 | 7/2014 | Rastatter et al. |
| 2014/0222102 A1 | 8/2014 | Lemus et al. |
| 2014/0257449 A1 | 9/2014 | Helmer |
| 2014/0275933 A1 | 9/2014 | Meyer et al. |
| 2014/0277324 A1 | 9/2014 | DiUbaldi et al. |
| 2014/0309709 A1 | 10/2014 | Gozani et al. |
| 2014/0336728 A1 | 11/2014 | Franke et al. |
| 2014/0371814 A1 | 12/2014 | Spizzirri et al. |
| 2015/0066104 A1 | 3/2015 | Wingeier et al. |
| 2015/0088224 A1 | 3/2015 | Goldwasser et al. |
| 2015/0224310 A1 | 8/2015 | Sharma et al. |
| 2015/0230863 A1 | 8/2015 | Youngquist et al. |
| 2015/0238762 A1 | 8/2015 | Pal et al. |
| 2015/0257970 A1 | 9/2015 | Mucke et al. |
| 2015/0328461 A1 | 11/2015 | Charlesworth et al. |
| 2015/0335877 A1 | 11/2015 | Jeffery et al. |
| 2015/0335888 A1 | 11/2015 | Demers et al. |
| 2016/0008632 A1 | 1/2016 | Wetmore et al. |
| 2016/0074657 A1 | 3/2016 | Kwan et al. |
| 2016/0279435 A1 | 9/2016 | Hyde et al. |
| 2016/0317809 A1 | 11/2016 | Pal et al. |
| 2017/0076414 A1 | 3/2017 | Egnal et al. |
| 2017/0252562 A1 | 9/2017 | Goldwasser et al. |
| 2018/0036533 A1 | 2/2018 | Yoo et al. |
| 2019/0321636 A1 | 10/2019 | Law et al. |
| 2019/0336765 A1 | 11/2019 | Charlesworth et al. |

FOREIGN PATENT DOCUMENTS

| | | |
|---|---|---|
| CN | 1704131 A | 12/2005 |
| CN | 1842356 A | 10/2006 |
| CN | 101234233 A | 8/2008 |
| CN | 101244314 A | 8/2008 |
| CN | 201353374 Y | 12/2009 |
| CN | 102245253 A | 11/2011 |
| CN | 102725021 A | 10/2012 |
| CN | 102906752 A | 1/2013 |
| CN | 103517732 A | 1/2014 |
| EP | 502919 B1 | 11/1993 |
| EP | 801957 A1 | 10/1997 |
| EP | 09965358 A2 | 12/1999 |
| EP | 1529550 A1 | 5/2005 |
| EP | 1502623 B1 | 11/2007 |
| EP | 1551290 B1 | 8/2008 |
| EP | 2024018 A2 | 2/2009 |
| EP | 2314346 A1 | 4/2011 |
| EP | 1559369 B1 | 3/2012 |
| EP | 2069001 B1 | 2/2013 |
| JP | 49-061984 A | 6/1974 |
| JP | 5-31197 A | 2/1993 |
| JP | 06339531 A | 12/1994 |
| JP | 10-108913 A | 4/1998 |
| JP | 2001129100 A | 5/2001 |
| JP | 2001293097 A | 10/2001 |
| JP | 2002-306604 A | 10/2002 |
| JP | 2003-10230 A | 1/2003 |
| JP | 2006-192302 A | 7/2006 |
| JP | 3129187 U | 1/2007 |
| JP | 2007535372 A | 12/2007 |
| JP | 2009-85901 A | 4/2009 |
| JP | 2009513248 A | 4/2009 |
| JP | 2011-118293 A | 6/2011 |
| JP | 2011519654 A | 7/2011 |
| JP | 2013512076 A | 4/2013 |
| WO | WO92/06737 A1 | 4/1992 |

(56) References Cited

FOREIGN PATENT DOCUMENTS

| WO | WO93/17628 A1 | 9/1993 |
|---|---|---|
| WO | WO94/00188 A1 | 1/1994 |
| WO | WO94/00189 A1 | 1/1994 |
| WO | WO01/08071 A1 | 2/2001 |
| WO | WO01/78834 A1 | 10/2001 |
| WO | WO03/018120 A1 | 3/2003 |
| WO | WO03/105945 A2 | 12/2003 |
| WO | WO2005/110531 A1 | 11/2005 |
| WO | WO2006/113801 A2 | 10/2006 |
| WO | WO2006/138702 A2 | 12/2006 |
| WO | WO2008/155114 A1 | 12/2008 |
| WO | WO2009/089014 A1 | 7/2009 |
| WO | WO2009/137683 A2 | 11/2009 |
| WO | WO2009/147599 A1 | 12/2009 |
| WO | WO2010/047834 A1 | 4/2010 |
| WO | WO2010/067145 A1 | 6/2010 |
| WO | WO2010/120823 A2 | 10/2010 |
| WO | WO2011/044176 A1 | 4/2011 |
| WO | WO2011/147546 A1 | 12/2011 |
| WO | WO2012/082960 A2 | 6/2012 |
| WO | WO2012/089588 A1 | 7/2012 |
| WO | WO2012/116407 A1 | 9/2012 |
| WO | WO2012/129574 A2 | 9/2012 |
| WO | WO2012/150600 A2 | 11/2012 |
| WO | WO2012/156051 A1 | 11/2012 |
| WO | WO2012/156052 A2 | 11/2012 |
| WO | WO2013/071307 A1 | 5/2013 |
| WO | WO2013/192582 A1 | 12/2013 |
| WO | WO2014/107624 A1 | 7/2014 |
| WO | WO2014/195516 A1 | 12/2014 |
| WO | WO2015/036420 A1 | 3/2015 |
| WO | WO2015/061663 A1 | 4/2015 |
| WO | WO2015/143053 A1 | 9/2015 |
| WO | WO2015/183690 A1 | 12/2015 |
| WO | WO2017/201525 A1 | 11/2017 |

OTHER PUBLICATIONS

Axelgaard Manufacturing Co. Ltd.; Pals® Platinum Blue (product information); 2 pgs.; printed Feb. 11, 2013 from http://www.axelgaard.com/prod_pals-platinum-blue.html.
Chaieb et al.; Transcranial alternating current stimulation in the low kHz range increases motor cortex excitability; Restor Neurol Neurosci; 29(3); pp. 167-175; Mar. 2011.
Coutinho et al.; Musical emotions: predicting second-by-second subjective feelings of emotion from low-level psychoacoustic features and physiological measurements; Emotion; 11(4); pp. 921-937; Aug. 2011.
DaSilva et al.; Electrode positioning and montage in transcranial direct current stimulation; J Vis Exp; 51; e2744; 11 pgs.; May 2011.
Digitimer Ltd.; DS2 and DS3 Isolated Stimulator (product information); 2 pgs.; downloaded from http://www.digitimer.com/research/stimulators/index.htm on Feb. 10, 2014.
Electozyme; Company and Product Information; 3 pgs.; printed Feb. 11, 2014 from http://electrozyme.com/applications/.
Feurra et al.; Frequency specific modulation of human somatosensory cortex; Front Psychol; 2(13); 6 pgs.; Feb. 2011.
GoFlow; tDCS Kit; product information; 9 pgs..; printed Feb. 10, 2014 (http://flowstateengaged.com/).
Gracenote; Timeline-metadata-api; 3 pages; retrieved from the internet Jul. 7, 2015; (https://github.com/gracenote/timeline-metadata-api/blob/master/README.md).
Grindhouse Wetware; Thinking Cap; product information; 1 pg.; printed Feb. 10, 2014 (http://www.grindhousewetware.com/thinkingcap.html).
Kanai et al.; Frequency-dependent electrical stimulatioin of the visual cortex; Curr. Biol.; 18(23); pp. 1839-1843; Dec. 9, 2008.
Paulus, W.; Transcranial electrical stimulation (tES-tDCS; tRNS, tACS) methods; Neuropsychol Rehabil.; 21(5); pp. 602-617; Oct. 2011.

Prausnitz; The effects of electric current applied to skin: a review for transdermal drug delivery; Advanced Drug Delivery Reviews; vol. 18; pp. 395-425; Feb. 8, 1996.
Saiote et al.; High-frequency TRNS reduces Bold activity during visuomotor learning; PLOS one; 8(3); e59669; 8 pgs.; Mar. 2013.
Schutter et al.; Brain oscillations and frequency-dependent modulation of cortical excitability; Brain Stimulation; 4(2); pp. 97-103; Apr. 2011.
STD Pharmaceutical Products; Idrostar intophoresis machine (product and use information); 9 pgs.; Dec. 2011 (printed Feb. 11, 2014 from http://www.iontophoresis.info/instructions/).
Terney et al.; Increasing human brain excitability by transcranial high-frequency random noise stimulation; The Journal of Neuroscience; 28(52); pp. 14127-14155; Dec. 2008.
Turi et al.; Both the cutaneous sensation and phosphene perception are modulated in a frequency-specific manner during transcranial alternating current stimulation; Restor. Neurol. Neurosci.; 31(3); pp. 275-285; 2013 (year of pub. sufficiently earlier than effective US filing date and any foreign priority date).
Tyler et al.; U.S. Appl. No. 61/550,334 entitled "Improvement Of Direct Communication," filed Oct. 21, 2011.
Tyler et al.; U.S. Appl. No. 61/663,409 entitled "Device And Methods For Noninvasive Neuromodulation Using Targeted Transcranial Electrical Stimulation," filed Jun. 22, 2012.
Pal et al.; U.S. Appl. No. 15/170,878 entitled "Apparatuses and methods for neuromodulation," filed Jun. 1, 2016.
Goldwasser et al.; U.S. Appl. No. 15/967,576 entitled "Transdermal electrical stimulation at the neck," filed Apr. 30, 2018.
Aston-Jones et al.; An integrative theory of locus coeruleus-norepinephrine function: adaptive gain and optimal performance; Annu. Rev. Neurosci.; 28: pp. 403-450; Jul. 21, 2005.
Aston-Jones et al.; Role of locus coeruleus in attention and behavioral flexibility; Biological Psychiatry; 46(9); pp. 1309-1320; Nov. 1, 1999.
Backhaus et al.; Sleep disturbances are correlated with decreased morning awakening salivary cortisol; Psychoneuroendocrinology; 29(9): pp. 1184-1191; Oct. 31, 2004.
Basta et al.; Chronic Insomnia and the Stress System; Sleep Medicine Clinics; 2(2): pp. 279-291; (Author Manuscript, 20 pages); Jun. 30, 2007.
Berlad et al.; Power spectrum analysis and heart rate variability in Stage 4 and REM sleep: evidence for state-specific changes in autonomic dominance; Journal of Sleep Research; 2(2): pp. 88-90; Jun. 1, 1993.
Berridge et al.; The locus coeruleus-noradrenergic system: modulation of behavioral state and state-dependent cognitive processes; Brain Research Reviews; 42(1); pp. 33-84; Apr. 30, 2003.
Brown et al.; Control of sleep and wakefulness; Physiological reviews; 92(3); pp. 1087-1187; Jul. 1, 2012.
Brown et al.;Locus ceruleus activation suppresses feedforward interneurons and reduces beta-gamma electroencephalogram frequencies while it enhances theta frequencies in rat dentate gyrus; Journals of Neuroscience; 25(8): pp. 1985-1991; Feb. 23, 2005.
Buchanan et al.; Salivary alpha-amylase levels as a biomarker of experienced fear; Communicative and Integrative Biology; 3(6); pp. 525-527; Nov. 1, 2010.
Buckley et al.; On the Interactions of the Hypothalamic-Pituitary-Adrenal (HPA) Axis and Sleep: Normal HPA Axis Activity and Circadian Rhythm, Exemplary Sleep Disorders; The Journal of Clinical Endocrinology and Metabolism; 90(5); pp. 3106-3114; May 1, 2005.
Buysse et al.; The Pittsburgh Sleep Quality Index: a new instrument for psychiatric practice and research; Psychiatric Research; 28(2); pp. 193-213; May 31, 1989.
Carter et al.; Tuning arousal with optogenetic modulation of locus coeruleus neurons; Nature Neuroscience; 13(12); pp. 1526-1533; Dec. 1, 2010.
Cook et al.; Trigeminal nerve stimulation in major depressive disorder: acute outcomes in an open pilot study; Epilepsy and Behavior; 28(2): pp. 221-226; Aug. 31, 2013.
Degiorgio et al., Trigeminal nerve stimulation for epilepsy: long-term feasibility and efficacy; Neurology; 72(10): pp. 936-938; Mar. 10, 2009.

(56) References Cited

OTHER PUBLICATIONS

Degiorgio et al.; Randomized controlled trial of trigeminal nerve stimulation for drug-resistant epilepsy; Neurology; 80(9); pp. 786-791; Feb. 26, 2013.
Elder et al.; The cortisol awakening response—applications and implications for sleep medicine; Sleep Medicine Reviews; 18(3): pp. 215-224; Jun. 30, 2014.
Eschenko et al.; Noradrenergic neurons of the locus coeruleus are phase locked to cortical up-down states during sleep; Cerebral Cortex; 22(2); pp. 426-435; Feb. 1, 2012.
Franowicz et al.; Treatment with the noradrenergic alpha-2 agonist clonidine, but not diazepam, improves spatial working memory in normal young rhesus monkeys; Neuropsychopharmacology; 21(5); pp. 611-621; Nov. 1, 1999.
Garraway et al.; Modulatory actions of serotonin, norepinephrine, dopamine, and acetylcholine in spinal cord deep dorsal horn neurons; Journal of Neurophysiology; 86(5); pp. 2183-2194; Nov. 1, 2001.
Golestanirad et al; Analysis of fractal electrodes for efficient neural stimulation; Frontiers in Neuroengineering; 6(3); 10 pages; Jul. 2013.
Granger et al.; Salivary alpha-amylase in biobehavioral research: recent developments and applications; Annals of the New York Academy of Sciences; 1098(1); pp. 122-144; Mar. 1, 2007.
Gummadavelli et al.; Neurostimulation to improve level of consciousness in patients with epilepsy. Neurosurgical Focus; 38(6); pp. E10; (manuscript version, 14 pages); Jun. 2015.
Hajos et al.; Norepinephrine but not serotonin reuptake inhibitors enhance theta and gamma activity of the septo-hippocampal system; Neuropsychopharmacology; 28(5); pp. 857-864; May 1, 2003.
Hass et al.; Waking with the hypothalamus. Pflugers Arch R Eur. J. Physiol.; 463(1): pp. 31-42; Jan. 1, 2012.
Herwig et al.; Intracortical excitability is modulated by a norepinephrine-reuptake inhibitor as measured with paired-pulse transcranial magnetic stimulation; Psychopharmacology (Berl); 164(2): pp. 228-232; Nov. 18, 2002.
Hirotsu et al.; Interactions between sleep, stress, and metabolism; From physiological to pathological conditions; Sleep Science; 8(3); pp. 143-152; Nov. 2015.
Horvath et al.; Evidence that transcranial direct current stimulation (tDCS) generates little-to-no reliable neurophysiologic effect beyond MEP amplitude modulation in healthy human subjects: A systematic review; Neuropsychologia; 66: pp. 213-236; Jan. 31, 2015.
Just et al.; Bold responses to trigeminal nerve stimulation; Magnetic Resonance Imaging; 28(8): pp. 1143-1151; Oct. 31, 2010.
Kubota et al.; Role of the brain stem in cardiovascular changes induced by stimulation of the trigeminal nerve; Anesthesia Progress; 36(4-5); pp. 236-237; Jul. 1989.
Lee et al.; Neuromodulation of Brain States; Neuron; 76(1): pp. 209-222. Oct. 4, 2012.
Leproult et al.; Sleep loss results in an elevation of cortisol levels the next evening; Sleep; 20(10): pp. 865-870; Oct. 1997.
Lovibond et al.; The structure of negative emotional states: Comparison of the Depression Anxiety Stress Scales (DASS) with the Beck Depression and Anxiety Inventories; Behaviour Research and Therapy; 33(3); pp. 335-343; Mar. 31, 1995.
Lu et al.; A putative flip-flop switch for control of REM sleep; Nature; 441 (7093): pp. 589-594; Jun. 1, 2006.
Magis et al.; Safety and patients' satisfaction of transcutaneous supraorbital neurostimulation (tSNS) with the Cefaly(R) device in headache treatment: a survey of 2,313 headache sufferers in the general population; The Journal of Headache and Pain, 14(1); pp. 95; (manuscript version, 8 pages) Dec. 1, 2013.
Mcgough et al.; An eight-week, open-trial, pilot feasibility study of trigeminal nerve stimulation in youth with attention-deficit/hyperactivity disorder; Brain Stimulation; 8(2); pp. 299-304; Apr. 30, 2015.
Meltzer et al; Direct comparison of two new actigraphs and polysomnography in children and adolescents; Sleep; 35(1); pp. 159-166; Jan. 1, 2012.

Nash et al.; Differential activation of the human trigeminal nuclear complex by noxious and non-noxious orofacial stimulation; Human Brain Mapping; 30(11); pp. 3772-3782; Nov. 1, 2009.
Nieuwenhuis et al.; Decision making, the P3, and the locus coeruleus-norepinephrine system; Psychological Bulletin; 131(4); pp. 510-532; Jul. 2005.
Parvizi et al.; Consciousness and the brainstem; Cognition; 79(1): pp. 135-160; Apr. 30, 2001.
Penzel et al.; Dynamics of Heart Rate and Sleep Stages in Normals and Patients with Sleep Apnea; Neuropsychopharmacology; 28(S1); pp. S48-S53; Jul. 1, 2003.
Piquet et al.; Supraorbital transcutaneous neurostimulation has sedative effects in healthy subjects; BMC Neurology; 11(1); p. 135; (manual transcript, 8 pages); Oct. 28, 2011.
Plewnia et al.; Enhancement of human cortico-motoneuronal excitability by the selective norepinephrine reuptake inhibitor reboxetine; Neuroscience Letters; 330(3); pp. 231-234; Sep. 27, 2002.
Pusch et al.; Electrical stimulation of the vestibular system prevents postoperative nausea and vomiting; Acta Annesthesiol Scand.; 44(9); pp. 1145-1148; Oct. 2000.
Riemann et al.; The hyperarousal model of insomnia: A review of the concept and its evidence; Sleep Medicine Reviews; 14(1); pp. 19-31; Feb. 28, 2010.
Rill et al.; Pedunculopontine arousal system physiology—implications for insomnia; Sleep Science; 8(2); pp. 92-99; Jun. 30, 2015.
Rohleder et al.; Psychosocial stress-induced activation of salivary alpha-amylase: an indicator of sympathetic activity; Annals of the New York Academy of Sciences; 1032(1); pp. 258-263; Dec. 1, 2004.
Sara; The locus coeruleus and noradrenergic modulation of cognition; Nature Reviews Neuroscience; 10(3): pp. 211-223. Mar. 1, 2009.
Schmidt et al.; Adrenaline rush: the role of adrenergic receptors in stimulant-induced behaviors; Molecular Pharmacology; 85(4): pp. 640-650; Apr. 1, 2014.
Seugnet et al.; Identification of a biomarker for sleep drive in flies and humans; Proceedings of the National Academy of Sciences; 103(52); pp. 19913-19918; Dec. 26, 2006.
Shiozawa et al.; Transcutaneous vagus and trigeminal nerve stimulation for neuropsychiatric disorders: a systematic review; Arquivos de neuro-psiquiatria; 72(7): pp. 542-547; Jul. 2014.
Siegel; Brain mechanisms that control sleep and waking. Naturwissenschaften; 91(8); pp. 355-365; Aug. 1, 2004.
Somana et al.; Cerebellar afferents from the trigeminal sensory nuclei in the cat. Brain Res.; 38(1); pp. 57-64; Jan. 1980.
Strassman et al; Response of brainstem trigeminal neurons to electrical stimulation of the dura; Brain Research; 379(2): pp. 242-250; Aug. 6, 1986.
Tanaka et al.; Salivary alpha-amylase and cortisol responsiveness following electrically stimulated physical stress in bipolar disorder patients; Neuropsychiatric Disease and Treatment; 8; pp. 1899-1905; Jan. 1, 2013.
Thoma et al.; Acute stress responses in salivary alpha-amylase predict increases of plasma norepinephrine; Biological Psychology; 91(3): pp. 342-348; Dec. 31, 2012.
Tremblay et al.; Uncertain Outcome of Prefrontal tDCS; Brain Stimulation; 7(6): pp. 773-783; Dec. 31, 2014.
Trevizol et al.; Trigeminal Nerve Stimulation (TNS) for Generalized Anxiety Disorder: A Case Study; Brain Stimulation; 8(3): pp. 659-660; Jan. 1, 2015.
Trevizol et al.; Trigeminal Nerve Stimulation (TNS) for Post-traumatic Stress Disorder: A Case Study; Brain Stimulation; 8(3): pp. 676-678; Jan. 1, 2015.
Tyler et al.; Transdermal neuromodulation of noradrenergic activity suppresses psychophysiological and biochemical stress responses in humans; Scientific Reports; 5; (manual transcript, 22 pages); Feb. 8, 2015.
Tyler et al.; U.S. Appl. No. 62/166,674 entitled "Systems And Methods For Suppression Of Stress Responses By Transdermal Electrical Neuromodulation," filed May 26, 2015.

(56) References Cited

OTHER PUBLICATIONS

Upadhyay et al.; Noninvasive mapping of human trigeminal brainstem pathways; Magnetic Resonance in Medicine; 60(5): pp. 1037-1046; Nov. 1, 2008.
Van Stegeren et al.; Salivary alpha amylase as marker for adrenergic activity during stress: effect of betablockade; Psychoneuroendocrinology; 31(1); pp. 137-141; Jan. 31, 2006.
Voisin et al.; Nociceptive stimulation activates locus coeruleus neurones projecting to the somatosensory thalamus in the rat; The Journal of Physiology; 566( 3); pp. 929-937; Aug. 1, 2005.
Voss et al.; Induction of self awareness in dreams through frontal low current stimulation of gamma activity; Nature Neuroscience; 17(6); pp. 810-812; Jun. 1, 2014.
Watson et al.; Development and validation of brief measures of positive and negative affect: the PANAS scales; Jouranl of Personality and Social Psychology; 54(6); pp. 1063-1070; Jun. 1988.
Weiss et al; Validity of Activity-Based Devices to Estimate Sleep; Journal of Clinical Sleep Medicine : 6(4); pp. 336-342; Aug. 2010.
Goldwasser et al.; U.S. Appl. No. 15/264,224 entitled "Apparatuses and methods for neuromodulation," filed Sep. 13, 2016.
Charlesworth et al.; U.S. Appl. No. 15/384,249 entitled "Apparatuses and methods for transdermal electrical stimulation of nerves to modify or induce a cognitive state," filed Dec. 19, 2017.
Jeffery; U.S. Appl. No. 15/380,028 entitled "Electrodes having surface exclusions," filed Dec. 15, 2017.
Tyler et al.; U.S. Appl. No. 15/460,138 entitled "Systems and methods for transdermal electrical stimulation to improve sleep," filed Mar. 15, 2017.
Pal et al.; U.S. Appl. No. 14/956,193 entitled "Transdermal electrical stimulation devices for modifying or inducing cognitive state," filed Dec. 1, 2015.
Tyler et al.; U.S. Appl. No. 15/536,148 entitled "Methods and apparatuses for transdermal stimulation of the outer ear," filed Jun. 15, 2017.
Tyler et al.; U.S. Appl. No. 15/536,151 entitled "Systems and methods for transdermal electrical stimulation to improve sleep," filed Jun. 15, 2017.

* cited by examiner

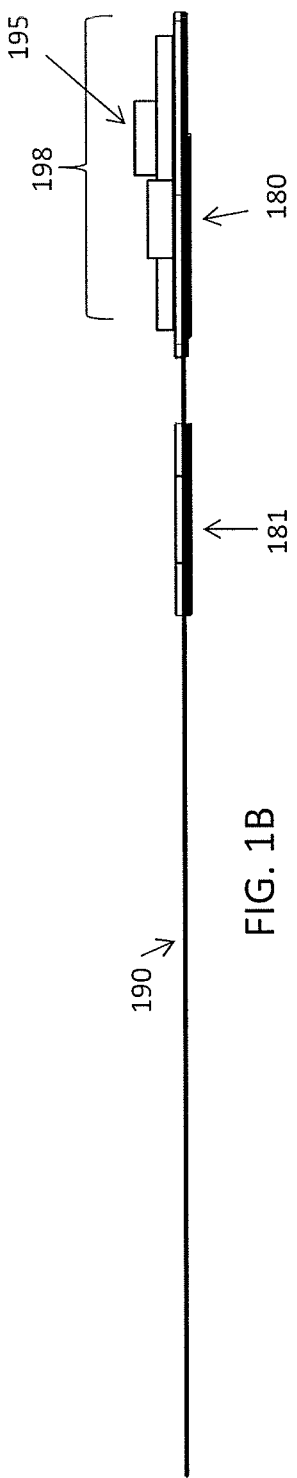

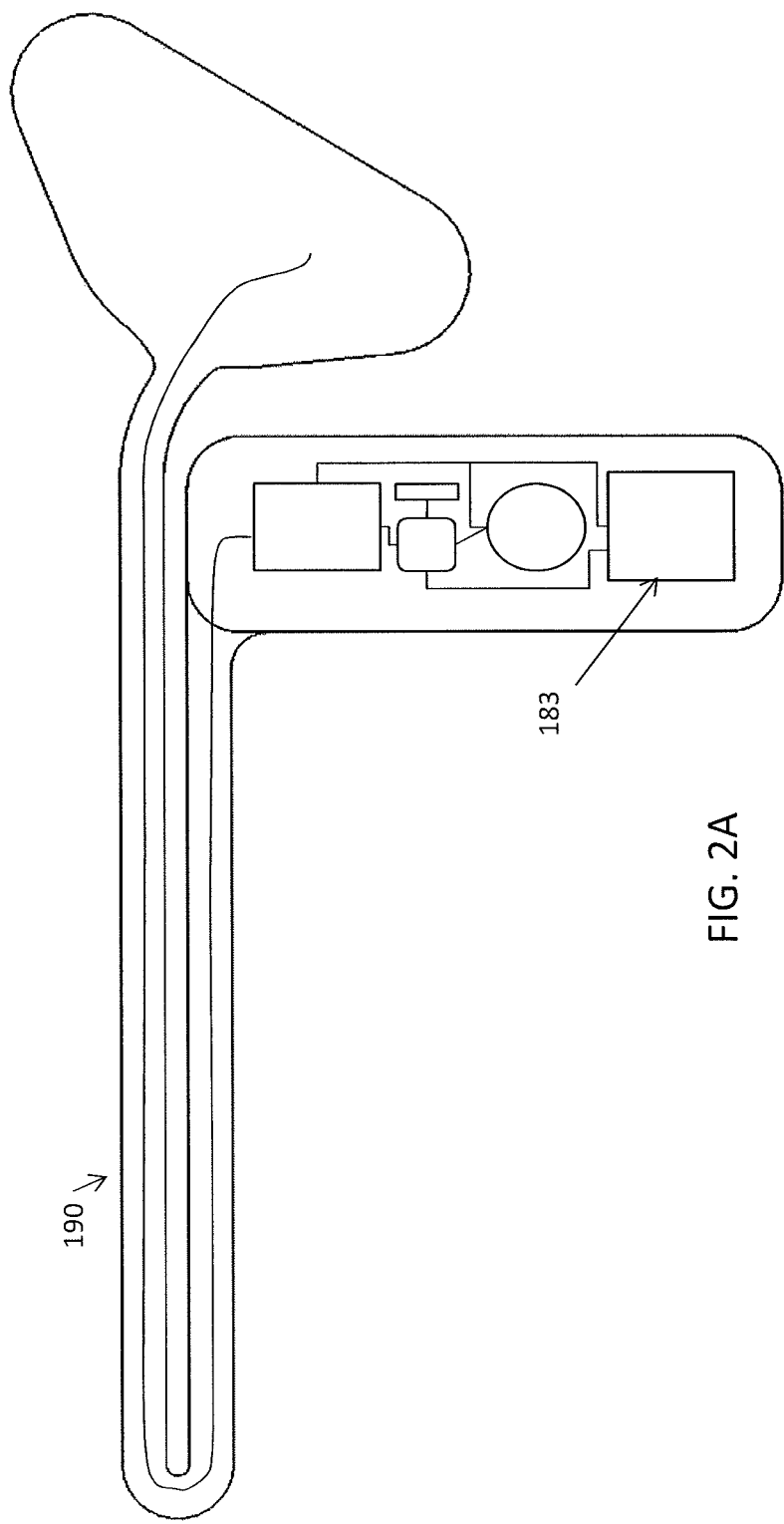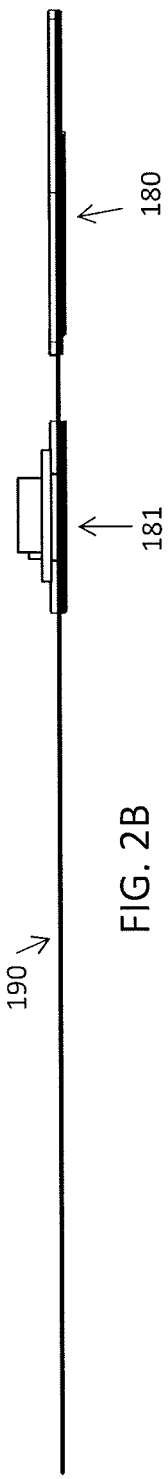
FIG. 2A
FIG. 2B

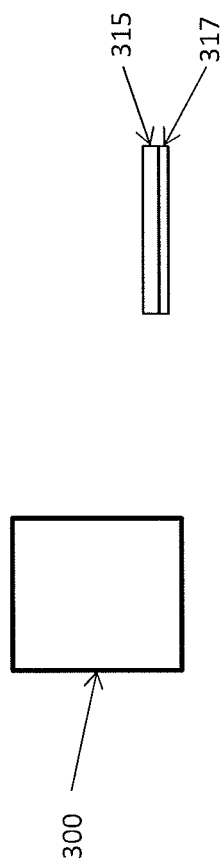
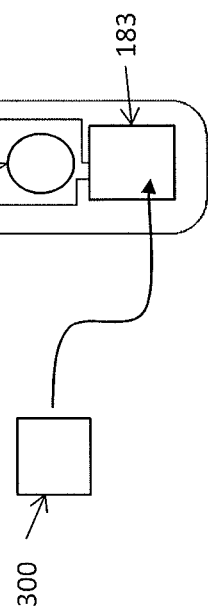
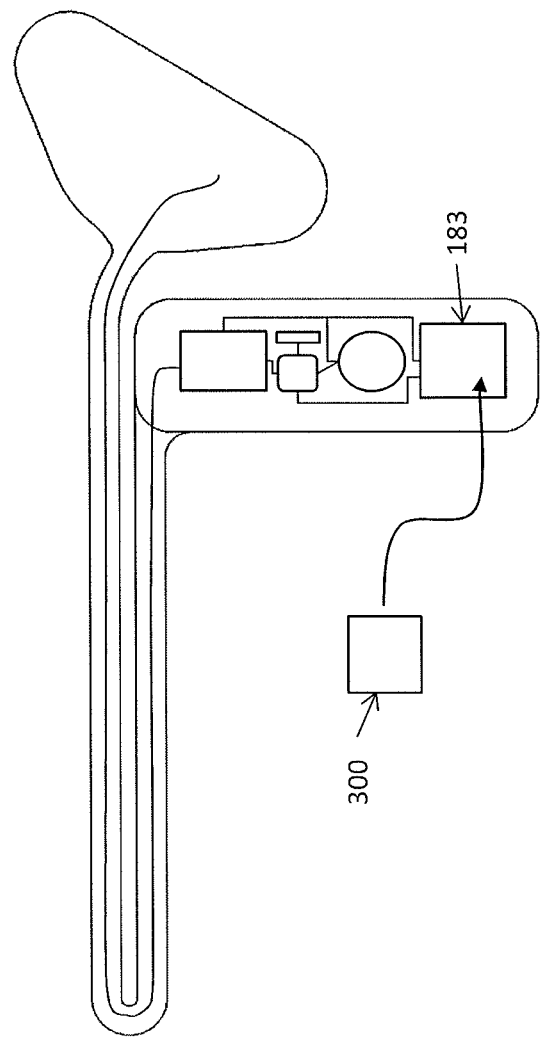
FIG. 3A
FIG. 3B
FIG. 3C

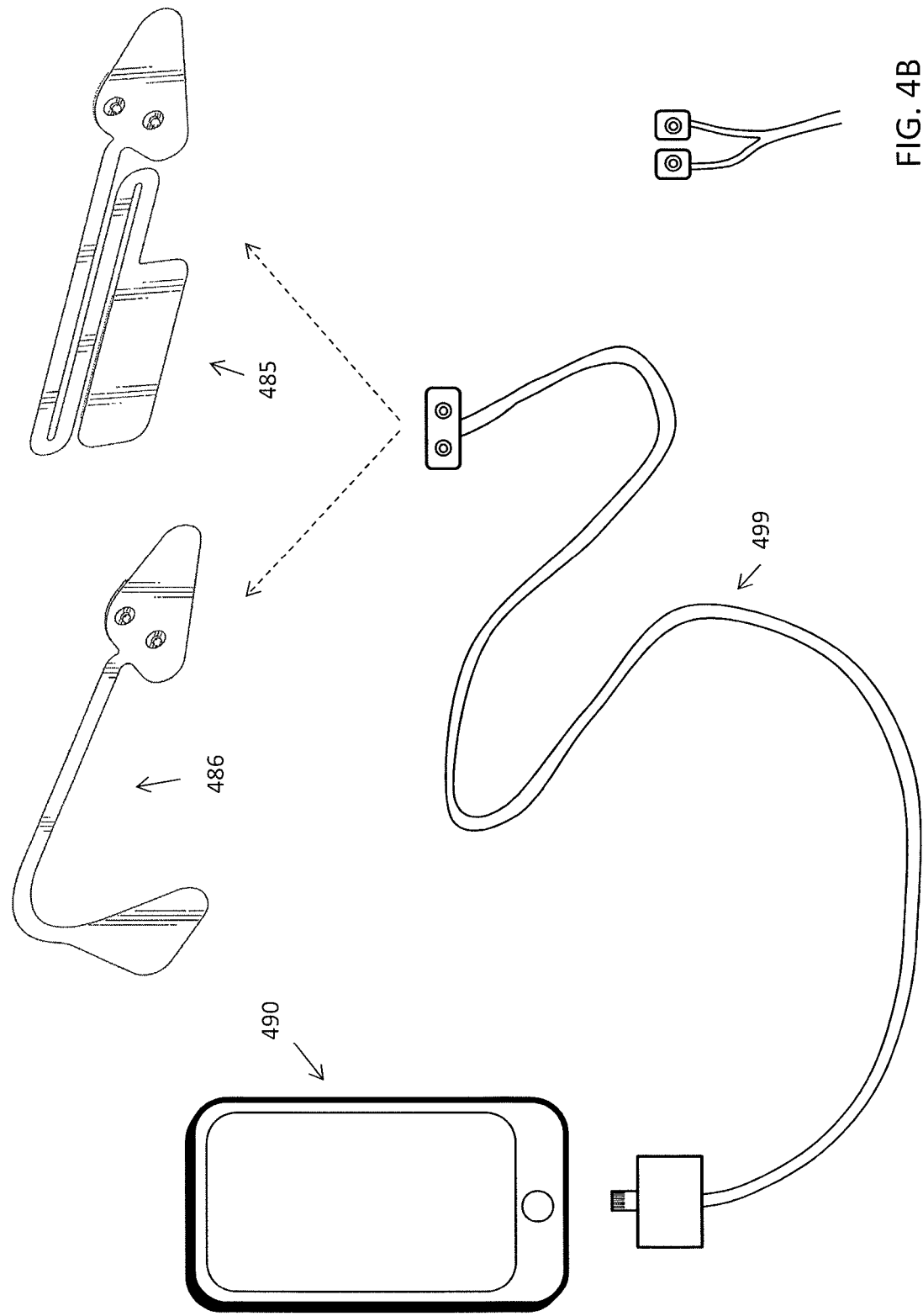

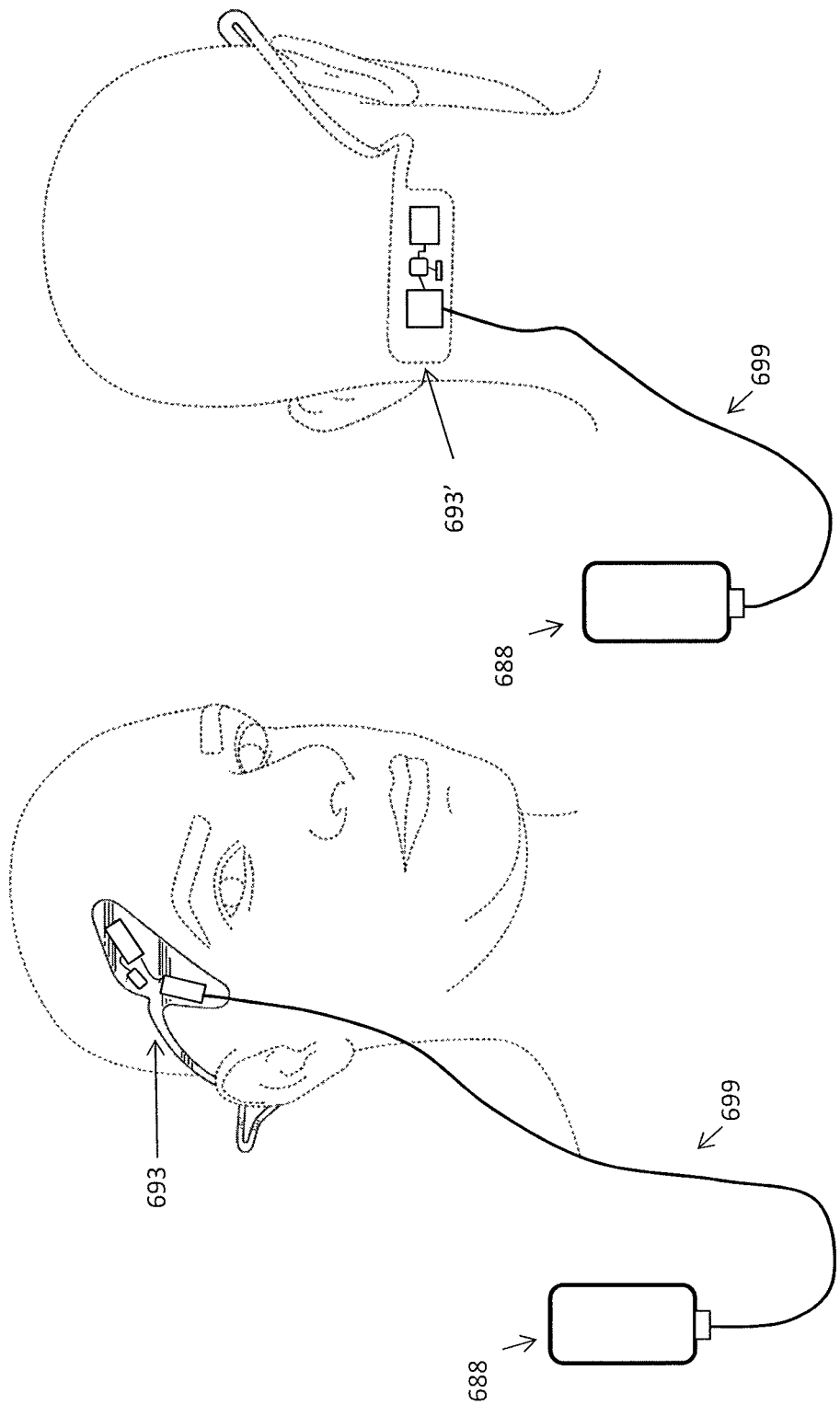

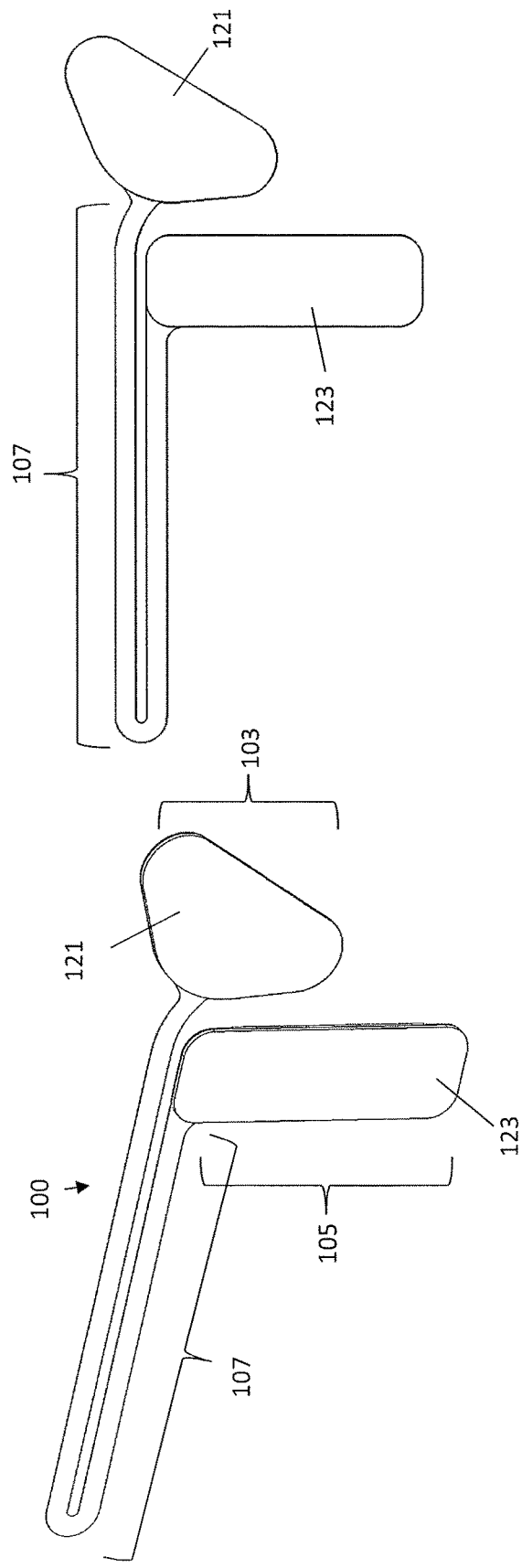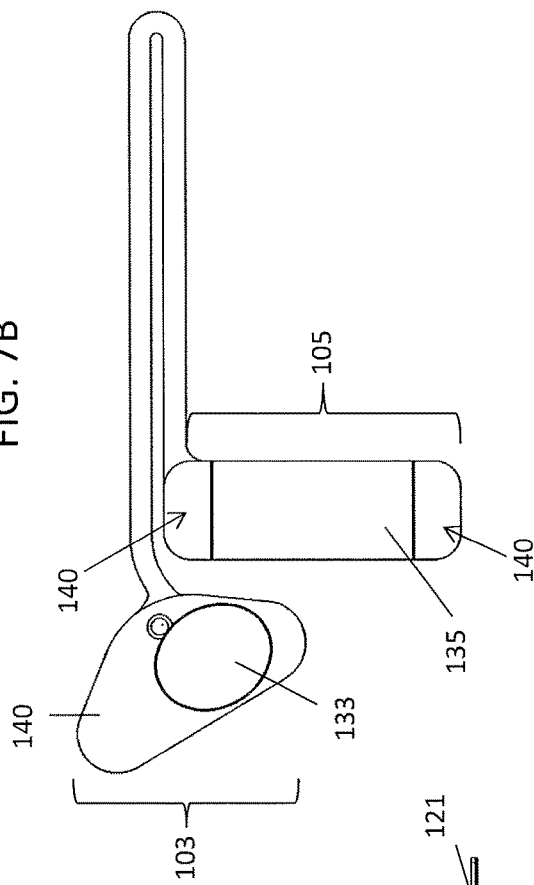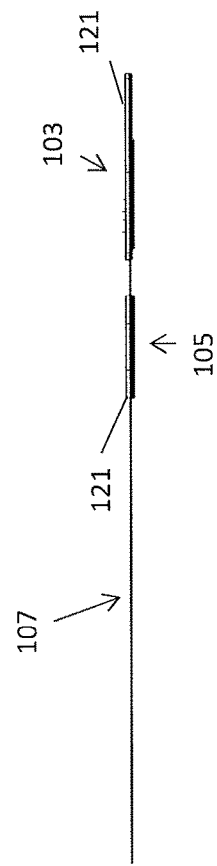

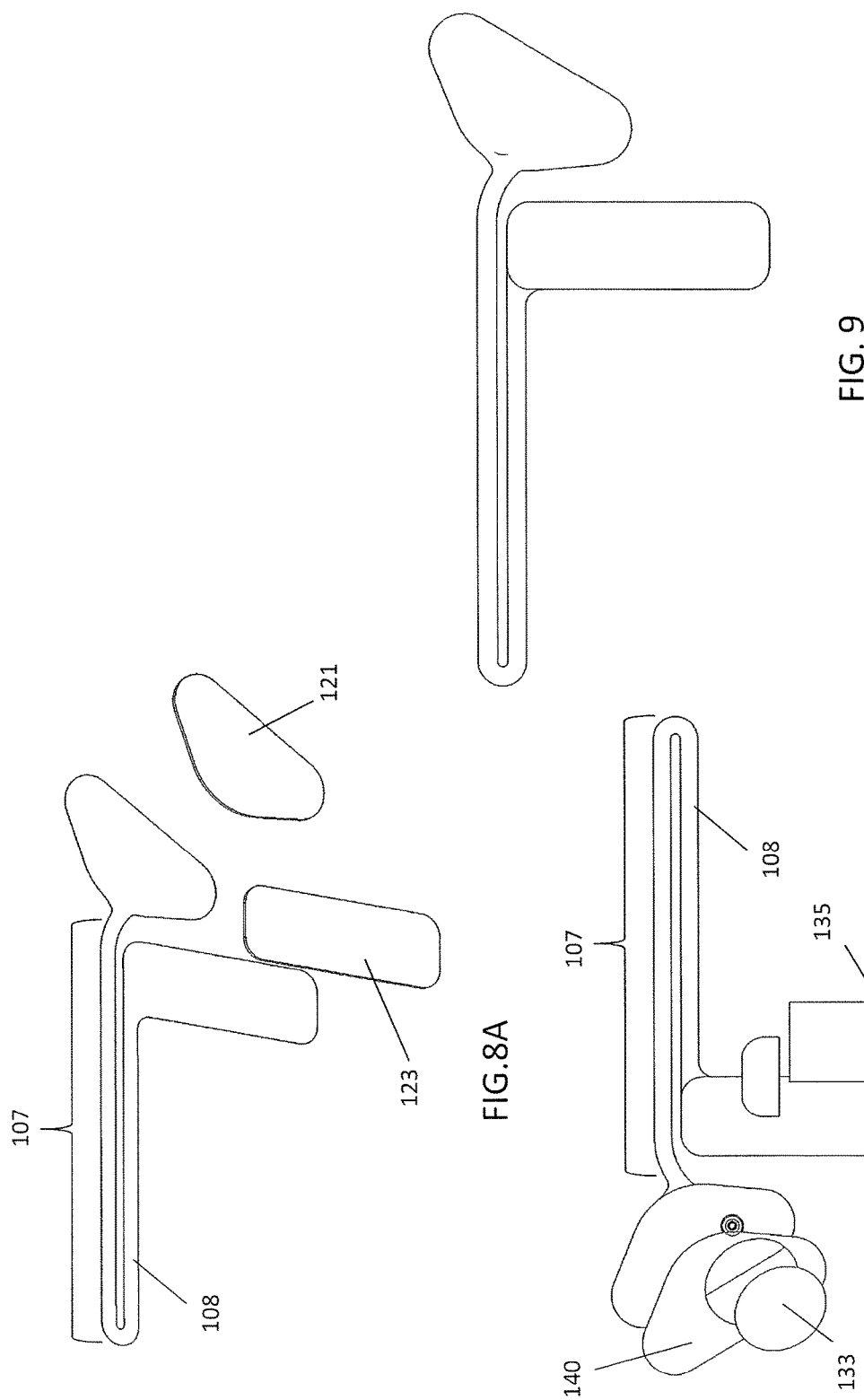

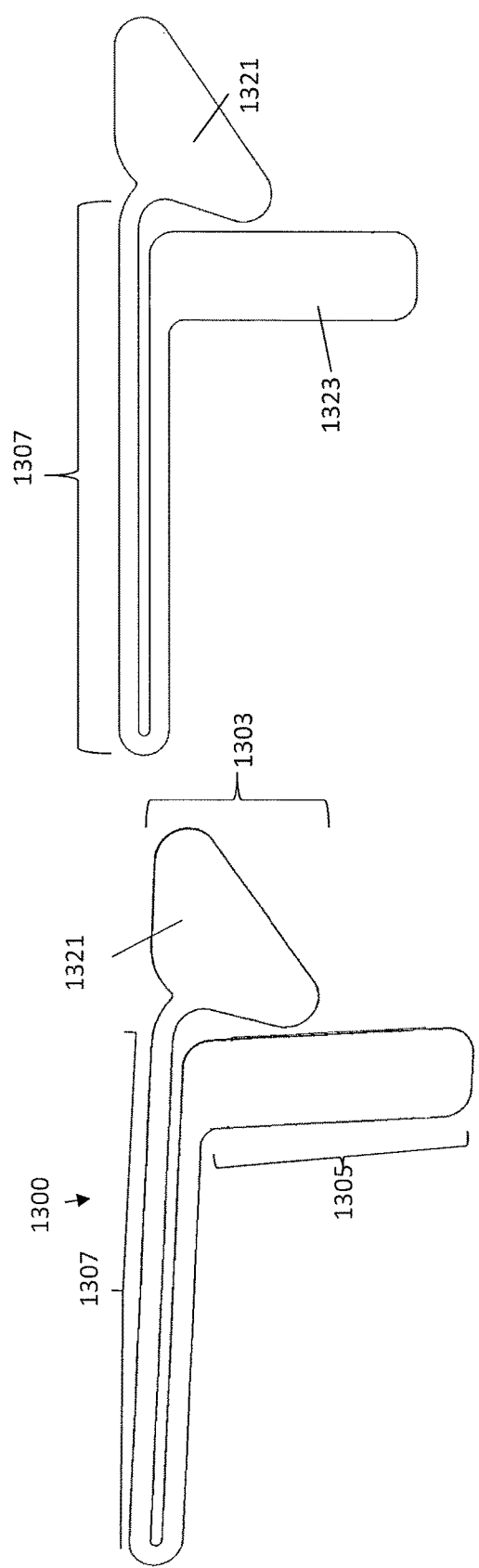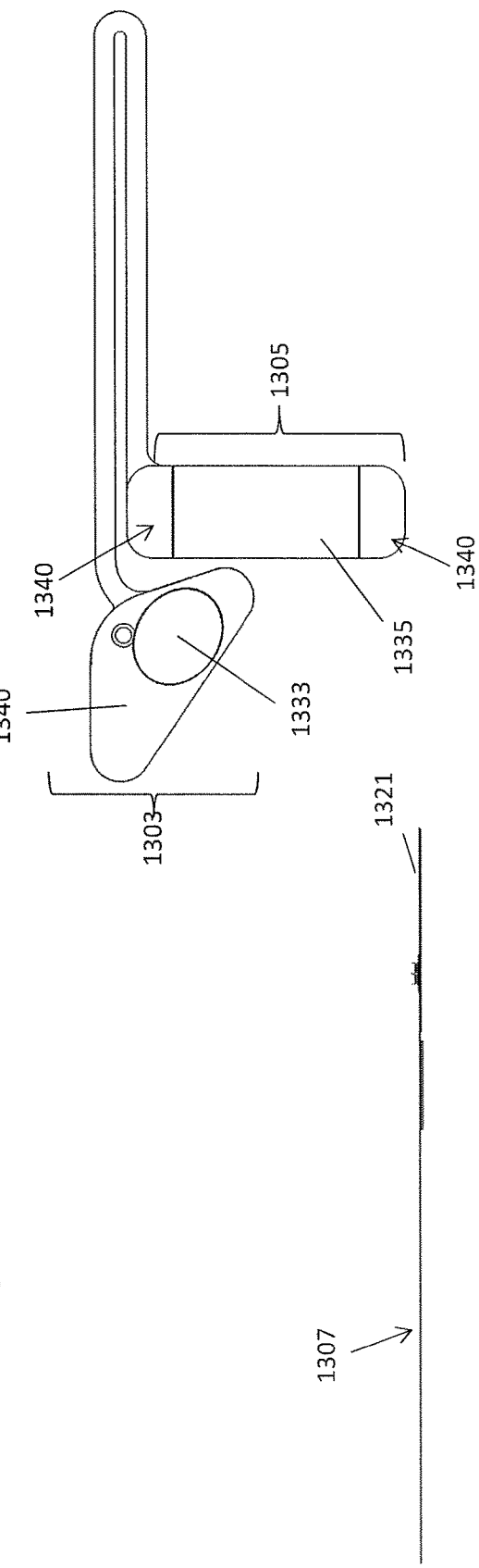
FIG. 13A  FIG. 13B  FIG. 13C  FIG. 13D

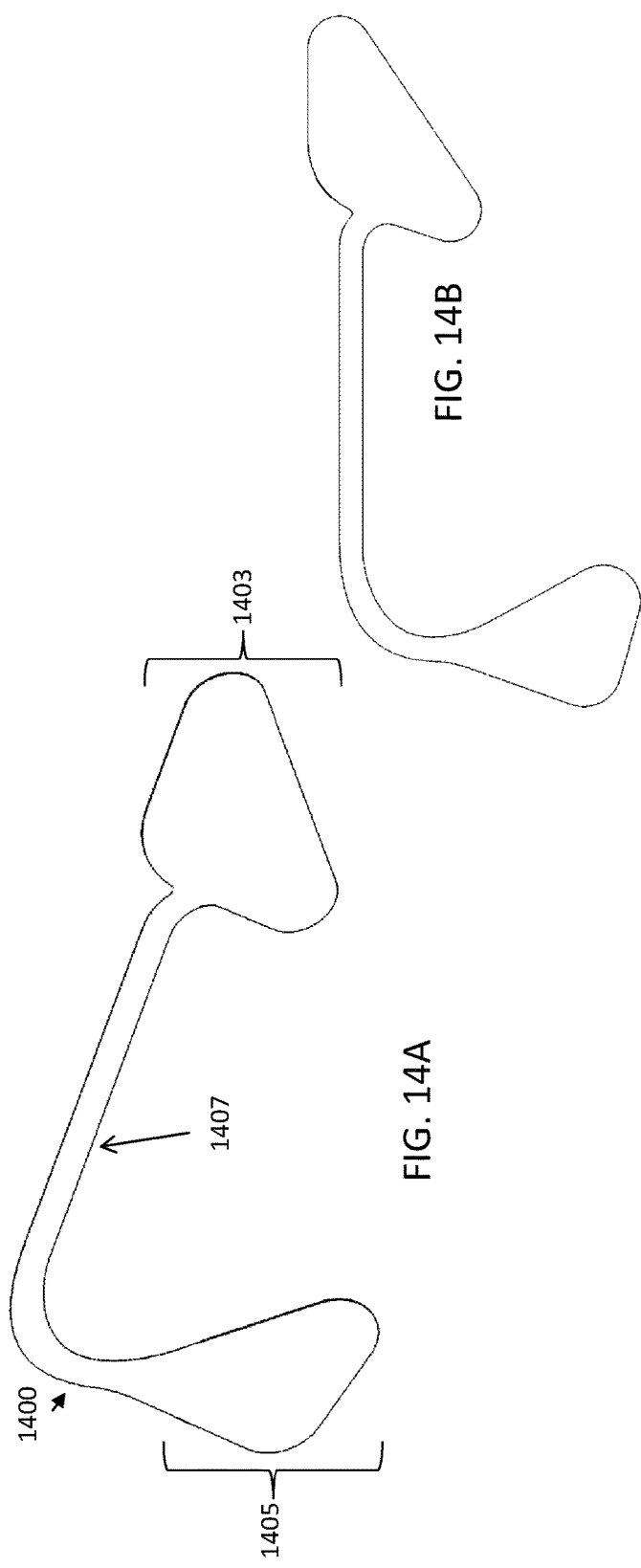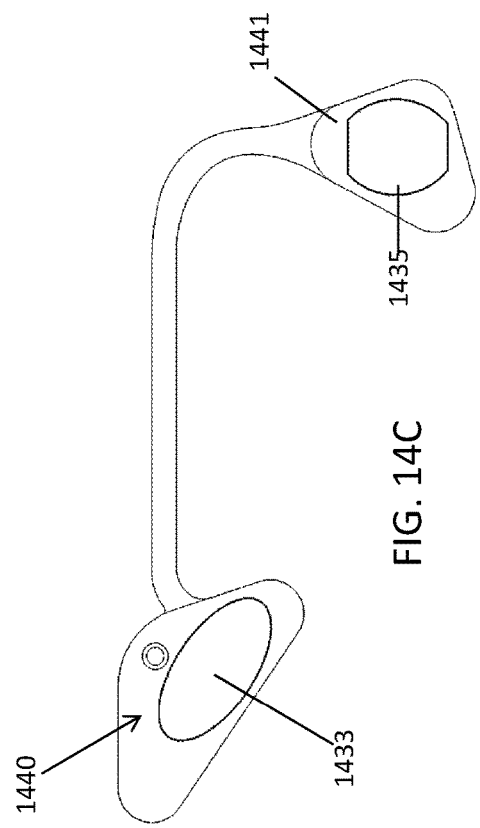

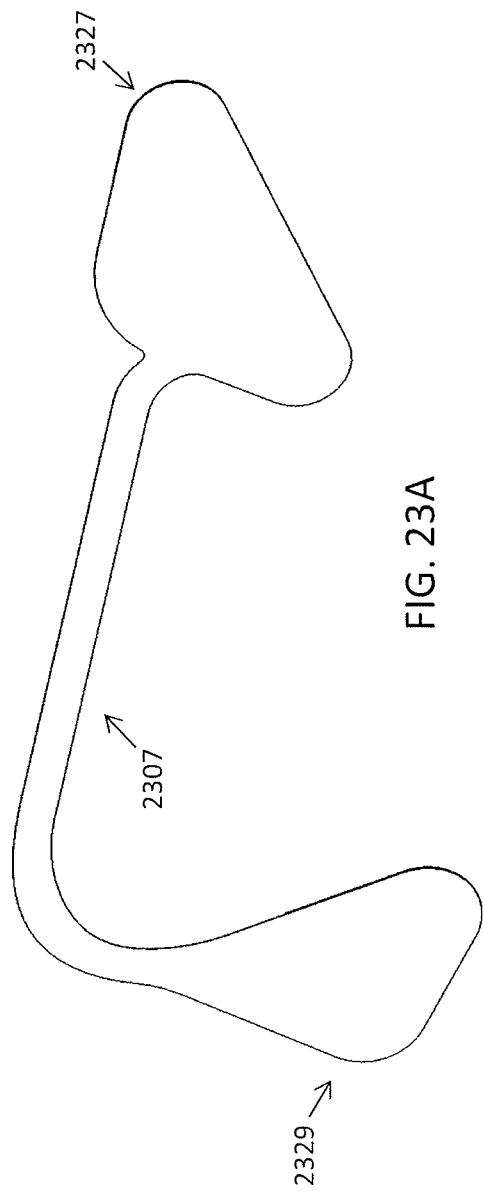
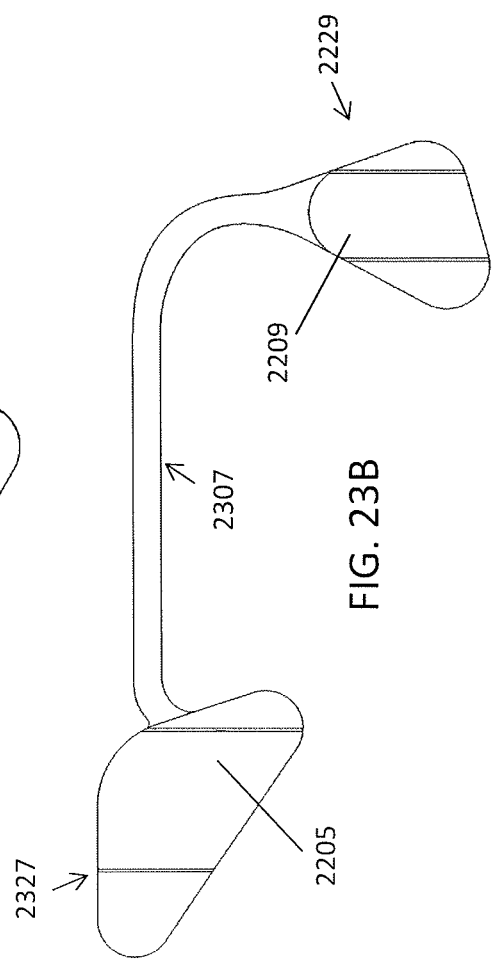

METHODS AND APPARATUSES FOR TRANSDERMAL ELECTRICAL STIMULATION

CROSS REFERENCE TO RELATED APPLICATIONS

This application claims priority to each of the following: U.S. Provisional Patent Application No. 62/168,615, filed on May 29, 2015, and titled "METHODS AND APPARATUSES FOR TRANSDERMAL ELECTRICAL STIMULATION"; U.S. Provisional Patent Application No. 62/190,211, filed on Jul. 8, 2015, and titled "METHODS AND APPARATUSES FOR TRANSDERMAL ELECTRICAL STIMULATION"; U.S. Provisional Patent Application No. 62/200,256, filed on Aug. 3, 2015, and titled "METHODS AND APPARATUSES FOR TRANSDERMAL ELECTRICAL STIMULATION"; U.S. Provisional Patent Application No. 62/213,949, filed on Sep. 3, 2015, and titled "METHODS AND APPARATUSES FOR TRANSDERMAL ELECTRICAL STIMULATION," each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are non-invasive neuromodulation apparatuses, including devices and systems, and methods of their use.

BACKGROUND

Noninvasive neuromodulation technologies that affect neuronal activity can modulate and potentially alter behavior, cognitive states, perception, and motor output without requiring an invasive procedure. Transcranial and/or transdermal electric stimulation (hereinafter "TES") using scalp electrodes has been used to affect brain function in humans in the form of transcranial alternating current stimulation (hereinafter "tACS"), transcranial direct current stimulation (hereinafter "tDCS"), cranial electrotherapy stimulation (hereinafter "CES"), and transcranial random noise stimulation (hereinafter "tRNS"). Systems and methods for TES have been disclosed (see for example, Capel U.S. Pat. No. 4,646,744; Haimovich et al. U.S. Pat. No. 5,540,736; Besio et al. U.S. Pat. No. 8,190,248; Hagedorn and Thompson U.S. Pat. No. 8,239,030; Bikson et al. U.S. Patent Application Publication No. 2011/0144716; and Lebedev et al. U.S. Patent Application Publication No. 2009/0177243). tDCS systems with numerous electrodes and a high level of configurability have been disclosed (see for example Bikson et al. U.S. Patent Application Publication Nos. 2012/0209346, 2012/0265261, and 2012/0245653).

TES has been used therapeutically in various clinical applications, including treatment of pain, depression, epilepsy, and tinnitus. Despite the research to date on TES neuromodulation, existing systems and methods for delivering TES are lacking. In particular, miniaturized systems that incorporate hardware components with a low profile, comfortable, and/or familiar form factor for convenient, comfortable, and on-the-go TES, have been lacking.

Most electrical stimulation systems targeting the nervous system incorporate a tabletop or handheld hardware comprising a user interface, electrical control circuitry, a power supply (e.g. battery), wires leading to electrodes affixed to a user, and predetermined and/or preconfigured electrical stimulation protocols. Conventional systems are limited regarding the comfort, design, and use of electrodes to deliver TES waveforms. For example, they may use uncomfortable and inflexible electrodes, such that the electrodes do not conform to the body of the user, resulting in uneven impedance, increased irritation during stimulation, and reduced cognitive effects. Further, most prior art electrodes are not able to act as substrates for electronic circuits and are not well suited to attach to a wearable neurostimulator so that the neurostimulator is held to the body by the electrode.

Although other designs of neuromodulation devices included small, wearable devices, it would be desirable to have a neuromodulation device that was not only more cost-effective to produce but also possessing an even more discrete profile. Further, it would be useful to provide an integrated neuromodulation unit and electrode assembly. There is a need for integrated, lightweight, low-profile, wearable neuromodulation systems, that integrate the electrodes and neuromodulation components such that there is no concern for maintaining the connection between the electrodes and neuromodulation components when contact is between two or more widely separated regions of the wearer's body, including the head or head and neck. Integrating electrodes with a neuromodulation unit is beneficial for reducing weight and improving the ease of wearing the system adhesively on the skin.

In most related designs, neurostimulators were separate units from the electrode apparatuses that could be coupled together to provide electrical stimulation to the wearer. For example, existing TES systems generally provide a separate neurostimulation module and dermally-adhesive electrode apparatus, as described (for example) in PCT applications by some of the named inventors of this application: PCT/US2015/031,966 titled "CANTILEVER ELECTRODES FOR TRANSDERMAL AND TRANSCRANIAL STIMULATION" and PCT/US2015/031,424 titled "WEARABLE TRANSDERMAL NEUROSTIMULATORS". A new, simpler, and easier to use system requires no connecting of separate units by designing the electrodes and the neuromodulation components integrated into a unified system on a flexible circuit backing. Similar to prior device designs, the present integrated neuromodulation device may include a pH regulating consumptive layer that is flexible and can make reliable electrical contact with the user's skin. An integrated neuromodulation device can be designed to include a variety of electrode configurations. Finally, it would remain useful to provide electrode assemblies that are capable of making reliable and durable electrical contact with the user at various locations on the user's head and neck regions.

To date, TES systems, including wearable TES systems, generally require a microprocessor and power source (e.g. battery). New TES system that remove the need for either or both of a microprocessor and power source (e.g. battery) by connecting directly to a smartphone, tablet, or other user computing device would permit TES systems to be smaller, lighter weight, less expensive, simpler to operate, and better for the environment (i.e. due to the elimination or size reduction of a battery contained on the TES system).

The apparatuses (e.g., devices and systems), and methods described herein may address at least the needs identified above.

SUMMARY OF THE DISCLOSURE

Described herein are single-use or limited-use TES neuromodulation apparatuses including integrated electrodes and neuromodulation components that can be worn, e.g., on a user's head and/or neck region (although they may be adapted for other body regions) for electrical stimulation to modulate the user's cognitive state. These apparatuses may be referred to as TES patches or neurostimulation patches, and may be formed of a flex-circuit material. Also described herein are waveform selectors, which may be applied to these apparatuses to select and/or program the limited-use TES neurostimulator in order to apply a predetermined waveform or set of waveforms, or to adjust a waveform, to evoke a cognitive effect. A waveform selector may be a near-field communication component (e.g., RFID, other inductive mechanisms) that communicates with the TES neurostimulator (TES patch) via an NFC antenna contained thereon.

Also described herein are TES neuromodulation apparatuses including connecting cables having circuitry configured to communicate between a portable personal electronics device (e.g., smartphone, tablet, smartwatch, or other wearable electronics) and an electrode apparatus including connectors, such as the electrode apparatuses described in U.S. patent application Ser. No. 14/634,664, titled "CANTILEVER ELECTRODES FOR TRANSDERMAL AND TRANSCRANIAL STIMULATION" and filed on Feb. 27, 2015, herein incorporated by reference in its entirety. The personal electronic device may include software, firmware, and/or hardware that controls the application of TES waveforms, and the cable (which may be referred to herein as a smart cable or a TES cable neurostimulator) may include circuitry to amplify or otherwise modify (i.e. by incorporating a capacitive discharge) the waveforms. In some variations the TES cable neurostimulator may include circuitry including any of: current generator circuitry (e.g., waveform generators), safety circuitry, user interface (e.g. buttons, touch interface), controller, memory, processor, digital-to-analog and/or analog-to-digital converters, or the like. The TES cable neurostimulator may be configured to connect to a port (e.g., a USB port (i.e. a micro USB port), a Lightning Connector™, audio jack, etc.) of the portable electronics device. In general, the TES cable neurostimulator may include any of the components (and their functions) of the wearable TES neurostimulator devices described, for example, in U.S. patent application Ser. No. 14/715,470, titled "TRANSDERMAL NEUROSTIMULATOR ADAPTED TO REDUCE CAPACITIVE BUILD-UP" and filed on May 18, 2015, which is herein incorporated by reference in its entirety.

The TES neurostimulator functionality may be shared between the TES cable neurostimulator and the portable electronics device (e.g., smartphone). For example, in some variations a smartphone is configured to generate a TES waveform (including any of the TES ensemble waveforms such as those described in U.S. patent application Ser. No. 14/639,015, titled "TRANSDERMAL ELECTRICAL STIMULATION DEVICES FOR MODIFYING OR INDUCING COGNITIVE STATE" and filed Mar. 4, 2015 and U.S. patent application Ser. No. 14/715,476, titled "METHODS AND APPARATUSES FOR AMPLITUDE-MODULATED ENSEMBLE WAVEFORMS FOR NEUROSTIMULATION," and filed May 18, 2015, each of which is herein incorporated by reference in its entirety) and then deliver it to the TES cable neurostimulator that is connected to an electrode assembly; the TES cable neurostimulator amplifies (and, if necessary, interprets, modifies, and/or parses) the signal from the portable personal electronics device, and applies it between the electrodes of the electrode assembly for delivery to the subject. The TES cable neurostimulator may include circuitry configured to confirm that the cable is connected to an electrode assembly, and/or that the electrode assembly is attached to the user's head; alternatively, this functionality may be performed by the personal electronics device (e.g., smartphone) to which the TES cable neurostimulator is connected. In some variations, the TES cable neurostimulator includes a waveform generator and/or a current generator but receives control information from the personal electronics device (e.g. to determine the parameters of a waveform to deliver to the electrode assembly; to start or stop a waveform; to modulate a parameter of an ongoing waveform; etc.).

Also described herein are intermediate embodiments between the completely integrated "patch" TES neurostimulator devices described (which may be limited-use or single-use) and typically include their own power supply, and the TES cable neurostimulator devices, which connect to an electrode apparatus that does not include a power supply or neurostimulator circuitry (though they may include other circuitry, such as electrode-identification circuitry or physiological recording circuitry). For example, an intermediate embodiment may include a cable that is configured to provide power and/or communication from a portable electronics device (e.g., smartphone) and a partially-integrated electrode assembly onto which TES neurostimulator circuitry is included. For example, a partially-integrated TES neurostimulator patch may include all of the neurostimulator circuitry, but may not have an independent power supply (e.g., battery); alternatively, as with the TES cable neurostimulator embodiment, an intermediate apparatus may share the neurostimulator functions and/or components with the personal computing device, and may use the processor of the personal computing device to control the selection and formation of the waveforms to be applied by the patch portion.

In general, described herein are wearable neuromodulation devices configured to be worn on a subject's head or on the subject's head and neck (though in some variations, the electrodes may be configured to connect to a portion of a subject's body other than the head or neck). The neuromodulation systems described herein may be referred to as neurostimulation systems, neurostimulator systems, neuromodulator systems, applicator systems, neuromodulation applicator systems, or the like. Some of the neuromodulation devices described herein integrate the electrode assembly and the neuromodulation components into one device or onto one flexible substrate (also referred to as a strip) or strip-like assembly.

The wearable neuromodulation devices described herein are small, lightweight and specifically adapted to be conforming to the subject so that they can be worn while the subject goes about their daily activities. In particular, these devices are adapted to be worn on the subject's head (e.g., at the temple region) comfortably even while wearing headgear such as hats, glasses, hoods, scarves, or the like. These devices typically have a first surface (subject-facing surface) that has a curved and twisted shape so that an electrode on the surface conforms to a subject's temple region. In some examples, the thickness of the overall device is approximately the same throughout. In other examples, there may be curves on the first surface of the neuromodulation device such that the neuromodulation device can better conform to the subject's temple and neck regions. In yet other examples, the thickness of the device (measured from the first surface) is typically thinner at one end and thicker at the other end. The thinner end region may be configured to be oriented relative to the subject's eye, with the thicker region worn higher on the subject's head, toward the center of the subject's forehead. These devices may also be adapted to conform to other body areas, including the neck. These neuromodulation devices may also be referred to as neurostimulation devices, neurostimulators, neuromodulators, applicators, neuromodulation applicators, electrical stimulators, or the like.

The electrode may also be referred to as an electrode assembly, electrode pad, electrode system, strip, electrode strip, or electrode apparatus, and may be durable or disposable. In reference to the electrode assemblies described herein, the electrode assemblies may have a relatively long, flat body (e.g., an elongate body) and may have a length that is greater than a few inches long (e.g., greater than 2 inches, greater than 3 inches, greater than 4 inches, greater than 5 inches, e.g., from a first region of electrical contact to the next nearest region of electrical contact). In some variations, the two electrodes of the apparatus are near each other in order to target a more spatially restricted area.

Described herein are electrode apparatuses for use with an electrical stimulator to be worn on a subject's head. The electrode apparatuses described herein are generally elongated, thin bodies that include a first active region for applying electrical energy to a subject's skin at or near one end region, and a second active region for applying electrical energy to another region of a subject's skin at or near a second end region. The first and second active regions on the body may be connected by an elongated portion that is typically greater than two inches long. In some variations the elongate body is stiff or relatively rigid (though it may be ductile or include a ductile region that can be bent to set a shape). In some variations the elongate body has a limited flexibility, e.g., so that it is flexible in a first axis (e.g., an x-axis) but is not flexible in a second axis (e.g., y-axis), and may be rotated. For example, the elongate body of the electrode apparatus may be formed of a sheet of material such as a flex circuit material.

As used herein, when a component is described as being at an end region of another component, it should be understood that the first component is not limited to being at the extreme end of other component, but may be adjacent to or near the absolute end or edge of the other component. For example, the first component may be within 20% or less of the total length of the other component from an edge or absolute end of the other component. In contrast, when a component is described as being at the end or edge of another component, the first component may be at or immediately adjacent to the absolute end or edge of the other component.

For example, an electrode apparatus may include: a first electrode portion having a front side and a back side; a first active region on the front side that is configured to deliver energy to the subject's skin; a second electrode portion separated from the first electrode portion by an elongate body region extending at least two inches between the first electrode portion and the second electrode portion; and a second active region on a front side of the second electrode portion that is in electrical communication with the second connector and is configured to deliver energy to the subject's skin. Although the integrated electrode strips described herein that include TES control circuitry integrated with the flexible electrode strip may not include connectors to connect to additional TES control devices, in some variations additional connectors are included. For example, an electrode device may include a first connector extending proud from the back side, wherein the first connector is in electrical communication with the first active region; a second connector extending proud from the back side, wherein the first and second connectors are separated by a predetermined (or in some variations, adjustable) distance, e.g., between about 0.7 and about 0.8 inches from center to center.

As used herein, an electrode portion may refer to a region of the electrode assembly that includes, on one surface, an electrically active region that is, for example, configured as a cathodic or anodic region, and may also include surrounding non-electrically active regions including, for example, adhesive for holding the electrically active region to the skin of the user. The electrically active region may include multiple sub-regions that may be electrically activated together or as sub-sets, as described in detail below. An electrode portion may also include a surface that is opposite from the surface with the electrically active region. Other electrode portions may not include contacts, but may be connected (e.g., by electrical trace(s)) to contacts that are present at other locations on the electrode assembly. An electrode portion may be a sub-region of the substrate forming the electrode assembly, for example, at an end region of the substrate. In some variations the electrode portion is a discrete region of the electrode assembly (which may include two or more such electrode portions). The first active region of the first electrode portion may be positioned off-center on the first electrode portion.

As mentioned above, the elongate body region between the first and second electrode portions (and the first and second active regions) may be flexible in a first direction but not flexible in a direction normal to the first direction. For example, the elongate body region may be formed of a flex circuit material. Examples of flex circuit materials are well known, including, for example, polymers such as polyester (PET), polyimide (PI), polyethylene napthalate (PEN), Polyetherimide (PEI), various fluropolymers (FEP) and copolymers.

In general, the electrode apparatus may be substantially flat. For example, the thickness of the electrode apparatus may have an overall thickness (e.g., thickness of the substrate, and layers printed, silk-screened, soldered, or otherwise adhered onto the substrate) that is less than 5 mm, less than 4 mm, less than 3 mm, less than 1 mm, less than 0.9 mm, less than 0.8 mm, less than 0.7 mm, less than 0.6 mm, etc., and extend in a plane (that may be bent or curved). The connectors may extend proud of this overall thickness. In addition, the electrode portions may extend above/below this overall thickness.

In any of the variations described herein the electrode apparatus may include an electrically conductive gel over the first active region and/or the second active region. The conductive gel may be adhesive and/or it may be surrounded by an additional adhesive for securing the active region to the subject's skin. For example, the electrode apparatus may include an adhesive on the front side of the first electrode portion and/or on the front side of the second electrode portion.

In some variations the electrode apparatus includes a foam region. For example, the apparatus may include a foam on the first electrode portion.

Further disclosed herein are components for controlling and outputting selected waveform sessions incorporated into the neuromodulation device. The integration of the neuromodulation device with the electrode assembly has the advantage of being less bulky and lower in profile relative to having a separate electrode assembly and neurostimulator device that connects to the electrode assembly. Having a lower profile enables the neuromodulation device to be more easily worn under eyeglasses, sunglasses, hats, and other headwear.

In this example, the neuromodulation device can contain pre-loaded waveform sessions. Having preloaded waveform sessions eliminates the need for having software and applications that are used to define or control the waveform output externally. Similarly, eliminating external control requirements for the neuromodulation device also eliminates the need for the neuromodulation device to contain a wireless (or wired, e.g. via a TES cable neurostimulator) connection.

In another example, the neuromodulation device can include a detachable tether. The tether can be a cord or a wire having a tether first end and a tether second end. The tether may contain all the neuromodulation components within its body. The tether first end can electrically connect to the neuromodulation device body, which in this example only contains the electrodes. The tether second end can connect to a telecommunication device that is able to control the waveform outputs. The tether (cord) may include current control circuitry for preparing the TES waveform to be applied by the device; optionally, the tether (as part of the current control circuitry or separate therefrom) can also include a current or power amplifier for supplying additional power when delivering the waveform stimuli to a subject and/or other electronic components (analog-to-digital converter, microprocessor, memory, digital-to-analog converter, etc.).

In yet other examples, the neuromodulation components are only partially contained within the neuromodulation device body and the remaining neuromodulation components can be placed within the tether or a component connected to a tether that connects the neuromodulation device to a telecommunication device for controlling the waveform output. Then, similar to the previous example, the tether can also include current control circuitry (e.g., an amplifier and/or other components) for providing the waveform output with appropriate intensity and other parameters.

The apparatus may generally include a thin (e.g., flat) and flexible elongate body having a front side and a back side, wherein the first electrode portion is at or near a first end region of the flexible elongate body and wherein the second flat electrode portion is at or near a second end region of the flexible elongate body and the elongate body region extends between the first and second active regions. The elongate body may be greater than two inches long (e.g., greater than 3 inches long, greater than 4 inches long, etc.). In some variations the elongate body is curved or bent (when not flexed). For example, the elongate body may have a bend in it or other out-of-plane structure or rigidity.

In some variations the elongate body region may include an electrical trace on a flexible elongate substrate. The electrical trace may be printed or otherwise applied onto (or embedded in) the substrate. For example, the trace may be flexographically printed, silk screened, or laser printed using conductive ink. The electrical trace may provide the electrical connection between the second connector and the second active region of the second electrode portion.

An electrode apparatus for use with an electrical stimulator to be worn on a subject's head may include: a flat and flexible elongate body having a front side and a back side; a first electrode portion at or near a first end region of the elongate body; a first active region on the front side of the first electrode portion, wherein the first active region is configured to deliver energy to the subject's skin; a second electrode portion at or near a second end region of the elongate body that is separated from the first electrode portion by at least two inches; and a second active region on the front side of the second electrode portion that is in electrical communication with the second connector and is configured to deliver energy to the subject's skin; wherein the first and second connectors are configured to electrically connect the apparatus to the electrical stimulator.

As mentioned above, the neuromodulation device may include an electrically conductive gel (e.g., over the first active region and/or the second active region), an adhesive on the front side of the first electrode portion and on the front side of the second electrode portion, a foam on the first flat electrode portion, or the like. In any of the electrode apparatuses described herein the first and second connectors may be separated by between about 0.6 to about 0.9 inches (e.g., about 0.7 to about 0.8 inches, about 0.72 inches, etc.).

The neuromodulation device to be worn on a subject's head may include: a flat and flexible elongate body having a front side and a back side; a first electrode portion at a first end region of the elongate body; a first active region on the front side of the first electrode portion, wherein the first active region is configured to deliver energy to the subject's skin; neuromodulation components contained within the body of the neuromodulation device; controls on the back side of the neuromodulation device (e.g., for turning on and off the neuromodulation device), controls for selecting the waveform sessions and intensity, and an indicator, such as a display or LED(s), for showing the user the status of neurostimulation by the neuromodulation device.

BRIEF DESCRIPTION OF THE DRAWINGS

FIG. 1B is a side view (end on) of the apparatus of FIG. 1A.

FIG. 2A is another example of a TES patch neurostimulator similar to the variation shown in FIG. 1A, but with the majority of the neurostimulator circuitry on a portion of the flex circuit body to be worn on the back of the user's neck, rather than the temple/forehead region.

FIG. 2B shows a side view of the apparatus of FIG. 2A.

FIG. 3A is an example of near-field communication selector to be used with a TES patch neurostimulator apparatus such as those shown in FIGS. 1A and 2A. This near-field communication selector may include waveform parameters (e.g., ensemble waveform parameters and/or instructions for selecting an ensemble waveform parameter) and other control information (e.g. a waveform intensity or frequency) to be used for operation of the TES patch neurostimulator.

FIG. 3B is a side view of the near-field communication selector of FIG. 3A.

FIG. 3C illustrates the application of the near-field communications selector onto a TES patch neurostimulator to provide control information for operating the apparatus. In this example, the near-field communication selector is adhesively secured to the TES patch neurotransmitter, enabling the function of the apparatus.

FIG. 4A is an example of a smart cable (TES cable neurostimulator) for use with an electrode assembly to be worn on a subject. The TES cable neurostimulator may connect (and receive power and control instructions) to a portable computing device such as a smartphone, and also connect directly to the connectors (e.g., snap connectors are shown) of an electrode assembly. The cable may be reused with multiple disposable (single-use or limited-use) electrode assemblies.

FIG. 4B illustrates another example of distal end of a TES cable neurostimulator having a pair of connectors that may be independently connected to an electrode assembly.

FIG. 6A illustrates an intermediate apparatus (system) including a TES neurostimulator cable and TES neurostimulator patch, in which the neurostimulator patch is somewhat simplified compared to the variation shown in FIGS. 1A-3C, and the cable provides power (and/or control information) to the patch.

FIG. 6B illustrates another variation of an intermediate apparatus similar to that shown in FIG. 6A, but with the cable connecting to circuitry on a region of the electrode assembly configured to be worn on the back of the user's head.

FIG. 7A is a perspective view of a first variation of an electrode apparatus as described herein.

FIGS. 7B, 7C and 7D show front, top and back views, respectively, of the electrode assembly of FIG. 7A.

FIG. 8A is an exploded view of the front of the electrode assembly similar to that shown in FIG. 7B.

FIG. 8B is an exploded view of the back of the electrode assembly similar to that shown in FIG. 7D.

FIG. 9 is an alternative front view of an electrode assembly similar to the apparatus shown in FIG. 7B, in which a foam pad is not included over the front of the first electrode region.

FIGS. 13A-13D show perspective, front, side, and back views, respectively, of another variation of an electrode assembly.

FIGS. 14A-14C show perspective, front, and back views, respectively, of another variation of an electrode assembly.

FIG. 18A is a top view showing traces connecting through the substrate (shown in FIG. 18B) to multiple sub-regions forming an active region of the electrode on the bottom surface, shown in FIG. 18C.

FIG. 22A is a front perspective view, and FIG. 22B is a back view.

FIGS. 23A and 23B illustrate another variation of a cantilevered electrode assembly similar to the one shown in FIGS. 10A-10C and 10D, in which the two electrode skin-contacting portions (connected by the flexible elongate body region) are oriented differently than shown in FIGS. 10A-10C; the active regions of the electrode skin-contacting portions extend from edge-to-edge of a central region of both electrode skin-contacting portions. FIG. 23A is a front perspective view, and FIG. 23B is a back view.

DETAILED DESCRIPTION

Figure 1A:
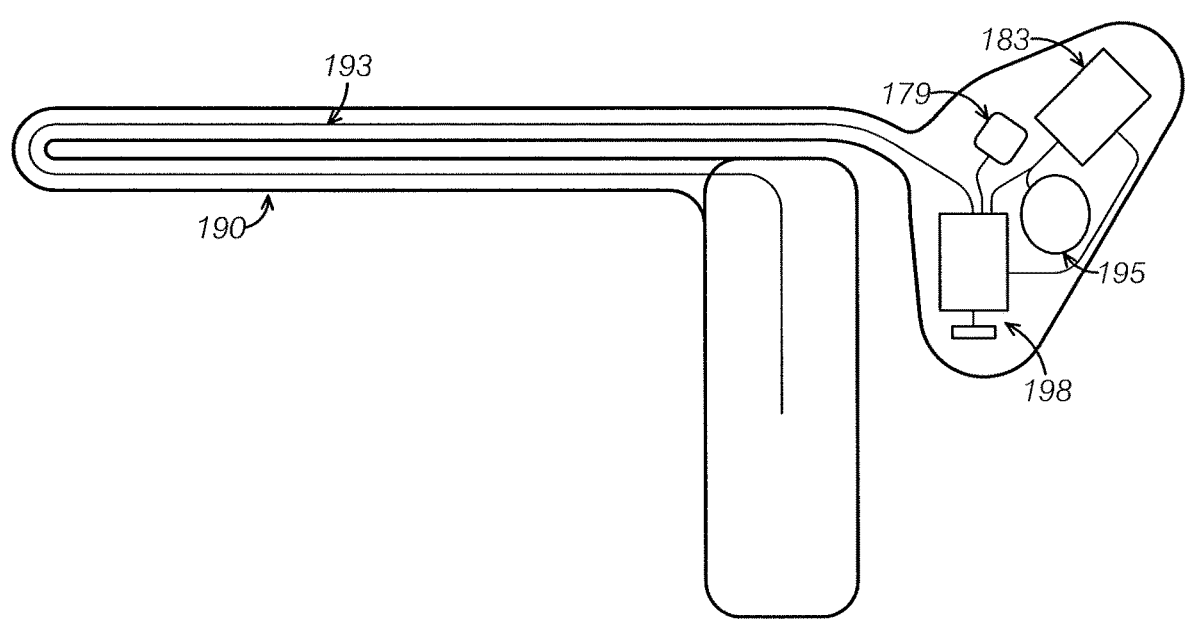
FIG. 1A is an example of a TES patch neurostimulator apparatus configured to be worn on a subject's head. The apparatus includes a pair of electrodes connected through flexible circuit body to neurostimulator circuitry (including a power source).
Figure 1C:
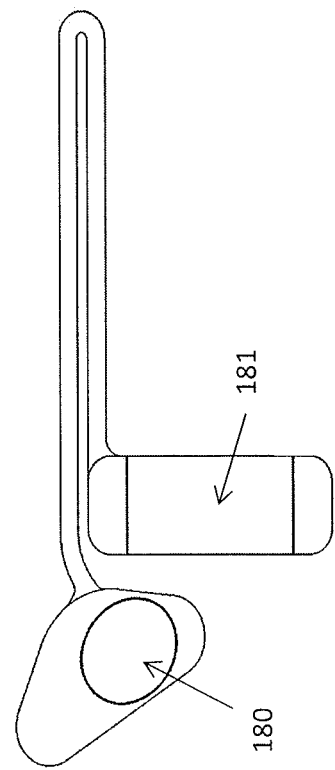
FIG. 1C is a back view of the apparatus of FIG. 1A, showing the electrode regions.

Any of the transdermal electrical stimulation (TES) apparatuses (devices and systems) may be used to modulate a subject's cognitive state, for example, to induce or enhance a state of relaxation, clarity, tranquility, calm, etc. (a "calm" state), or alternatively to induce or enhance a state of excitation, mental agility, energy, etc. (an "energy" state). All of the variations described herein typically include an electrode assembly, which may be a single piece, having a substrate with two end regions, a proximal region and a distal region, linked by a connecting region. A first electrode region (including first electrically active region) may be present at one end, while a second electrode region (including a second electrically active region) may be present at the opposite end; the connection between the two may be flexible in at least one direction. In some variations the substrate is a flexible circuit (also referred to as a flex circuit) onto which the electrode regions and other components (including conductive components) are placed. The electrode assemblies may be adhesive (e.g., may be adhesively held to the subject).

Described herein are single-use or limited-use TES apparatuses comprising flexible and wearable apparatuses with integrated TES hardware, a power source, and an electrode assembly. Such apparatuses may be referred to herein as "integrated TES apparatuses". For example, an electrode assembly may be configured as an integrated, autonomous TES neuromodulation apparatus, in which all of the control circuitry, safety circuitry, waveform generators, power sources and processors necessary for applying a TES session are integrated into the electrode assembly along with the electrically active regions. Such apparatuses may be configured for single-use or for limited-use (e.g., configured to be used between 2, 3, 4, 5, 6, 7, 8, 9, 10, 11, 12, etc. uses and 3, 4, 5, 6, 7, 8, 9, 10, 11, 12, 13, 14, 15, 20, 25, etc. uses before needing to be reconditioned, recycled or disposed of). Such apparatuses may have a user interface for a user to control the function of the apparatus (i.e. a mechanical component, touchscreen, or accelerometer-detected input (e.g. finger tap) to start or stop a waveform, increase or decrease the intensity of stimulation, etc.) However, such apparatuses may not need to communicate or be controlled by a separate component. In some variations the apparatuses may include near-field communication to receive input (e.g., control input) to enable activity (turn it on), select waveforms, and control a stimulation parameter (e.g. intensity) of the waveform to be delivered. For example FIGS. 1A-3C, described below, illustrate integrated TES assemblies.

Also described herein are TES apparatuses comprising a TES cable neurostimulator that is configured to couple between a wearable (e.g. flex circuit) electrode assembly and a control device (which may be a portable electronic device such as a smartphone, tablet, smartwatch, virtual reality headset, and the like); the TES cable neurostimulator translates control information into TES waveforms that are applied by the electrode assembly. In a simplest form, the electrode assembly is simplified so that it does not include any of the control circuitry to generate and deliver TES waveforms; these functions may be divided between the reusable cable and the control device. For example, the control device may provide command instructions for delivering the TES waveforms as well as power to drive the TES waveforms, and the TES cable neurostimulator may receive this information (e.g., waveform parameter information or analog waveform signals) from the control device and may format the waveforms, including amplifying the signal from the control device, or forming the actual waveforms, for delivery to the simple electrode assembly. The TES cable neurostimulator may include TES circuitry to communicate with the control device, form and modulate the waveforms as instructed by the control device, and may also receive information back from the electrode assembly, including impedance measurements (e.g., indicating that the apparatus has been applied to a user) and/or electrode assembly identification information (e.g., capacitive or resistive information indicating that an electrode assembly is attached to the TES cable neurostimulator and/or what type of electrode assembly is attached, or any other information about the electrode assembly). Examples of these TES cable neurostimulator apparatuses are described below and shown in FIGS. 4A-5B, described below.

Also described herein are intermediate apparatuses, in which a TES cable neurostimulator couples between a control device such as a smartphone and an electrode assembly, but in which the control device provides both control information and power to deliver TES through the electrode assembly, while the electrode assembly may include at least some of the TES circuitry configured to form and apply the TES waveforms. FIGS. 6A-6B illustrate one example of this hybrid or intermediate apparatus, in which the TES cable neurostimulator and the electrode assembly share the TES circuitry that receives TES waveforms or waveform information from a control device (e.g., running an application software and providing a user interface), builds the TES waveforms and delivers them to a user wearing the electrode assembly in a predetermined location (e.g., on the head or head and neck).

FIGS. 1A-1D illustrate a first example of an integrated TES apparatus in which the power source (e.g., battery 195) and TES control circuitry are formed on or in the substrate 190 forming the electrode assembly. In general the TES control circuitry 198 may be any circuitry that is necessary or useful for generating and safely delivering TES waveforms to be applied between the electrodes 180, 181 (shown in profile in FIG. 1B and most visible in FIG. 1C). Examples of TES waveform parameters are described in greater detail below, and may also be found in U.S. patent application Ser. No. 14/715,476, filed on May 18, 2015 ("METHODS AND APPARATUSES FOR AMPLITUDE-MODULATED ENSEMBLE WAVEFORMS FOR NEUROSTIMULA-TION"), including ensemble waveforms formed of sequences of different component waveforms having one or more different peak current amplitudes, frequencies, percent duty cycle, percent charge imbalance, capacitive discharge periods, bursting frequency, and/or bursting duty cycle. For example, the TES control circuitry 198 may include one or more controllers (which may include or be separate from one or more processors). The TES control circuitry may include a current generator (e.g., waveform generator), which may be controlled by the processor/controller, and a memory (e.g., for storing waveform information), a skin-impedance sensing circuit (which may be incorporated into the processor), a timer, etc. The TES circuitry may also include a near-field communication circuit 183. The near-field communication circuitry 183 may be used as described below in FIGS. 3A-3C, for receiving control information and/or instructions (e.g., waveform parameter information).

The substrate may also include conductive traces 193 to connect the TES control circuitry to the electrodes.

FIG. 1B shows a side view of the apparatus of FIG. 1A. In this example, the TES control circuitry stands slightly proud of the substrate, but this is not mandatory. The circuitry may also be positioned elsewhere on the substrate (e.g., over the opposite electrode as shown in FIG. 2A, and/or distributed along the connecting region 190 between the electrodes, etc.). A cover may be used to cover and/or protect the TES control circuitry e.g. epoxy or a silicone, rubber, etc.). The cover may be a material or foam covering, etc., or the TES control circuitry may be uncovered.

Figure 1D:
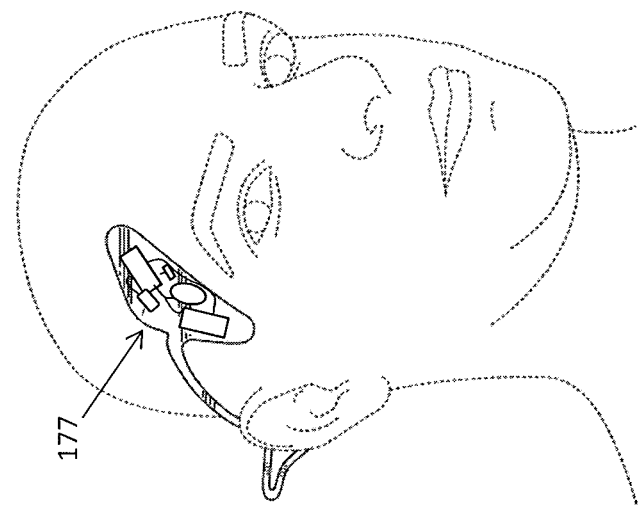
FIG. 1D is a perspective view of the TES patch neurostimulator worn on a user's head.

The exemplary substrate shown in FIGS. 1A-1D is configured to be worn on a user's head at temple/forehead region 177 and on the back of the neck (a "calm" configuration, as described in greater detail herein), although other configurations of the substrate, electrodes and integrated TES circuitry are possible. FIG. 1D shows the exemplary integrated TES apparatus of FIGS. 1A-1C worn on a user's head.

FIGS. 2A-2B illustrate another example of an integrated TES apparatus. In this example, the TES control circuitry is positioned at a different location, over the second electrode region 181; when worn, this region may be positioned on the back of the neck, and may therefore be less visible.

As mentioned, any of these apparatuses may include a power-source, such as a battery, capacitor, or the like. The power source may be of sufficient power to drive the TES stimulation for the desired duration (e.g., 10 minutes, 15 minutes, 20 minutes, 25 minutes, 30 minutes, etc.) using the TES waveforms, e.g., ensemble waveforms. Generally, apparatuses that integrate an electrode assembly and neurostimulator can operate with a small battery, in part because a wireless transmitter may be eliminated. If very small, a battery may have sufficiently low charge so that some or all safety circuitry may be excluded from the integrated neurostimulator, further reducing the size and weight of the integrated neurostimulator-electrode assembly system.

Any of the apparatuses described herein, including the integrated apparatuses shown in FIGS. 1A-2B, may include one or more controls 179 for allowing user control of their operation. For example, a power control (button, knob, etc.), intensity control (slider, dial, touchscreen, etc.), waveform selector, etc., may be incorporated onto the apparatus either with or separate from the TES control circuitry (though it will typically be connected thereto).

In any of the integrated TES apparatuses described herein, which may also be referred to as TES patch apparatuses, a TES waveform control and/or waveform selector may be used. In general a TES waveform control/selector (which may be referred to herein as a selector or waveform selector for convenience) is a separate element that can be used to provide information to the integrated apparatus, such as waveform information (selecting a particular type, duration, or intensity of TES waveform(s)), and/or control information (including unlocking the device for use). The waveform selector may communicate with the integrated device in any appropriate manner, including, for example, near-field communication. Alternatively, an onboard removable memory (e.g. microSD card) may contain waveform information that can be loaded from a user computing device or purchased pre-loaded with a waveform and other information for neurostimulator control.

FIGS. 3A-3B illustrate one example of a near-field communication selector (waveform selector) to be used with a TES patch neurostimulator apparatus such as those shown in FIGS. 1A and 2A. In this example, the near-field communication selector 300 is configured as a sticker or stamp that may be applied to the apparatus before operation, as illustrated in FIG. 3C. The patch includes an adhesive 317 and can be placed on or near a near-field communication circuit 183 forming part of the TES control circuitry. The near-field communication selector may include a coil and circuity and may encode control information (to "unlock" the device) and/or waveform information, e.g., encoding one or more ensemble waveforms for delivery to the wearer of the apparatus.

Figure 26:
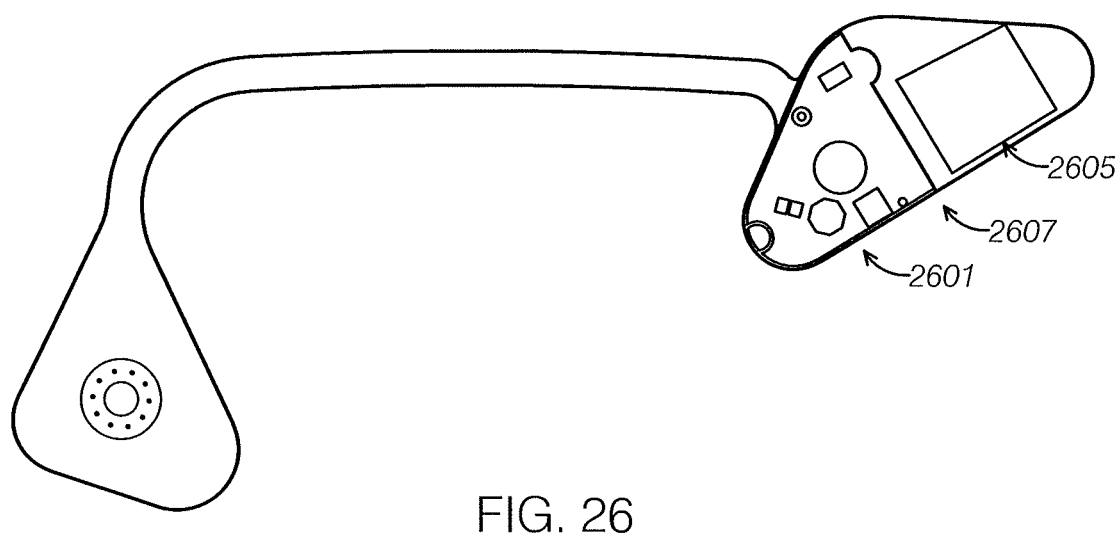
FIG. 26 is an example of a TES patch neurostimulator apparatus configured to be worn on a subject's head. The apparatus includes a pair of electrodes (not visible) connected through a flexible circuit body to a neurostimulator circuitry including a power source.

FIGS. 26-29 illustrate examples of integrated TES apparatuses in which the power source and TES control circuitry are formed on or in the substrate forming the electrode assembly, similar to those shown in FIGS. 1A-3B above. For example, FIG. 26 shows the back of one exemplary device in which the flexible, electrode assembly is lightweight (e.g., has a weight of less than 9 grams). The electrodes (not visible) are on the front side; the assembly is adapted to be worn over the user's temple region and behind an ear. A separate attachment (e.g., snap, pin, etc.) to an additional piece is not necessary. In this example, there is space 2607 between the circuitry 2601 (e.g., controller, signal generator, etc.) and the battery 2605, which may allow some level of bending or flexing to better conform to anatomy. The circuitry may create a relatively stiffer region. The total thickness is approximately 5.5 mm.

Figure 27A:
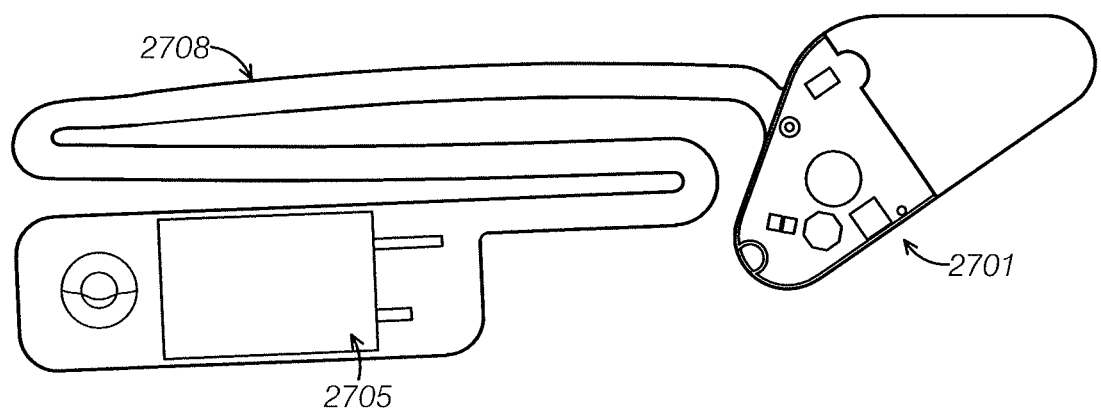
FIG. 27A is another example of a TES patch neurostimulator apparatus in which the neurostimulator circuitry is present on one end of the flexible substrate that also forms the electrodes, while the battery is another end.
Figure 27B:
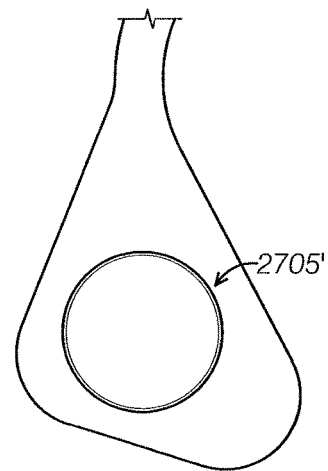
FIG. 27B illustrates a battery attached to one end of a flexible substrate forming the TES patch electrode.

FIGS. 27A-27B illustrate another variation of an integrated TES apparatus, configured to be worn on the wearer's (user's) forehead/temple and the back of the wearer's neck. In this example, the battery 2705 is separated from the majority of the neurostimulator circuitry 2701 by the more than the two inch long path of flexible substrate 2708 connecting the two electrodes (not visible). This may make the battery less visible, and may also help the apparatus conform better to the anatomy, as the larger battery may be attached at only one point. FIG. 27A illustrates a variation in which the second electrode portion is rather large and rectangular (e.g., having a length of more than 17 mm in this example). FIG. 27B illustrates the second electrode portion in another configuration of an integrated TES apparatus in which the second electrode portion is smaller and includes a battery 1705' having a round profile.

Figure 28:
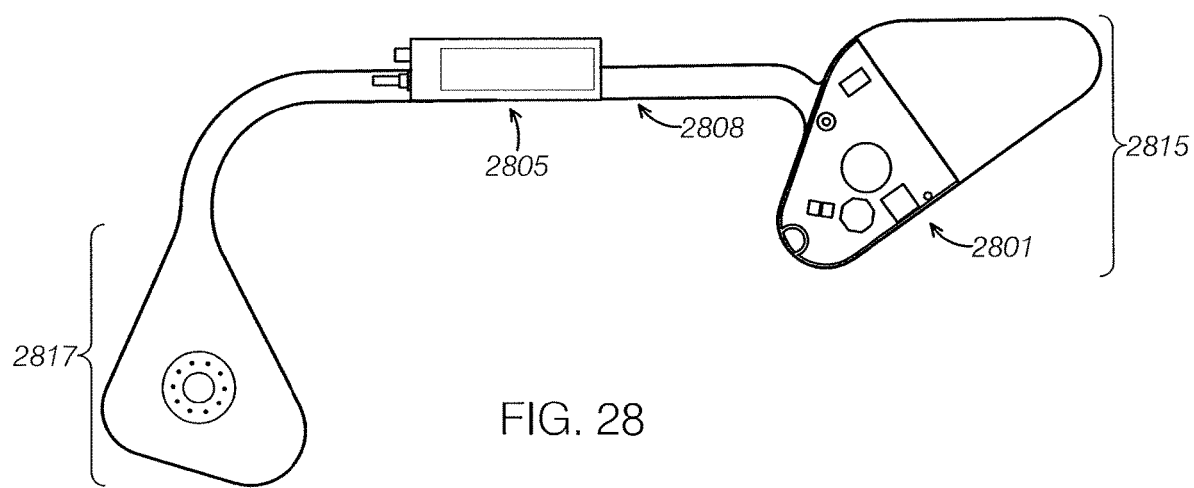
FIG. 28 illustrates an example in which the battery is located at an intermediate region between the two ends supporting the electrodes, configured to be positioned behind the wearer's ear when worn.

FIG. 28 is another example of an integrated TES apparatus in which the battery is positioned in an intermediate position between the somewhat enlarged first and second electrode portions. The circuitry 2801 is integrated on the flexible substrate on the back of the first electrode portion, while the battery 2805 is positioned along the connecting region 2808 between the first electrode portion 2815 and the second electrode portion 2817, and is configured so that it will be held above the wearer's ear when the device is worn with the first electrode region attached to the temple and the second electrode region behind the back of the ear (e.g., at or near the mastoid). This position may feel particularly balanced as it conforms well to the wearer's anatomy, while allowing a fairly long-lasting battery.

Figure 29:
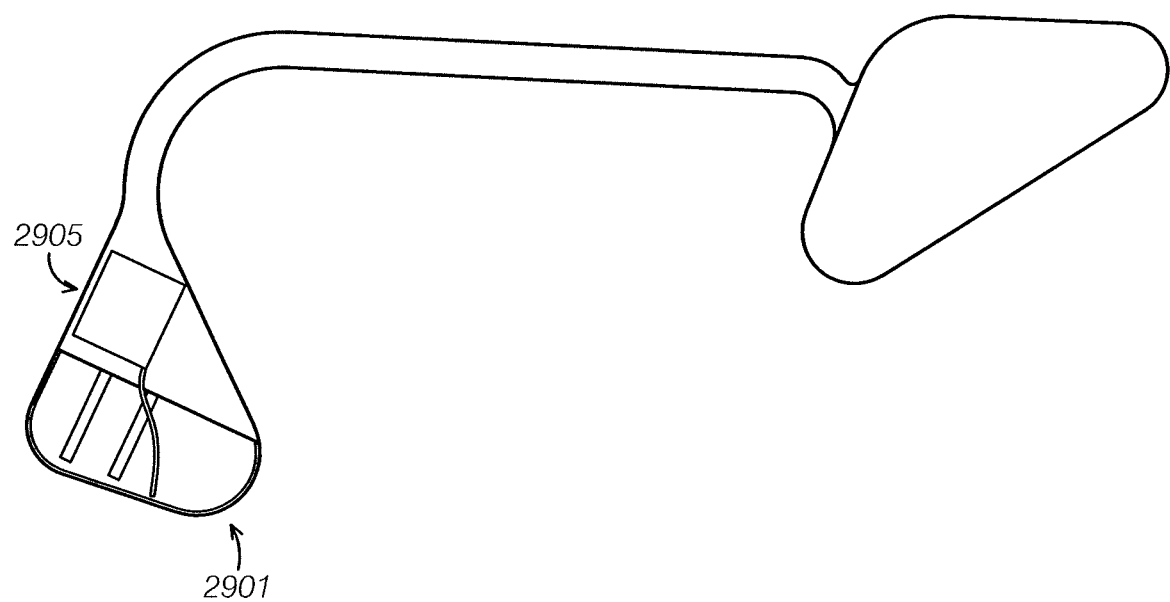
FIG. 29 illustrates another example of a TES patch neurostimulator apparatus in which the battery and neurostimulator circuitry are all located on one of the electrodes (e.g., to be worn behind the wearer's ear).

FIG. 29 illustrates another example in which all of the circuitry and battery 2901, 2905 are coupled to the second electrode region of the flexible substrate. In this example, the entire apparatus may weigh between 5-10 grams (e.g., 6.5 grams) and the majority of the weight is supported behind the user's ear, near the mastoid region. The electrode may be held against the skin by an appropriate skin adhesive. Although the addition of the circuitry and battery to the second electrode portion may make the otherwise highly flexible substrate more rigid, particularly if an additional printed circuit board (PCB) is used, this additional rigidity in this limited region may not be problematic, given the flexibility of the rest of the apparatus. In addition, the total PCB space used (as in this example) may be relatively small (e.g., less than approximately 2.5 $cm^2$). In the exemplary apparatus shown in FIG. 29, the battery is 90 mAh and approximately 6.5 mm thick, including the flexible substrate, but may provide sufficient power for at least 3 to 4 energy waveforms (i.e. tens of minutes of TES). The front (first electrode portion) may feel particularly comfortable, as it allows excellent compliance with the anatomy.

Other variations of TES neurostimulation apparatuses that are not integrated, but may include external power and/or control are also described herein, as mentioned above. For example, FIGS. 4A-5B illustrate variations of a TES apparatus in which the electrode assembly is formed on a flexible material, but include one or more connectors (e.g., U.S. patent application Ser. No. 14/634,664, filed on Feb. 27, 2015, and titled "CANTILEVER ELECTRODES FOR TRANSDERMAL AND TRANSCRANIAL STIMULATION") such as snap connectors or other mechanical and electrical connectors that may be connected to a cable, and (through the cable) to a hand-held or otherwise portable computing device, such as a general-purpose smartphone (e.g., iPhone™, Android™, Google phone) or other portable or wearable electronics. The portable computing device may function by running software and/or firmware for controlling operation of the TES neurostimulator, including in some variations, selecting and preparing the TES waveforms to be delivered, confirming connection of the electrode assembly to the user, and/or confirming the type/state of the electrode apparatus. Although the electrode apparatus may be single-use or limited-use, and may include no or very little of the TES control circuitry (unlike the variation shown in FIGS. 1A-3C), the cable 499 may be configured as a "smart" cable, which includes TES control circuitry receiving power and control information from the portable computing device (control device) and forming the TES waveform for delivery by the electrode assembly. The smart cable may also be referred to herein as a TES cable neurostimulator, and it may include all or some of the TES control circuity described above, e.g., current control circuitry, including at least amplification circuitry for amplifying the power provided by the control device to the TES waveforms.

In FIG. 4A, the TES cable neurostimulator 499 is configured to plug into the control device 490, so that it may drive delivery of TES waveforms appropriate for the type of electrode assembly (e.g., calm 485 or energy 486). In any of the apparatuses described herein, the apparatus may detect the type of electrode apparatus and provide or allow only waveforms appropriate for this type of electrode (e.g., to elicit a calm and/or energy state). In FIG. 4A, the proximal end of the TES cable neurostimulator includes a housing region which may house some of the TES control circuitry as well as forming the connector (e.g., a "Lightning" type connector when connecting to an appropriate iPhone). The distal end of the TES cable neurostimulator may include a set of connectors (e.g., snap connectors, magnetic connectors, multi-pin connectors, concentric connectors, etc.) complimentary to the connectors on the electrode assembly. In FIG. 4A the connectors are held in a fixed spacing appropriate to mate with the mechanical/electrical connectors on the electrode assembly. FIG. 4B shows another example of the distal end region of an apparatus in which the connectors are separately positionable relative to each other. In other variations of the TES cable neurostimulator, a larger housing containing TES control circuitry may be present at or near the distal end of the cable (i.e., near the electrode assembly) or in-line along the cable, similar to how music controls may be present along the cable of earbuds.

Figure 4C:
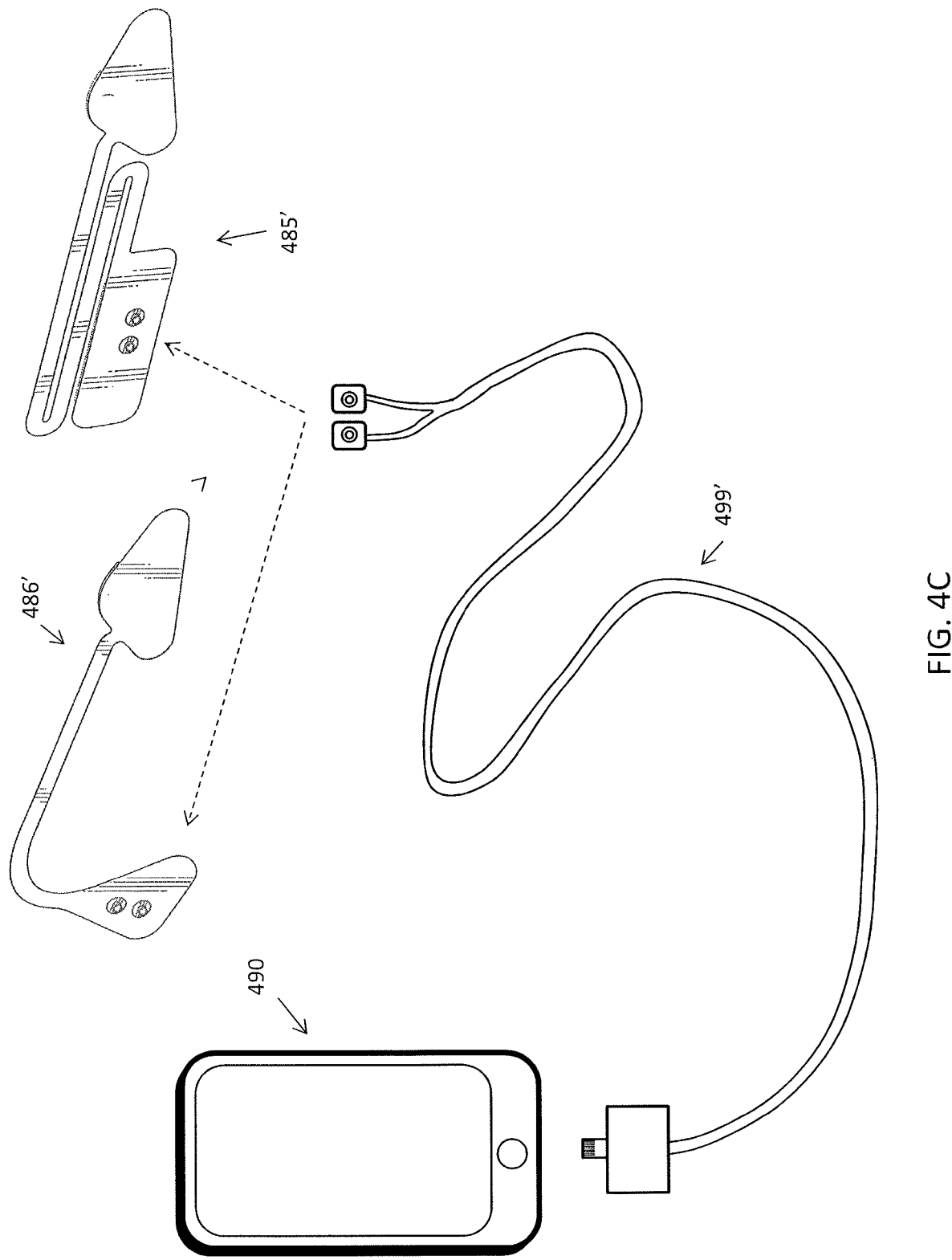
FIG. 4C illustrates another example of a TES cable neurostimulator connecting to another pair of electrode assemblies having connectors on a region of the electrode assembly that is configured to be worn on the back of the user's head, e.g., on the neck or mastoid region, rather than the temple/forehead region as in FIG. 4A.
Figure 5B:
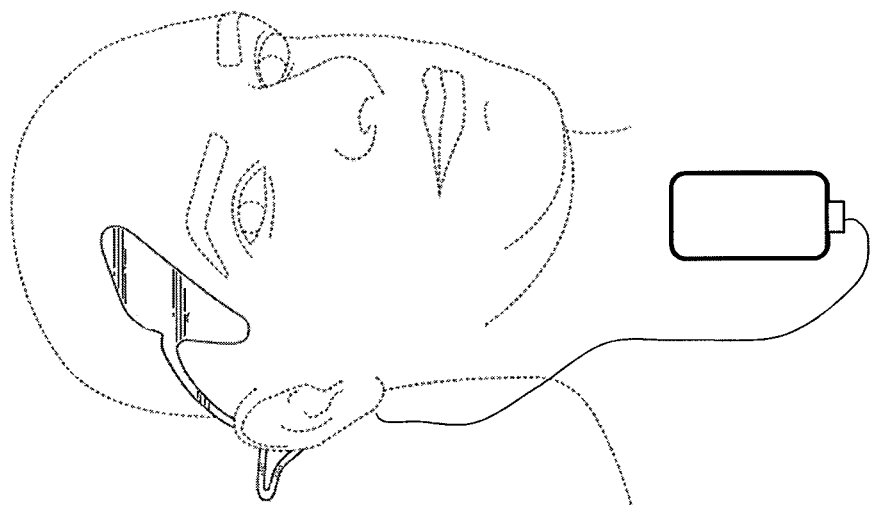
FIG. 5B illustrates connection of a TES cable neurostimulator to a smartphone and an electrode assembly similar to that shown in FIG. 4C.
Figure 5A:
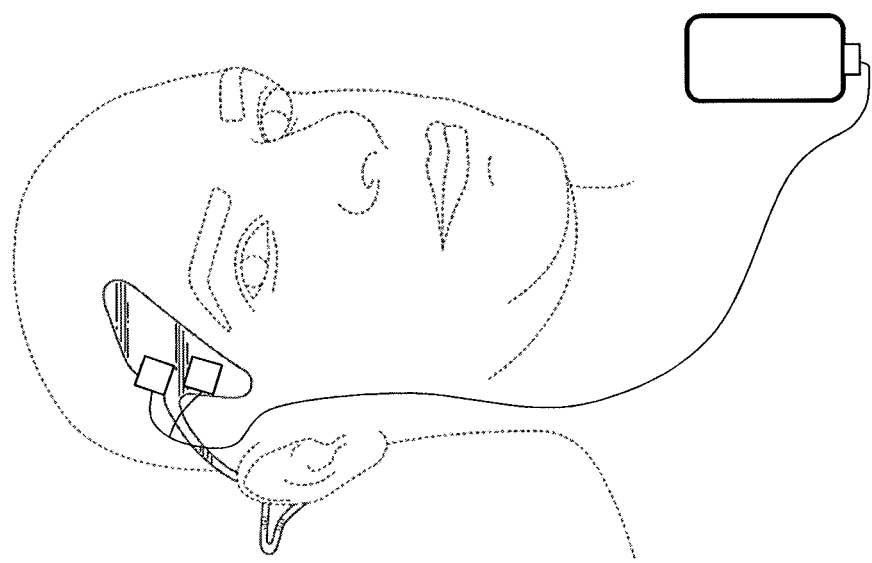
FIG. 5A illustrates connection of a TES cable neurostimulator to both a smartphone and an electrode assembly on a user, similar to the variation shown in FIG. 4A.

FIG. 4C illustrates an alternative view of a TES cable neurostimulator 499' connectable to two alternative configurations of electrode assemblies 485', 486'. In this example, the TES cable neurostimulator is configured to be connected to a region of the electrode assembly that is worn away from the face (e.g., on the back of the neck and/or behind the ear). This is illustrated in FIG. 5B. For comparison, a system such as that shown in FIGS. 4A-4B is illustrated worn on a user in FIG. 5A.

As shown in FIGS. 6A and 6B, in some variations the TES circuitry may be distributed between the TES cable neurostimulator 699 and the electrode assembly 693, 693'. In FIG. 6A, at least some of the TES control circuitry is present on the electrode assembly 693, so that power and control information from the control device (e.g., phone 688) is passed on to the circuitry on the electrode assembly. In some variations some of the circuitry may be on the TES cable neurostimulator, though in some variations, the cable may merely include connectors at the distal end to connect to the electrode assembly which may include the TES control circuitry, while the proximal end of the TES cable neurostimulator may include a connector appropriate to connect to the control device (e.g., smartphone 688), while the rest of the cable includes a conductive path to communicate between the two.

In general in any of the TES neurostimulators (including wired and wireless stimulators), when a control device such as a phone communicates with TES control circuitry to apply a TES waveform, the communication may be digital, analog, or a combination of analog and digital. In some variations, as described in U.S. application Ser. No. 14/639,015 previously incorporated by reference, the TES waveform information may be digital and discrete, so that the communicated TES information is divided up into waveform parameters that are interpreted by the TES control circuitry (including processor) to form the actual waveforms to be delivered. However, in some variations it may be beneficial to provide actual analog and/or digitized TES waveforms, similar to how the waveform of an audible signal, e.g. song, is encoded. This may be particularly useful in the wired configurations shown in FIGS. 4A-6B; the TES circuitry may then modulate (e.g., amplify, limit, etc.) the applied TES waveforms. Alternatively or additionally, the system may be configured to transmit from the control device (e.g., smartphone) an analog waveform signal that is modulated by a second signal from the control device (which may be digital or analog) to form the final TES waveform. For example, an analog signal may be modulated by a defined set of amplitude modulation parameters, defining the addition/removal of capacitive discharge currents, etc. Alternatively, a digital signal on a second channel may be present on the cable that defines the presence of a capacitive discharge current at a particular timepoint in the waveform.

EXAMPLES

In general, described herein are neuromodulation devices having an integrated electrode and neuromodulation unit, systems including them, and methods of wearing and using them for delivering neurostimulation to a subject. The described integrated neuromodulation device will largely contain disposable or semi-disposable components that may be entirely or partially recyclable. It is conceptualized that the integrated neurostimulation device can be geared toward a more disposable device that a person can use for a certain number of sessions before requiring replacing the integrated neuromodulation device. Thus, multiple layers of adhesive may be present on portions of the electrode assembly, such that they may be peeled before a subsequent use to reveal a fresh adhesive area (similar to how a layer of a lint roller is removed to reveal a new, fresh adhesive patch).

The integration of the electrode assembly and the neuromodulation control components has many benefits. For one, having the entire neuromodulation device on a strip means a much more portable and lighter weight device compared to related designs. In related designs, having a detachable neuromodulation unit meant that having proper electrical contact was always a concern. The issue of proper electrical contact is eliminated, because the electrodes and the neuromodulation components are in electrical communication internally within the neuromodulation device strip.

A neuromodulation system as described herein may be an integrated system that combines two main features of related neuromodulation systems. More specifically, these devices may combine and integrate previously described lightweight, wearable neurostimulator devices that were configured to couple to a consumable, disposable electrode assembly. The present disclosure is directed to neuromodulation output-generating components combined with a plurality of electrodes that are all located on a flex circuit strip or having a strip-like shape.

In one embodiment, all the components (including but not limited to electrodes, neuromodulation components, controls for powering on and off the device, and controls for selecting a particular waveform session) associated with the neuromodulation device strip are integrated into an integrated flex circuit device. There are numerous advantages of integrating the neuromodulation components with the electrode within one unit. For one, having an overall lighter weight device attached to one's facial and neck region is more comfortable and less intrusive for the wearer. Also, having even a slightly lighter neuromodulation device strip enables the use of weaker adhesives (and/or smaller adhesive areas), improving usability while reducing cost and the likelihood of skin irritation. Using weaker adhesives is less damaging to the user's skin. Along the same vein, because all the components for controlling the neurostimulation output are integrated into the device strip, there is no requirement that the neuromodulation device strip contains means for wireless connections (i.e. Bluetooth capabilities). There would also be no requirements for a corresponding smartphone mobile application for controlling the waveform sessions. Another very relevant advantage for both a manufacturer and a potential consumer is that the neuromodulation device strip with integrated components would be more cost effective to manufacture and produce and as a result can be brought to consumers at a price an order of magnitude cheaper than other versions.

Similar to related designs, the electrode assembly may have a variety of shapes and be formed on a flexible material, such as flex circuit material, and in electronic communication with the neuromodulation components that are also located on the flexible circuit strip. In general, the flexible circuits described herein are amenable to high throughput automated pick and place manufacture using surface mount technology. In one possible embodiment, the neuromodulation device may include a number of pre-loaded waveforms or "vibe" sessions. A user simply has to turn on the neuromodulation device and select the desired waveform. In some embodiments, a wireless or wired connection may be established between the neuromodulation device and a mobile telecommunication device. For example, it would be possible for the mobile telecommunication device to include downloadable software, firmware, or applications aimed at controlling and delivering an assortment of waveform sessions and wirelessly or in a wired configuration transmit to the integrated neuromodulation device commands for operating said device. Further, it would also be possible in this current example for the mobile telecommunication device to receive output from the integrated neuromodulation device such as a physiological parameter. In general, the flex circuit may include sensors (e.g. electrodes for recording EEG, EMG, EOG; temperature sensors; heart rate sensors; accelerometers and gyroscopes; etc.) and may, in variations using a TES cable neurostimulator, may transmit this information to the user computing control device (i.e. smartphone).

In general, the neuromodulation device strip is flexible. All the electronic components contained within the flexible strip are formed in a manner that allows for some degree of flexibility and movement. Flexibility may permit bending up or down along the longitudinal axis of the device strip as well as allow for a some twisting of the strip. The neuromodulation device strip may also have flexibility about its horizontal axis. Flexibility of the neuromodulation device strip along both its longitudinal and horizontal axes allows for movements associated with the user placing the neuromodulation device strip on his head and neck region as well as allowing for natural movements of the user's head and neck during use of the neuromodulation device strip with a lower likelihood that all or part of the dermal electrode will dislodge from a low-impedance contact with the skin.

The neuromodulation devices described herein may incorporate some or all of the components needed for controlling and outputting the transdermal electrical stimuli. The incorporation of all the requisite components for the neuromodulation device eliminates the need for a separate neuromodulation applicator and the drawbacks of maintaining electrical connection between the neuromodulation applicator and the electrode assembly.

In the example where some of the neuromodulation components are contained within the neuromodulation device, an external tether can contain the remaining neuromodulation components. The tether can contain a means for amplifying the neuromodulation output or a chip for contributing to the control or output of the waveform sessions. The tether can also be connected to a telecommunication device (e.g. a smartphone, a tablet, a laptop, a smartwatch, a virtual reality headset, or a computer). In this latter scenario, the telecommunication device can include software, firmware, or applications for controlling or modulating the waveform session outputs.

In reference to FIGS. 7A-7D, an electrode assembly is shown. In this example, the electrode assembly 100 includes a plurality of electrode portions (two are shown) 103, 105. In FIG. 7A, a front perspective view is shown. The front side is the side that will face away from the subject when worn. The electrode assembly is thin, so that the electrode portions include a front side (visible in FIGS. 7A and 7B) and a back side (visible in FIG. 7D). As shown in the side view of FIG. 7C, the device has a thin body that includes the electrode portions 103, 105 as well as an elongate body region 107 extending between the two electrode portions. The elongate body is also thin (having a much larger diameter and height than thickness). The thickness is shown in FIG. 7C.

FIG. 7D shows a back view of this first example of an electrode assembly. In this example, the first 103 and second 105 electrode portions are also shown and include active regions 133, 135. The active regions are bordered by adhesive 140. The first 103 electrode portion includes, on the back (patient-contacting) side, a first active region 133, surrounded by an adhesive material 140 that extends. The active region may include a conductive material (e.g., electrically conductive gel). Similarly, the back of the second electrode portion 105 includes the second active region 135 which is bounded, e.g., around its entire circumference, or at least on, by an adhesive 140. The adhesive may be any biocompatible adhesive that can releasably hold the material to the skin.

In FIG. 8A, the front side of the electrode assembly is shown with the foam backing 121, 123 (which may be adhesive on one or both sides) materials. A foam backing material is advantageous for apparatuses that incorporate TES components on the front side of the electrode assembly, because it can protect these components from short-circuiting (i.e. via touching to a conductive surface, moisture, etc.). The base may be composed of a flex circuit material, e.g., that is relatively insulating, flexible out of the plane of the material, and rigid in the plane (meaning it can be bent up/down out of the plane, but has rigidity when pushed/pulled in the direction of the plane of the material). The flex circuit may have a dielectric layer covering all or part of the front and/or back side, covering and insulating conductive traces. Many of the structures used to form the electrode regions and connectors may be printed directly onto the base or attached to the base (e.g. by flexographic printing, silk screening, or laser printing with conductive ink). As described above, the foam material over either or both of the front sides of the first and second electrode portions may be omitted (or replaced with another electrically insulating material such as epoxy).

Electrode assemblies are generally described in detail below, along with specific examples and variations. In particular, described herein are electrode assemblies that are thin (e.g., generally less than 10 mm, less than 9 mm, less than 8 mm, less than 7 mm, less than 6 mm, less than 5 mm, less than 4 mm, less than 3 mm, less than 2 mm, less than 1 mm, etc. thick, which may not include the thickness of the connectors that may extend proud from the thin electrode assembly), and flexible, and may be flat (e.g., formed in a plane). For example, they may be printed on a flex material, such as the material used to print a flex circuit. In use, they can be wrapped around the head to contact it in at least two locations (e.g. at the temple and the back of the neck and/or behind the ear). In some examples, one snap connects to a first active electrode region (anodic or cathodic region) that is surrounded by an adhesive to adhere the active region to the user's head. A second electrode region (anodic or cathodic) on a separate part of the electrode assembly may be electrically connected to the other connector. For example, the second electrode region may be adapted to fit either on the region over the mastoid bone, behind the subject's ear (energy electrode configuration) or a region across the user's neck at the base of the hairline, e.g., near the midline of the neck (calm electrode configuration). Other electrode locations on the head, neck, or other parts of the body below the neck are possible by adjusting the shape of the flex circuit and position of the electrode areas.

The electrode apparatus may be printed (e.g., by flexographic printing, laser printing with conductive ink, silk-screening, etc.) on a flexible plastic substrate (flex substrate). The electrode active regions on a first side of the assembly may include a layer of conductor (e.g., silver), over which a layer of Ag/AgCl is deposited that is sacrificial and acts as a pH buffer. A next layer of hydrogel overlays the Ag/AgCl electrode so that it can uniformly transfer charge across the active region into the skin. A portion of the electrode assembly around the active electrode area may have an adhesive that permits good contact with a user's skin. The electrodes conceived generally have the active region on a first side that is adapted to contact the user's skin. The active region may include a hydrogel that transfers energy (e.g. current) from the neuromodulation device to the subject's skin. The active region of the electrodes is in electrical communication with the neuromodulation components on the neuromodulation device strip.

Both the first electrode portion and the second electrode portion may be adhesively held with the electrically active regions against the skin, allowing the neurostimulator to apply energy, and in particular the waveforms as described in U.S. patent application Ser. No. 14/320,443, titled "TRANSDERMAL ELECTRICAL STIMULATION METHODS FOR MODIFYING OR INDUCING COGNITIVE STATE," filed on Jun. 30, 2014, Publication No. US-2015-0005840-A1 and herein incorporated by reference in its entirety.

Another example of an electrode assembly similar to the variation shown in FIGS. 7A-9 is shown in FIGS. 13A-13D. In this example, the electrode assembly 1300 includes two electrode portions 1303, 1305 each having at least one active region 1333, 1335. FIG. 13A shows a front perspective view, FIG. 13B is a front view, FIG. 13C is a side view and FIG. 13D is a back view. The front side is the side that will face away from the subject when worn. Electrode portions 1303, 1305 are connected by an elongate body region 1307 extending between the two electrode portions. The elongate body is also thin (having a much larger diameter and height than thickness). The thickness is apparent in FIG. 13C. None of the figures herein are to scale, unless indicated otherwise. The width of the connection region between two electrode regions in any of the variations described herein may be relatively small (though wider than the thickness of the electrode apparatus body region), e.g., between about 0.5 mm and 20 mm, between about 1 mm and 15 mm, between about 2 mm and 15 mm, between about 3 mm and 10 mm, etc.

FIG. 13D shows a back view in which the first 1303 and second 1305 electrode portions are also shown and include active regions 1333, 1335. The active regions are bordered by adhesive 1340. The first 1303 electrode portion includes, on the back (patient-contacting) side, a first active region 1333, surrounded by an adhesive material 1340 that surrounds the entire circumference of the active region. Adhesive regions that surround all or most of the circumference of an active region are beneficial in curved and/or hairy (e.g. with vellus hair) body regions to ensure as uniform electrical contact as possible between the active region and the subject's skin. The active region may include a conductive material (e.g., electrically conductive hydrogel). Similarly, the back of the second electrode portion 1305 includes the second active region 1335 which is bounded on an upper and lower side by an adhesive 1340. The adhesive may be any biocompatible adhesive that can releasably hold the material to the skin.

Figure 22A:
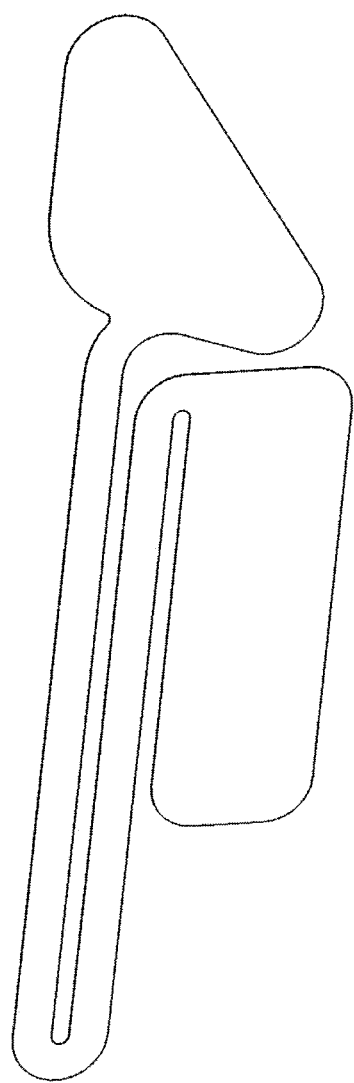
FIGS. 22A and 22B illustrate another variation of an electrode assembly similar to the one shown in FIGS. 7A-7D and 8A-9, in which the two electrode skin-contacting portions (connected by the flexible elongate body region) are oriented differently, providing a more compact profile; the active regions of the electrode skin-contacting portions extend from edge-to-edge of a central region of both electrode skin-contacting portions.
Figure 22B:
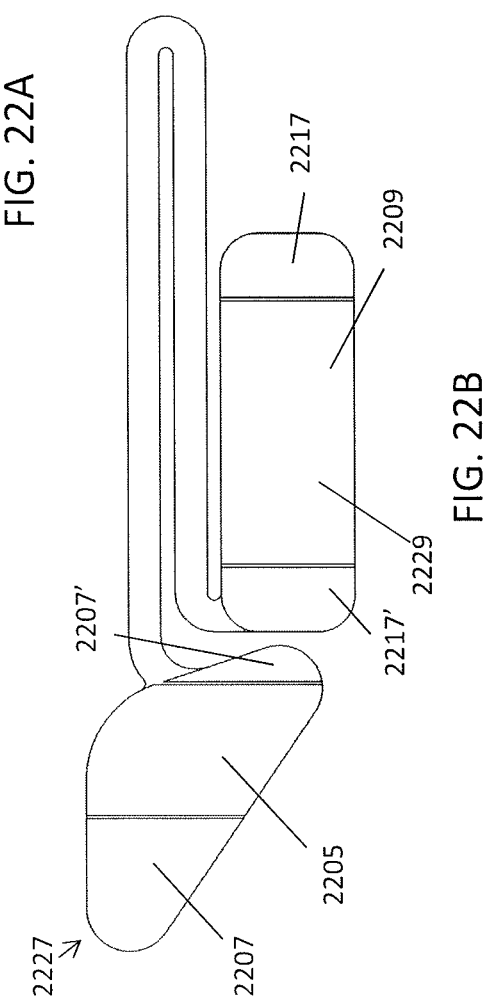

FIGS. 22A-22B illustrate another variation of an electrode assembly similar to the one shown in FIGS. 7A-7D and FIGS. 13A-13D. In this example, the second electrode region (which may be positioned on the wearer's neck, for instance) is oriented horizontally, in the direction of the elongate connecting member. This may allow the entire assembly to be more compact for packaging and manufacture. FIG. 22B shows a back view of the apparatus, including the electrically active regions 2205, 2209 which may include a conductive hydrogel. In this example, the electrically active regions 2205, 2209 may extend from edge-to-edge of the two skin-contacting electrode regions 2227, 2229, improving the efficiency and yield of manufacture. For example, the first conductive layer and/or the sacrificial layer (and any intervening layer) may comprise a portion of the area underlying the conductive hydrogel (e.g. 2205) so that the active electrode region is targeted and sized correctly while still permitting a strip of hydrogel 2205 to cover the electrode region from one end to another for improved manufacturability. This configuration may simplify the construction of the apparatus (as it may be formed without having to pick and place the hydrogel "islands" as shown in FIGS. 7D and 13D). These conductive regions are bracketed on either side by adhesive 2207, 2207' and 2217, 2217'. For example, during manufacture, parallel lanes of adhesive and hydrogel may be placed on the flex circuit without requiring a pick and place or additional die-cut step for placing a hydrogel island surrounded by an adhesive region. In the example electrode apparatus shown in FIG. 22B, manufacturing may use three lanes of adhesive with appropriate width parallel to the adjoining strips or lanes of adhesive and hydrogel on the two electrode regions 2227, 2229. For example, a first lane of adhesive having width appropriate for adhesive region 2207, a second lane of adhesive having width appropriate for the combined area of adhesive regions 2207' and 2217', and a third lane of adhesive having width appropriate for adhesive region 2217. (In another example, separate lanes of adhesive may be used for adhesive regions 2207' and 2217'.) Also during manufacture, two lanes of hydrogel of appropriate width to cover hydrogel regions 2205 and 2229 of the electrode apparatus. In some examples, a first manufacturing step places the strips of adhesive and hydrogel onto a disposable, temporary substrate so that the combined parallel strips of adhesive and hydrogel may be die cut to have the shape appropriate for the electrode regions 2227 and 2229 (including separating adhesive regions 2207' and 2217' from a single lane of material into two distinct adhesive regions for the two electrode regions), then the die cut hydrogel-adhesive regions are transferred from the temporary, disposable substrate to the electrode apparatus at the appropriate location. A beneficial feature of this design is that the electrode apparatus (and components in its manufacture) do not need to be turned, rotated, or placed and can be more readily manufactured in an efficient roll-to-roll framework.

Figure 10A:
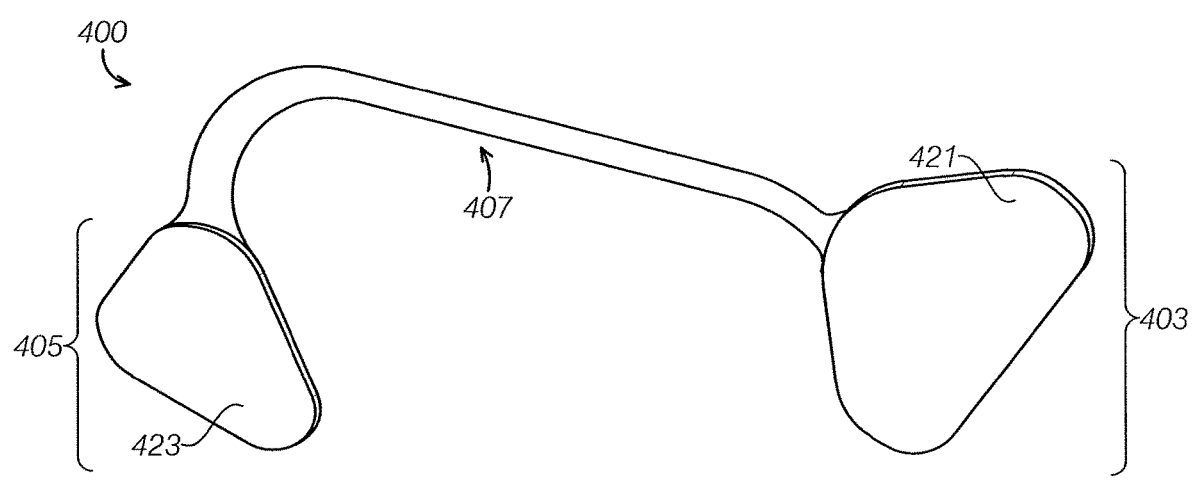
FIG. 10A is a perspective view of a variation of an electrode apparatus as described herein.
Figure 10B:
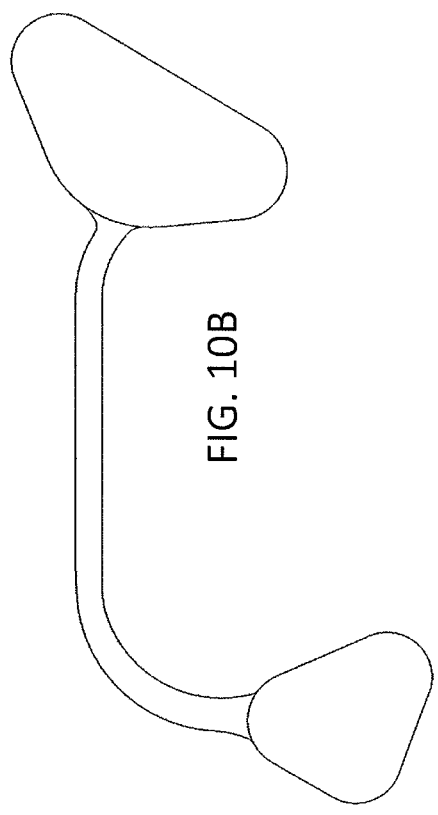
FIGS. 10B and 10C show front and back views, respectively of the electrode assembly of FIG. 10A.
Figure 10C:
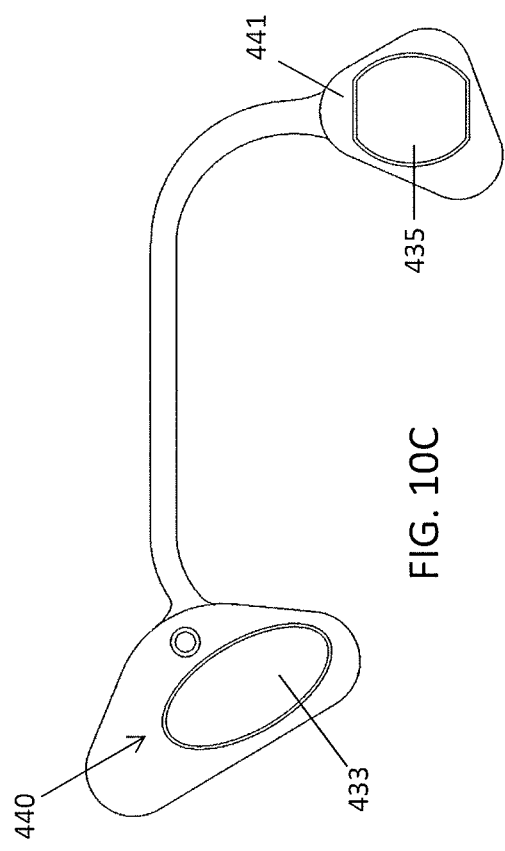

FIGS. 10A-10C illustrate another example of an electrode assembly. This example is very similar to the variation shown in FIGS. 7A-8B. In general, virtually any form factor for the electrode strips (e.g., a flexible elongate, flat electrode strip) may be used and integrated with TES control circuitry and/or power source and/or cable connection, as described herein. In the example shown in FIGS. 10A-10C, the shape of the first electrode portion 403 and foam/backing material 421 (which may also or alternatively be an adhesive material) are similar to those previously shown. An advantage of having multiple electrode apparatuses with the same shape is that they can be used interchangeably with a single neurostimulator device. However, the example shown in FIGS. 10A-10C includes a different overall shape, and may be used to connect, for example, to different regions of the patient's head/neck. In particular, the portion of the substrate forming the elongate body region 407 extending between the two electrode portions 403, 405 is shaped slightly differently. In this example, the electrode assembly may be configured to connect, for example, to the subject's temple with the first electrode portion and the elongate body region may be bent around the subject's head so that the second electrode portion may be in electrical contact with a region behind the subject's ear (e.g., at or near the mastoid). By placing the first active region 433 of the first electrode portion 405 in electrical contact with the skin at the temple region and using the adhesive material 440 surrounding the electrically active region 433 to hold the electrically active region securely in position on the subject's skin, the second electrically active region may also be adhesively 441 held to skin so that the second electrically active region 435 is in contact with the mastoid region.

Figure 10I:
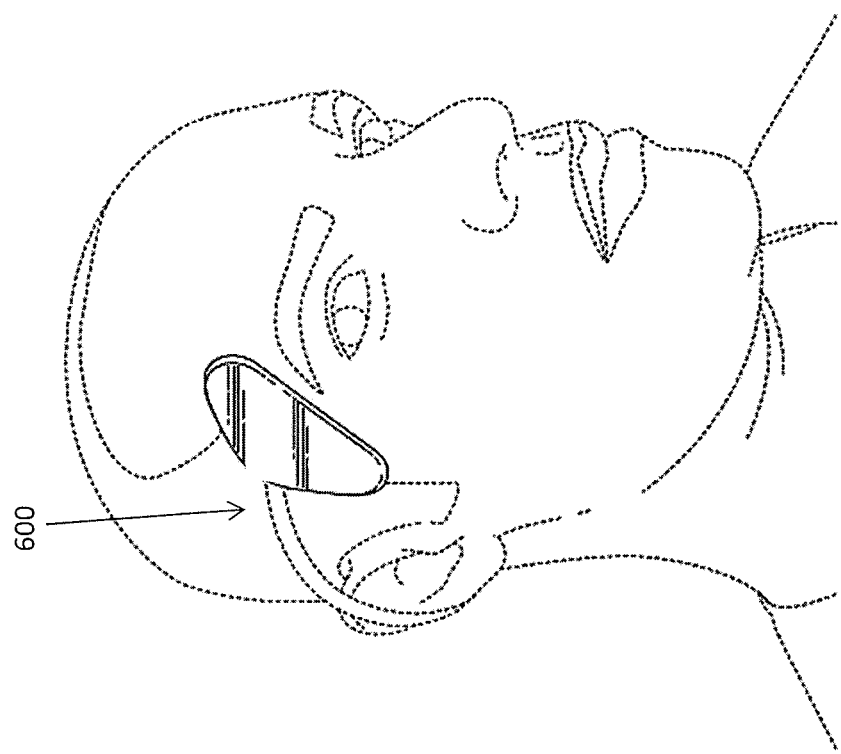
FIG. 10i illustrates an electrode assembly (similar to those shown in FIGS. 7A and 10A) worn on a subject's head.

In general the elongate body region connecting the two electrode portions may be any appropriate length, but is generally longer than a few inches (e.g., longer than about 2 inches, longer than about 3 inches, longer than about 4 inches, longer than about 5 inches, longer than about 6 inches, longer than about 7 inches, longer than about 8 inches, longer than about 9 inches, etc.). The elongate body region may also be bent or curved, as illustrated in both the variations of FIGS. 7A-9 and FIGS. 10A-10D. The bend or curve, in which the elongate body may even double back on itself, may allow the material to flex or bend to allow it to be adjustably positioned over and/or around the subject's head, as shown in FIGS. 6 and 10i, for example.

Figure 10D:
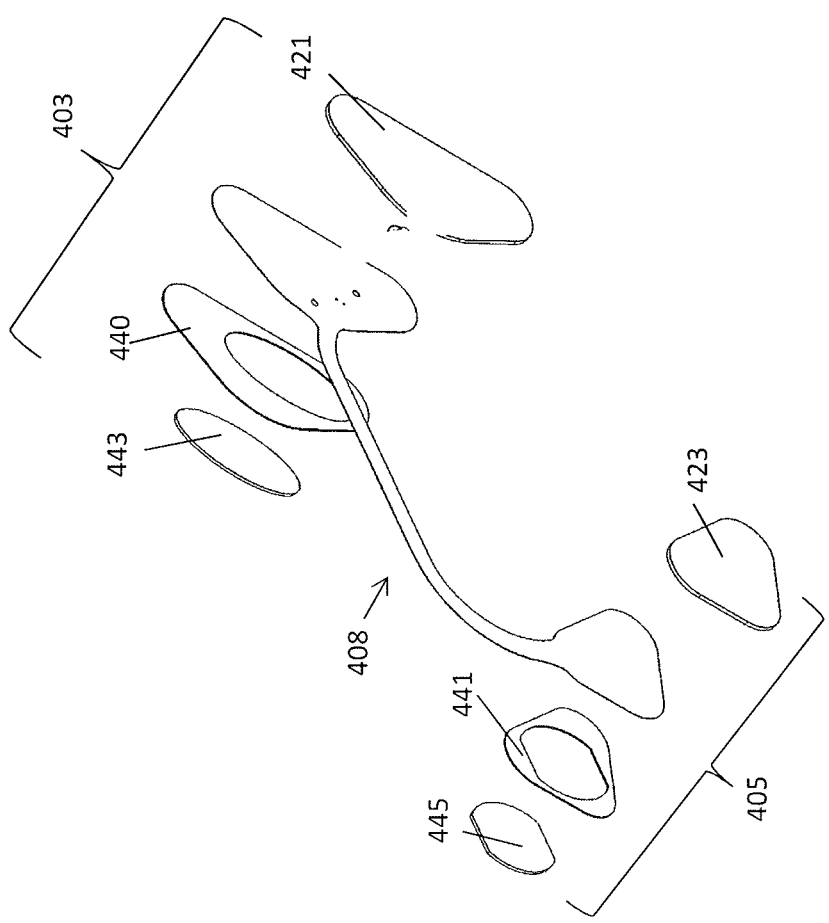
FIG. 10D is an exploded view of the electrode apparatus of FIG. 10A.

FIG. 10D shows an exploded view of the electrode assembly of FIGS. 10A-10C. In this example, the substrate (elongate body 408) forms the elongate body region between the first electrode portion 403 (formed of the first electrically active region having conductive material (not visible in FIG. 10D), hydrogel overlying the electrically active region 443, adhesive 440 and optional backing material 421, as well as a portion of the substrate 408) and the second electrode portion 405 (formed of the second electrically active region (not visible), hydrogel overlying the electrically active region 445, adhesive 441 and optional backing material 423, as well as a portion of the substrate 408). One or more electrical traces may also be included, e.g., directly printed (or silk-screened, etc.) onto the substrate 408.

Figure 10E:
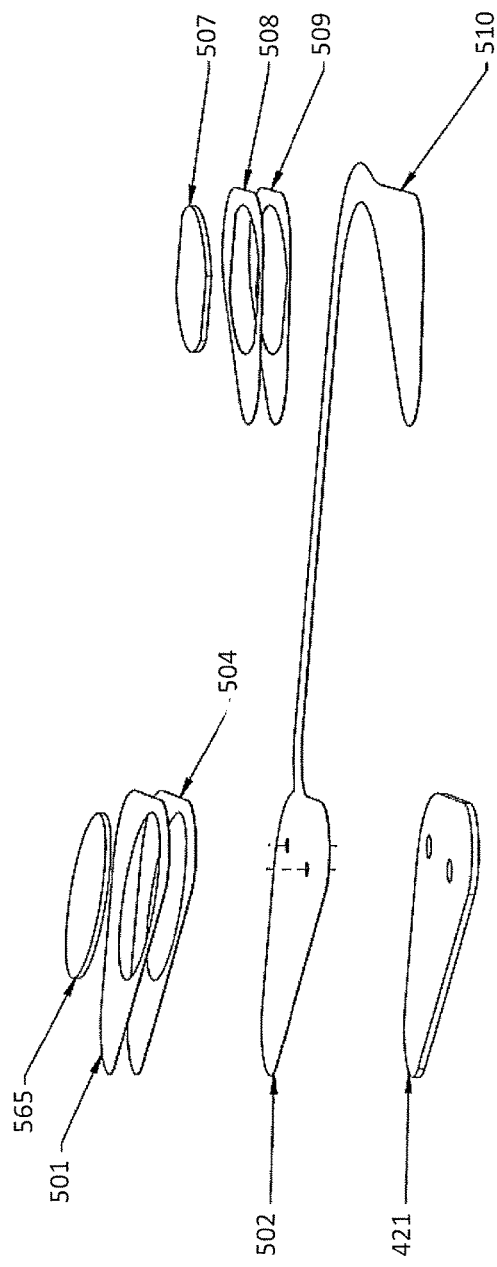
FIG. 10E is another variation of an electrode assembly similar to the variation shown in FIG. 10A, shown in an exploded bottom perspective view.
Figure 10F:
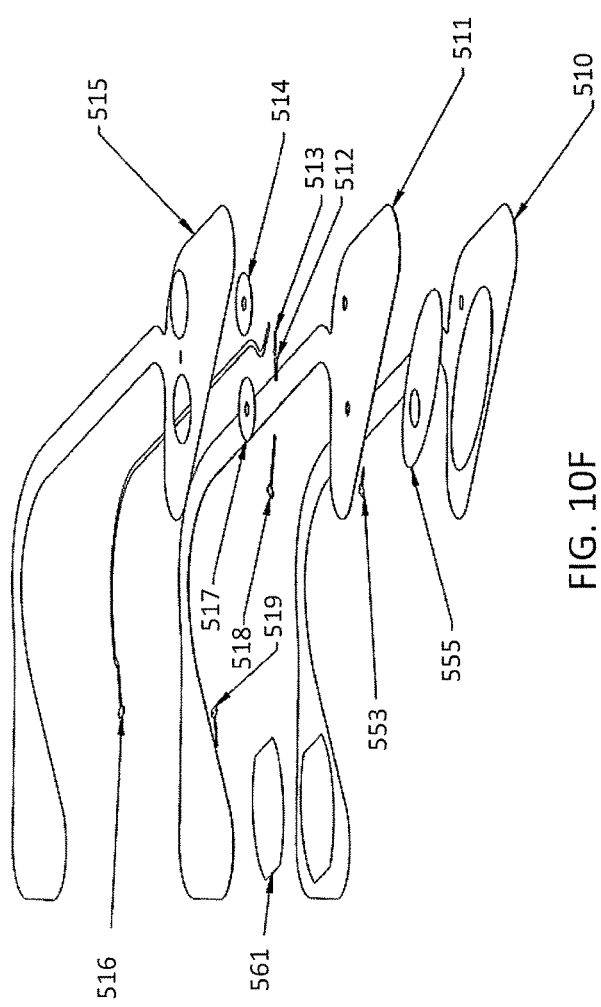
FIG. 10F is another variation of an electrode apparatus, shown in an exploded view.
Figure 10G:
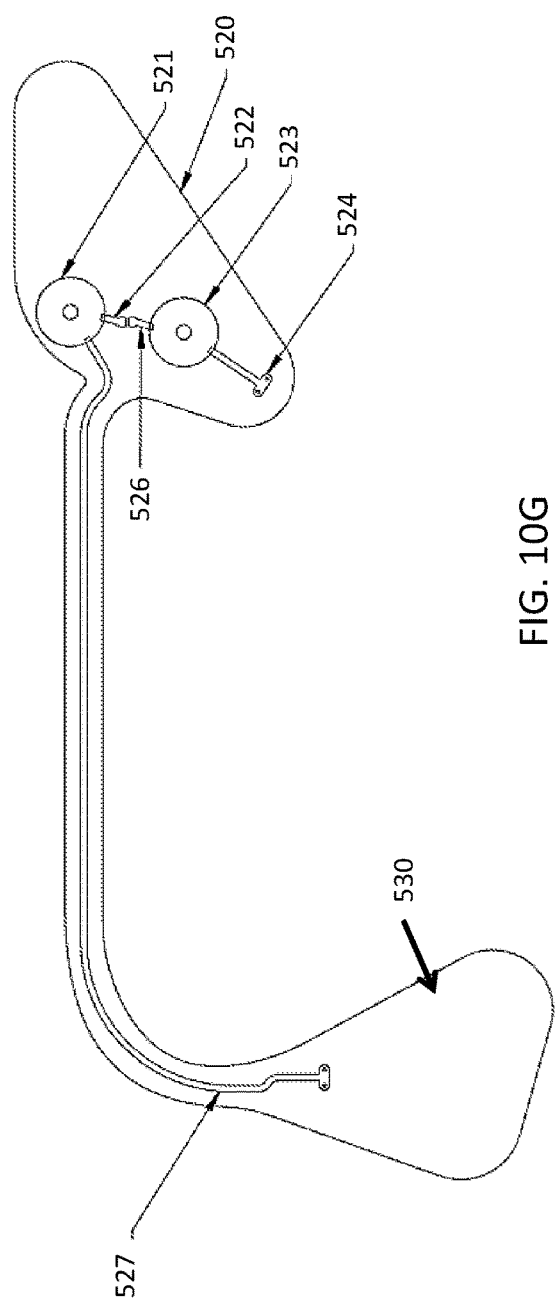
FIG. 10G is a front view of the variation shown in FIG. 10F that may be worn so that a first electrode active region is positioned on a user's temple region on a first (e.g., right or left) side of the body while a second electrode active region is positioned on the user's mastoid region.
Figure 10H:
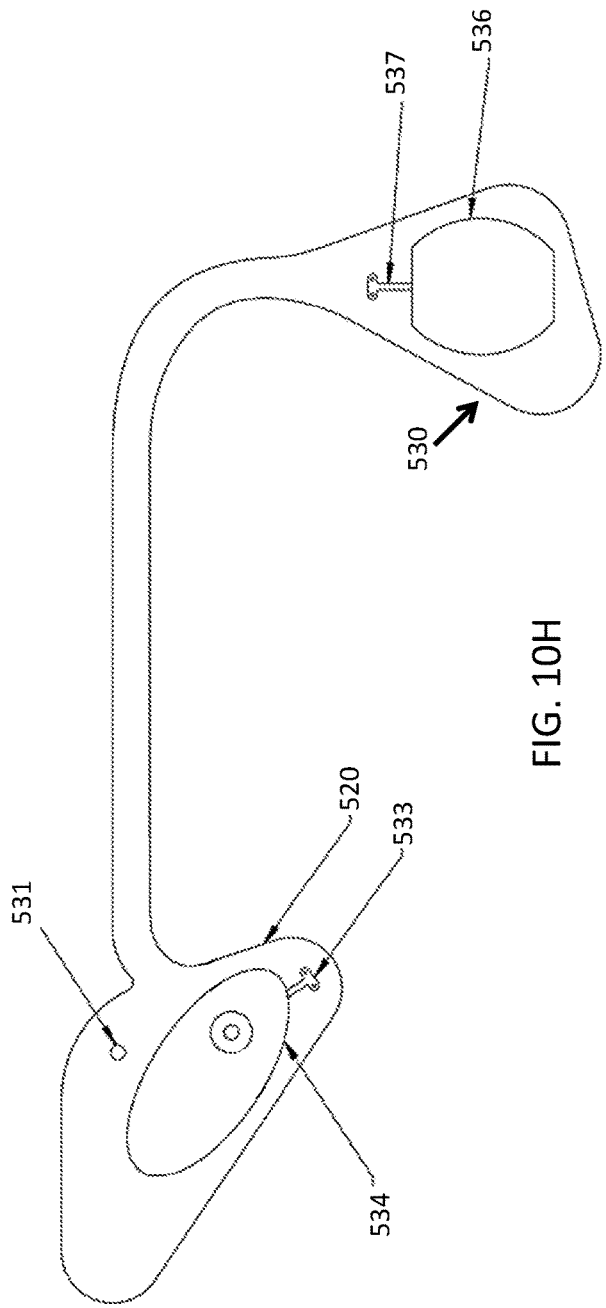
FIG. 10H is a back view of the electrode assembly of FIG. 10G.

FIGS. 10E and 10F show examples of exploded views of electrode assemblies. FIGS. 10G and 10H show front and back views, respectively, of this variation of a flexible electrode assembly.

FIG. 10F shows an exploded view of the flexible electrode assembly components for transdermal electrical stimulation configured similar to the variation shown in FIG. 10A. The apparatus is configured with a shape so that a first electrode active region may be placed on or near a subject's right temple and a second electrode active region may be placed on a subject's right mastoid region In some variations, the apparatus may be formed of multiple substrate layers. For example in FIG. 10F, the electrode apparatuses includes a skin-facing dielectric 510 layer that is an insulative layer. An additional dielectric layer 515 may be positioned to face outwards (distal from the skin and the skin-facing layer) and may have cut-out regions (exclusions) so that two snap connectors can pass through the layer. The layer may also include one or more small rectangular exclusions so that a capacitor soldered onto the internal flexible electrode substrate 511 has sufficient clearance. The top 515 (outward facing) and bottom 510 (skin facing) layers may be coatings or may be formed of solid materials that are adhesively attached to the inner substrate material 511.

In this example, an oval region 555 is a printed (silk screened, etc.) region that is formed or attached to the flexible substrate 511, and may be formed of a conductor and/or sacrificial layer (e.g., Ag/AgCl layer as described in more detail below), forming the first electrode active region. In this example, the Ag/AgCl region has a round exclusion area so that the eyelet portion of a snap electrode does not directly contact the active electrode area. Direct contact between a snap and the electrode may cause oxidation of the electrode area or create a galvanic cell due to the chemistry of the included components.

FIGS. 10E-10H also illustrate various conductive traces which may be present on any of the variations described herein, to connect the electrically active regions to the electrical/mechanical connectors, such as the second electrode active region. For example, a conductive trace 553 may be formed on the skin-facing side of the flexible electrode apparatus and may conduct current through a conductive via passing from the second (outward-facing) side of the apparatus to the electrode area. A conductive, non-consumed (i.e. metal) layer (e.g. Ag, Cu, Au, conductive carbon, etc.) may also be included (not shown in FIG. 10F) as one layer forming the first and/or second electrically active regions. This conductive, non-consumed layer may be printed as a contiguous region from trace 553 and has a similar shape as the Ag/AgCl layer 555 ("sacrificial layer"), which extends slightly beyond the underlying conductive region at all boundaries (including the interior boundary of the circular exclusion, if present) in order to ensure there are no shorts between the conductive layer printed on the flexible substrate and the overlying hydrogel. Such a short may cause current to bypass the pH buffering Ag/AgCl layer and reduce the comfort and efficacy of transdermal electrical stimulation.

Similarly, for a second electrically active region (which may be configured to position over the mastoid, as shown in FIG. 10F), a conductive trace 519 may be functionally similar to the conductive trace 553 in the first electrically active region and may be positioned and shaped to be co-incident with the Ag/AgCl layer 561 or with a conductive non-consumed layer that is in contact (and surrounded on all peripheral sides by) the Ag/AgCl layer.

In this example, flexible substrate 511 (e.g. formed of a material such as polyethylene) may form the base onto which the electrodes and any circuit elements are printed and/or attached, glued, adhered, silk-screened, etc.

In this example, two or more conductive carbon circular regions 514 and 517 may be coupled between the conductive traces. Traces 512 and 513 in this example are connected by a capacitor (as described in greater detail below) that may be used as part of a capacitive element for electrode assembly identification. A capacitor is not shown in FIG. 10F, but would connect between, for example, the first and second active region, e.g., between the two electrical connectors (e.g., snaps) by traces 512, 513. Trace 518 may carry current to conductive vias (not shown) to trace 553 on the skin-facing side of the electrode assembly that is contiguous with the first electrode region (e.g., the conductive non-consumed layer, if included).

Similarly, trace 516 may carry current through a conductive via to trace 519 on the skin-facing side of the flexible electrode assembly that is contiguous with the second electrode active region (e.g., a conductive non-consumed layer, if included).

FIGS. 10G and 10H show front (away-facing) and back (skin-facing) views, respectively, of a flexible electrode assembly such as the one shown in FIG. 10F. In the plane of the electrode apparatus, the first electrode active region is at a proximal 520 end, and the second electrode apparatus is at a distal end region 530.

In any of the variations described herein, a conductive layer such as conductive carbon or another conductive material (e.g., annulus 523) may connect to an electrical stimulator unit, as well as traces that transmit current to a first electrode 534. One of the conductive carbon annuluses 521 may connect to one or more traces that transmit current to the second electrode active region 536.

In this example, a conductive trace 524 on the front (facing away from the subject's skin) side of the apparatus transmits current from the conductive connector (e.g., from the conductive carbon layer) through a conductive via (not shown) to trace 533 on the skin-facing (back) side and then to the first electrode active region 534, which may be formed of the conductive layer(s) (e.g., non-consumed conducting layer and overlaid consumed conductive layer, and hydrogel layer). A through hole 531 in the substrate may provide clearance for a second electrical connector (e.g., conductive snap) to be riveted through the flexible substrate. In FIG. 10G the traces 522 and 526 may act to short the two electrode paths through a capacitive element (e.g., capacitor, not shown) which may be used to identify the type and veracity of an electrode assembly as described in detail below.

FIG. 10*i* illustrates a variation of an electrode assembly 600 worn on a subject's head. As illustrated, the apparatus is positioned with the first electrode portion adhesively attached at the temple region and a second electrode portion attached to a region behind the head (e.g., behind the ear or neck region, not shown).

FIGS. 14A-14C shows another example of an electrode assembly similar to the variation shown in FIGS. 10A-10D. The electrode apparatus includes a first electrode portion 1403 and a second electrode portion 1405. FIGS. 14A and 14B show front perspective and front views, respectively. In this example, the front side does not include any foam/backing material or additional adhesive material around either electrode portions, although such may be included. As in FIGS. 10A-10C the overall shape of the electrode apparatus may be adapted to connect to a subject's temple with the first electrode portion 1403, the elongate body region may be bent around the subject's head, and the second electrode portion 1405 may be in electrical contact with a region behind the subject's ear (e.g., at or near the mastoid). By placing the first active region 1433 of the first electrode portion 1405 in electrical contact with the skin at the temple region and using the adhesive material 1440 surrounding the electrically active region 1433 to hold the electrically active region (and the attached neurostimulator) in position, the second electrically active region may also be adhesively 1441 held to skin so that the second electrically active region 1435 is in contact with the mastoid region.

FIGS. 23A-23B also illustrate another example of an electrode array, similar to those described above in FIGS. 10A-10D and 14A-14C. As described above, the electrode apparatus/assembly includes a pair of skin-contacting electrode regions 2327, 2329. The second skin-contacting electrode region 2329 will be positioned away from the first skin-contacting electrode region 2327 and the neuromodulation components, but will also be held against the subject's skin, for example, behind the ear.

FIG. 23B shows the back of the electrode assembly, which is configured to face (and contact) the subject wearing the apparatus. In this example, both skin-contacting electrode regions include active regions that extend from at least one edge of the apparatus across the skin-contacting electrode region to form the active zones on the skin-contacting electrode regions. For example, in FIG. 23B, the first skin-contacting electrode region 2327 has an active region 2205 that forms a central strip across the skin-contacting electrode region 2327. In other examples, the hydrogel 2205, 2209 may extend from one edge of the electrode region to another edge of the electrode region, while the underlying electrode active area only covers a subset of this region in order to ensure the electrode is appropriately sized and located in order to be positioned effectively for inducing a cognitive effect. As described in more detail in reference to FIGS. 20A-20F, below, this active region may include a layered structure of conductive metal, sacrificial conductive layer, and hydrogel to spread the current across the entire active region; in some variations one or more additional layers may be included, such as a less-conductive (than the conductive metal and sacrificial layer) layer, e.g., comprised of carbon, between the conductive metal and sacrificial layer, that may help spread out the current across the surface of the active region before it passes into the sacrificial layer and therefore allow higher current intensities to be delivered more uniformly across the electrode-dermal contact area and thus reduce discomfort in the user. The second skin-contacting electrode region 2229 is similarly constructed and is electrically connected to the other electrode active region 2205 by a conductive trace on or in the portion of the flexible substrate 2307 extending between the two skin-contacting electrode regions.

Any electrode assembly described herein (including the electrode assembly shown in FIGS. 23A-23B) may be formed of a substrate such as a Kapton (e.g., a polyimide film) and/or vinyl (e.g., coated vinyl, polyvinyl chloride or related polymer) onto which the different regions are formed by layering or attaching. The active region may include a hydrogel (e.g., AG602 Hydrogel, having a resistance of approximately 350 Ohm-cm), and Ag coating (e.g., Ag ink), Ag/AgCl coating (e.g., Ag/AgCl ink), and (optionally) a carbon conductor (e.g., Exopack Z-flo carbon filled Vinyl having a resistance of approximately <90 Ohms/cm$^2$).

In another variation, an electrode assembly such as the one shown in FIGS. 23A-23B (or FIGS. 22A-22B) may include a substrate (e.g., Kapton or other polymeric material) and may include the active region with a hydrogel (e.g., AG602 Hydrogel, at 350 Ohm-cm), a silver/silver chloride sacrificial layer (e.g., ECM Ag/AgCl ink (85/15) with <0.2 Ohm/cm2), the optional carbon layer (e.g., DuPont Carbon 5000 ink, <50 Ohm/cm2), and silver layer (e.g., EMC Silver ink with <0.2 Ohm/cm2).

As mentioned above, the elongate body region of the electrode apparatus that connects the two electrode portions may be any appropriate length, but is generally longer than a few inches (e.g., longer than about 2 inches, longer than about 3 inches, longer than about 4 inches, longer than about 5 inches, longer than about 6 inches, longer than about 7 inches, longer than about 8 inches, longer than about 9 inches, etc., between 2 and 12 inches, between 2 and 10 inches, between 3 and 9 inches, etc.). In the plane of the electrode apparatus, the elongate body region may travel in a bent or curved path, as illustrated in the variations of FIGS. 7A-9, FIGS. 10A-10D, FIGS. 13A-13D and FIGS. 14A-14D, helping to allow the material to flex or bend to be adjustably positioned over and/or around the subject's head, as shown in FIGS. 6 and 10*i*.

Although the variations described above for the electrode assembly illustrate a flexible structure, in which a substrate (e.g., flex circuit) material is thin and permitted to bend in at least one axis, in some variations the electrode assembly may be rigid. FIGS. 12A-12C and 12D-12F illustrate two variations of rigid, or semi-rigid assembly electrode apparatuses.

Figure 12A:
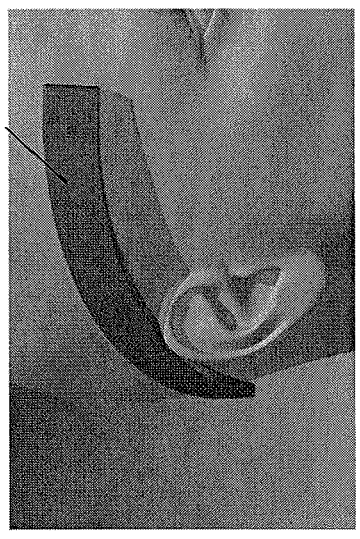
FIGS. 12A-12C show three views illustrating another variation of an electrode assembly having a rigid body.
Figure 12B:
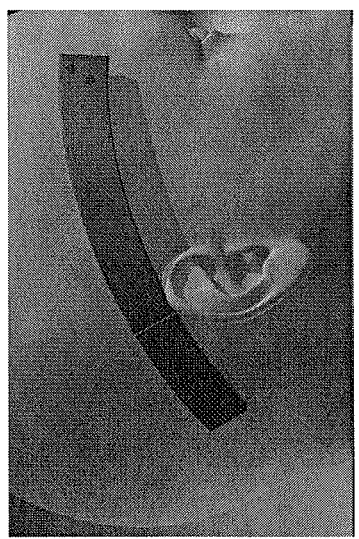
Figure 12C:
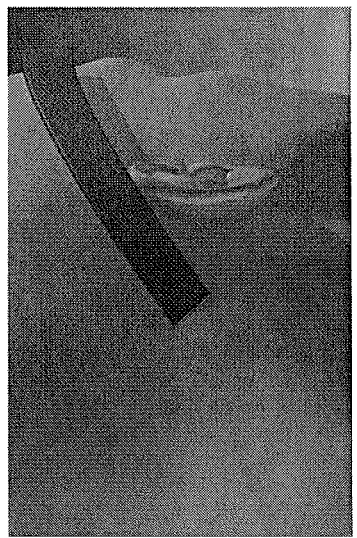

In FIGS. 12A-12C, the device is shown as a CAD rendering of an exemplar neurostimulator 901 attached to an electrode assembly that may be bendable (ductile) or hinged to achieve a wearable form factor allowing contact with different regions of the head/neck. For example, an anode electrode (the electrically active region of the first electrode portion) may be positioned on the right temple area and electrically conductive when the posterior portion (e.g., the second electrode region) of the electrode assembly may be positioned so that a cathode electrode targeting the right mastoid behind the ear is positioned correctly (electrode active region not shown).

Figure 12D:
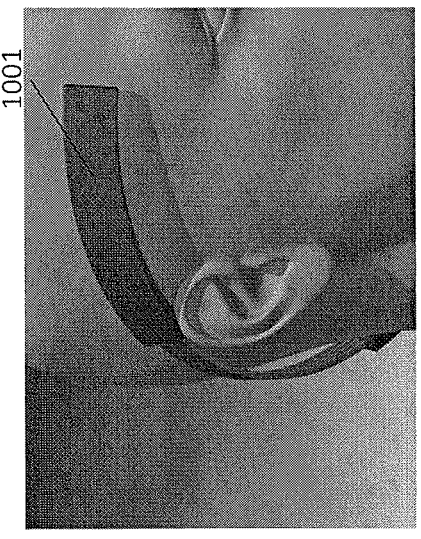
FIGS. 12D-12F show three views illustrating another variation of a cantilever electrode apparatus.
Figure 12E:
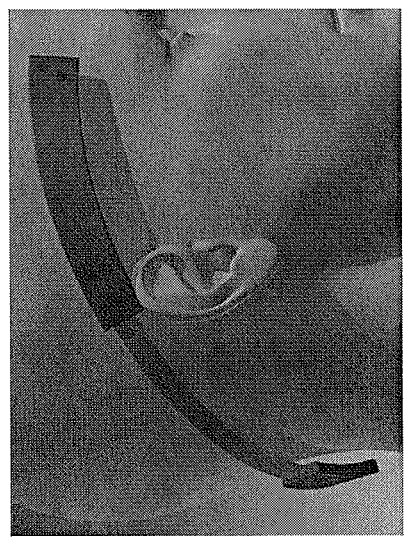
Figure 12F:
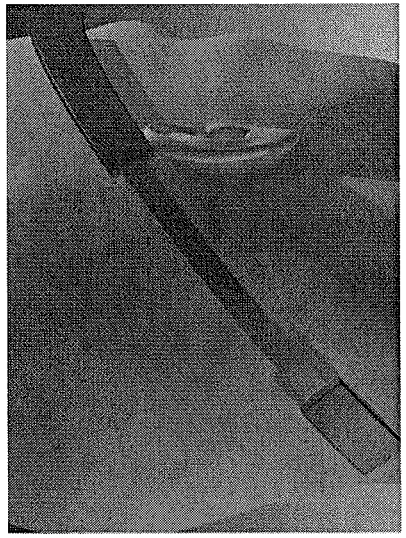

Similarly, the example shown in FIGS. 12D-12E illustrates a region having a rigid elongate body (including connector region of the elongate body), the elongate body extends further and may allow contact with the second active region on the back of the subject's neck. All or a portion of the body may be ductile so that it can be bent into a shape allowing it to conform to the neck. In some variations the elongate body may be hinged to allow it to bend/flex during use.

Figure 12H:
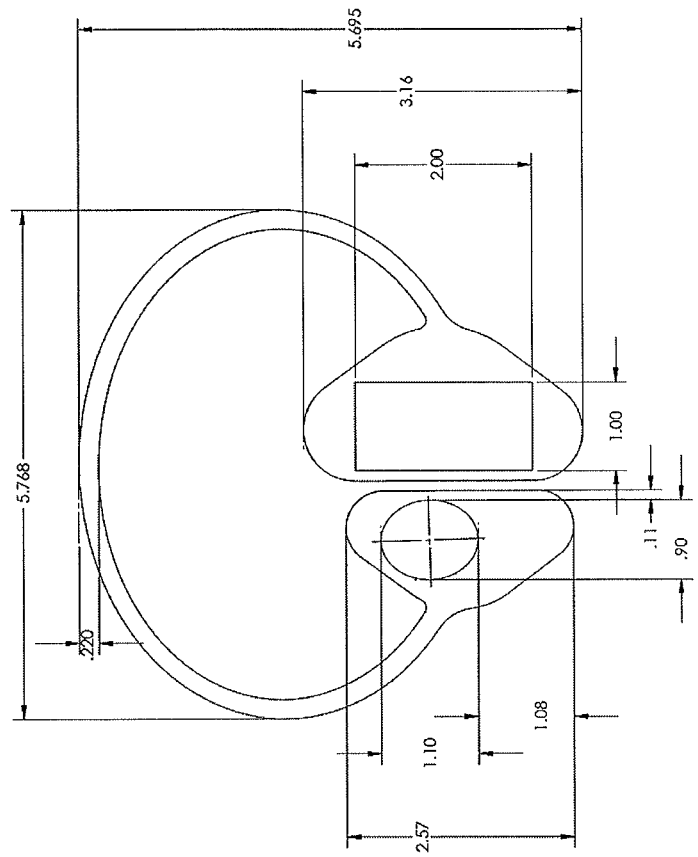
FIGS. 12G-12H show front and back views, respectively, of another variation of an electrode assembly.
Figure 12G:
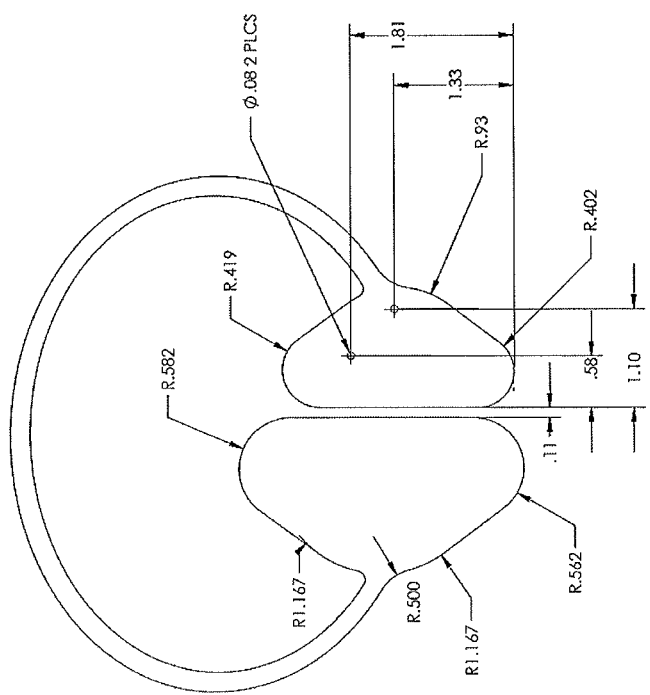

FIGS. 12G and 12H illustrate another variation of a flexible (at least in one axis of freedom) electrode apparatus which may also be formed of a flex circuit material. FIG. 12G shows a front view and FIG. 12H shows a back view of the substrate portion onto which the other elements (e.g. components of a neurostimulator) may be attached (e.g., the active regions, the connectors, adhesive, etc.). In this example, the device includes an elongate thin connector portion of the substrate body, similar to the variations shown in FIGS. 7A-9 and 10A-10D, above. Exemplary dimension (in length units of inches) are shown for illustrative purposes only, and may be varied.

Figure 12I:
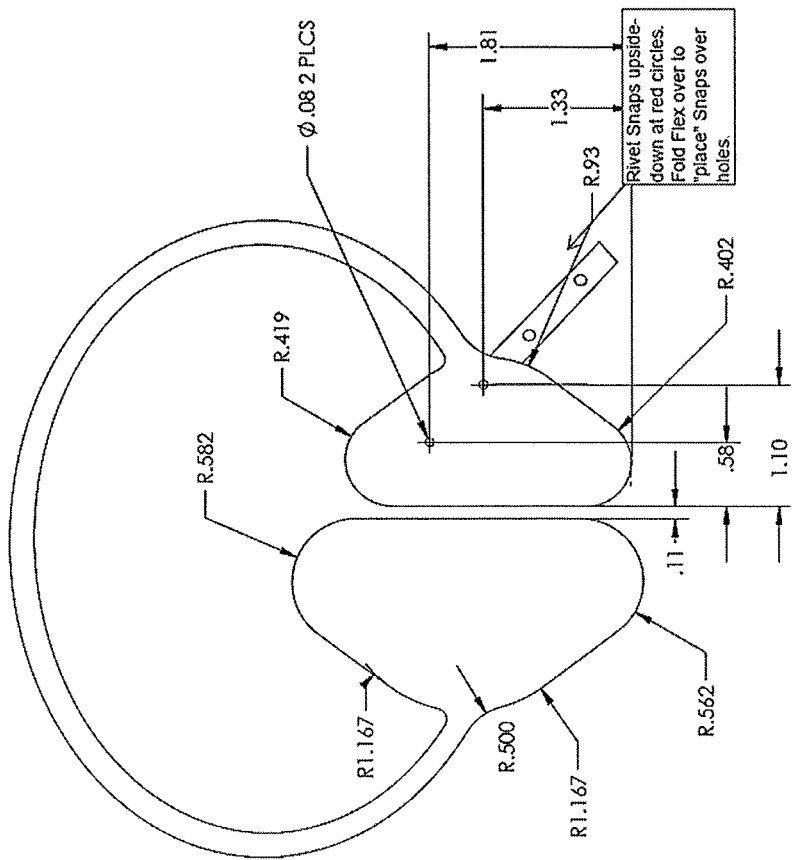
FIG. 12i is a front view of another variation of an electrode apparatus.

FIG. 12i is another variation of an electrode assembly including connectors. In this example, the connectors are coupled to a different portion of the substrate in an upside-down configuration, connected by conductive traces (not shown), and folded back over so that they may be positioned over the first electrode region but without requiring the connector be riveted through the flexible substrate into the active region, similar to what is illustrated in FIGS. 7A-9, and 10A-10D above. Also, this may allow a better fit for larger electrodes while reducing the constraint of where a connector for the active region is located. As described herein, it may be advantageous to avoid coupling to a separate neurostimulator, or instead connecting to a cord, cable, or tether that integrates some or all of the TES neurostimulator circuitry, as shown in FIGS. 1A-4C, above. When connectors, such as snaps, buttons, etc., are used, they may be configured so that they engage with the separate device (e.g., neurostimulator, cord, etc.) on the top surface opposite from the skin, or in some variations on the bottom surface, facing the skin.

Figure 15B:
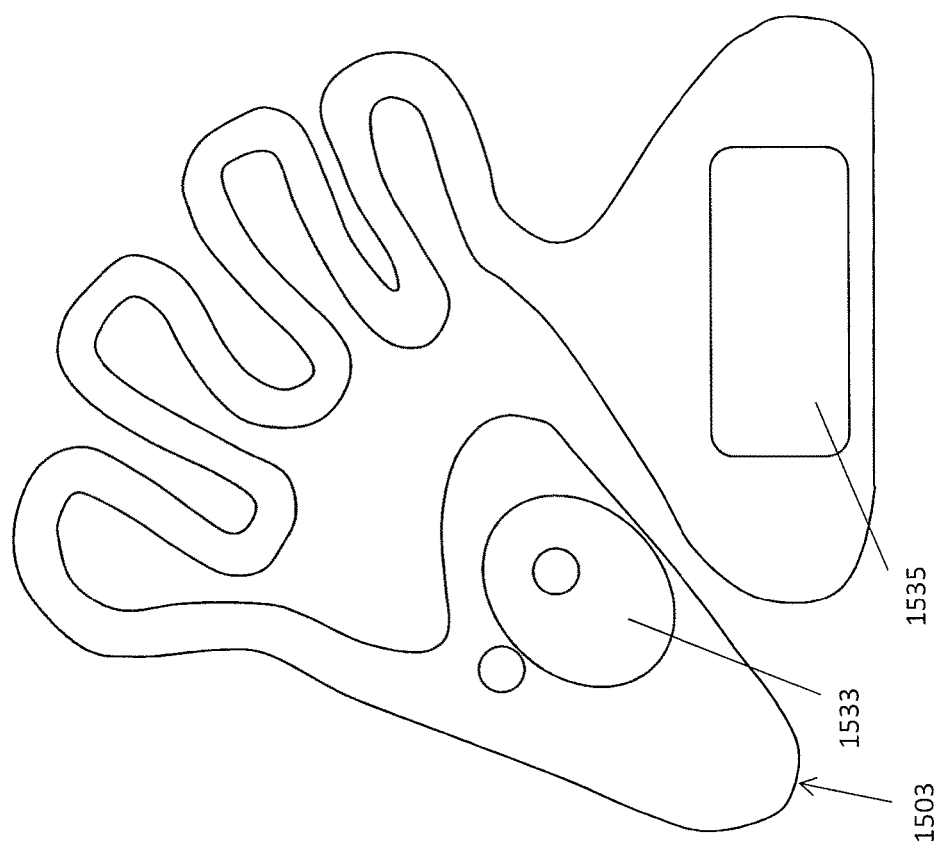
FIGS. 15A and 15B show top and bottom views, respectively, of another variation of an electrode assembly.
Figure 15A:
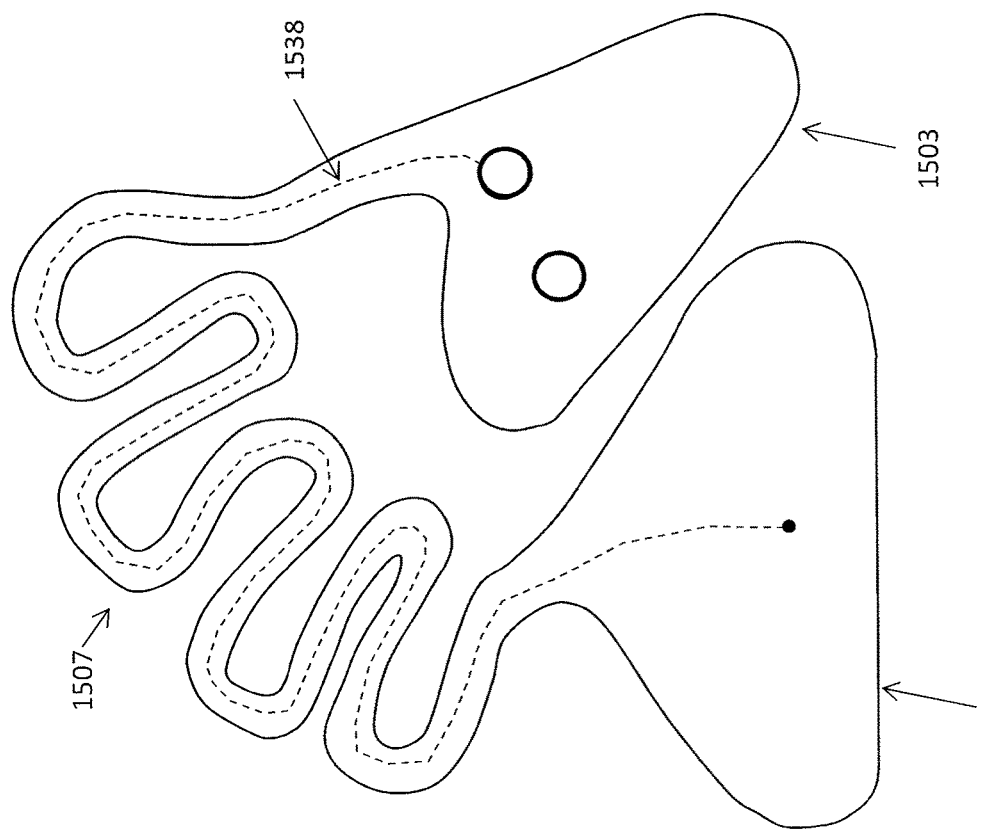

FIGS. 15A and 15B illustrate another variation of an electrode assembly that includes a winding connector region to adapt comfortably to different anatomies by extending without substantial force pulling adhesive-containing electrode areas off of the skin. A second electrode portion (region 1505) is connected to the first electrode region by elongate body region 1507. In FIG. 15A, the connecting trace extends down the elongate body region 1507 on the top surface, and may be insulated. As with any of the layers forming the electrically active region, the trace (and/or insulator) may be printed, silk-screened, deposited, or otherwise applied to the substrate. In this example, the second connector 1517 is not positioned over the first active region, which may prevent shorting of the first and second active regions; however in some variations the connectors may both be entirely or partially positioned over (on the opposite side of) the first active region.

As discussed above, any of the electrode apparatuses herein may be flexible multi-electrode assemblies that are typically flexible such that two separate but connected regions of the electrode assembly conform to two or more body regions of a user, such as a portion of the user's forehead and/or neck and/or an area surrounding an ear. Conforming the multi-electrode assembly to the body portion of the user may result in increased comfort during electrical stimulation, increased uniformity in impedance, and improved cognitive effects. In some embodiments, the use of a unified assembly with multiple electrodes (e.g., multiple electrically active regions) may eliminate the need for connectors and/or cables between electrically active regions on the electrode assembly. The substrate of the electrode assemblies described herein may be a flexible nonconductive substrate onto which the electrically active regions are formed or placed.

Any of the electrode apparatuses described herein, including the electrode apparatuses or multi-electrode assemblies, may be disposable, and single-use or multiple-use, allowing use for a plurality of times before being disposed. Alternatively, the electrode apparatuses may be durable and reusable for any length of time, for example only requiring replacement or refurbishing of certain components or elements of the device or system. An electrode apparatus as described herein is not limited to the neuromodulation systems and techniques described herein, but may be used in other fields and/or applications. For example, the electrode apparatuses described herein may be used in fuel cells, medical applications (e.g. EEG, ECG, ECT, defibrillation, etc. . . . ), electrophysiology, electroplating, arc welding, cathodic protection, grounding, electrochemistry, or any other electrode application. An electrode apparatus may be used to target non-neuronal tissues and may be placed on any portion of the body. For example a flexible electrode system as described herein may be used for muscle therapy for healing an injury.

Figure 18B:
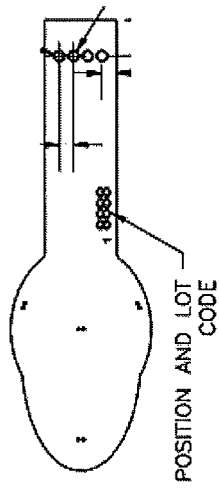
FIGS. 18A-18C illustrate a portion of an electrode apparatus including different sub-regions of active zones.
Figure 18C:
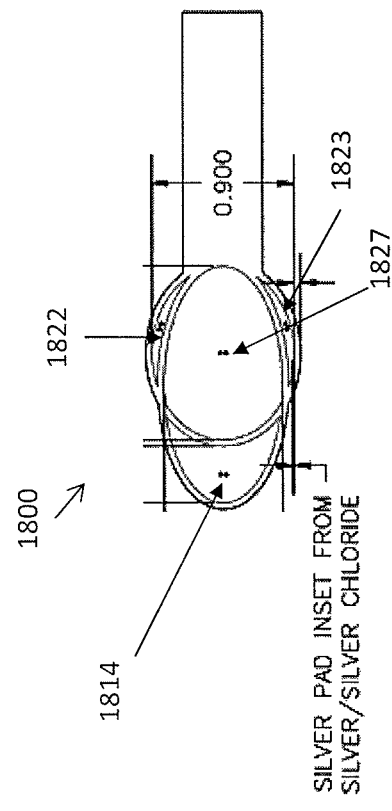
Figure 18A:
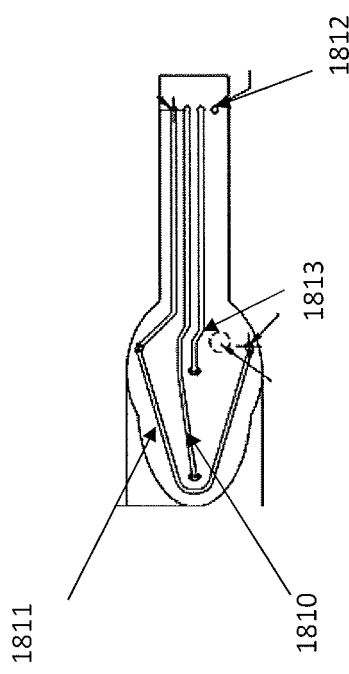

FIGS. 18A-18C illustrate one variation of a flexible electrode apparatus that includes a flexible substrate, at least two conductive traces, an adhesive component, and at least two electrodes. The electrode apparatus is preferably used for noninvasive neuromodulation, but can additionally or alternatively be used for any suitable applications, clinical or otherwise.

In FIG. 18A, a flexible substrate 1812 may include a first surface and a second surface, as shown in FIG. 18A (top view) and FIG. 18B (bottom view), respectively. The second (bottom) surface is opposite the first (top) surface. The flexible substrate may include two or more apertures each coated with an electrical conductor, such that the electrical conductor (e.g., carbon black, silver, etc.) delivers current between the first and second surfaces. As shown in FIG. 18C, the first surface may include one or more active regions 1814, such that current from the second surface is delivered to the electrodes on the first surface.

In general, an active region of an electrode may be divided up into multiple zones or sub-regions that can be individually and/or collectively driven and/or sensed from so that the size of the active region of the electrode apparatus can be increased and/or decreased as needed. This modification may be controlled by the neurostimulator and/or the controller (e.g., a control unit, including a control application that is operating on a smartphone, etc.), which may determine which groups of active regions of an electrode (typically anode or cathode) is active at a particular time. In some variations, multiple regions (sub-regions) of the active region are tied together so that they may operate together. This is illustrated, for example, in FIGS. 18A-18C.

Figure 16A:
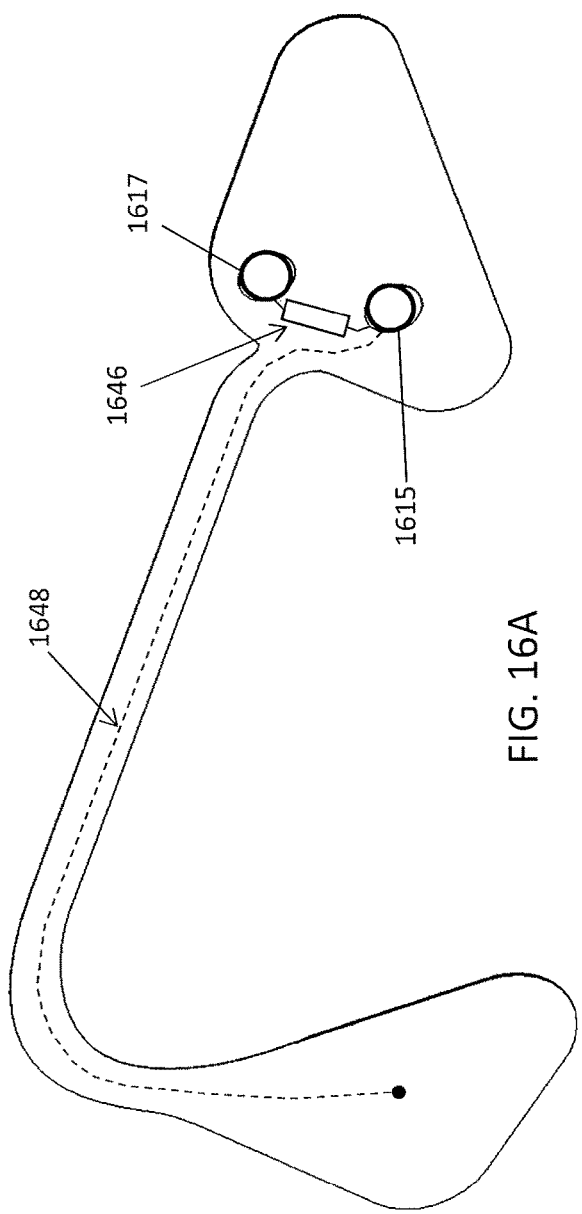
FIG. 16A is a perspective view of a variation of a cantilever electrode apparatus having a detectable electrical element between the first and second electrodes that can be sensed by a neurostimulator.
Figure 16B:
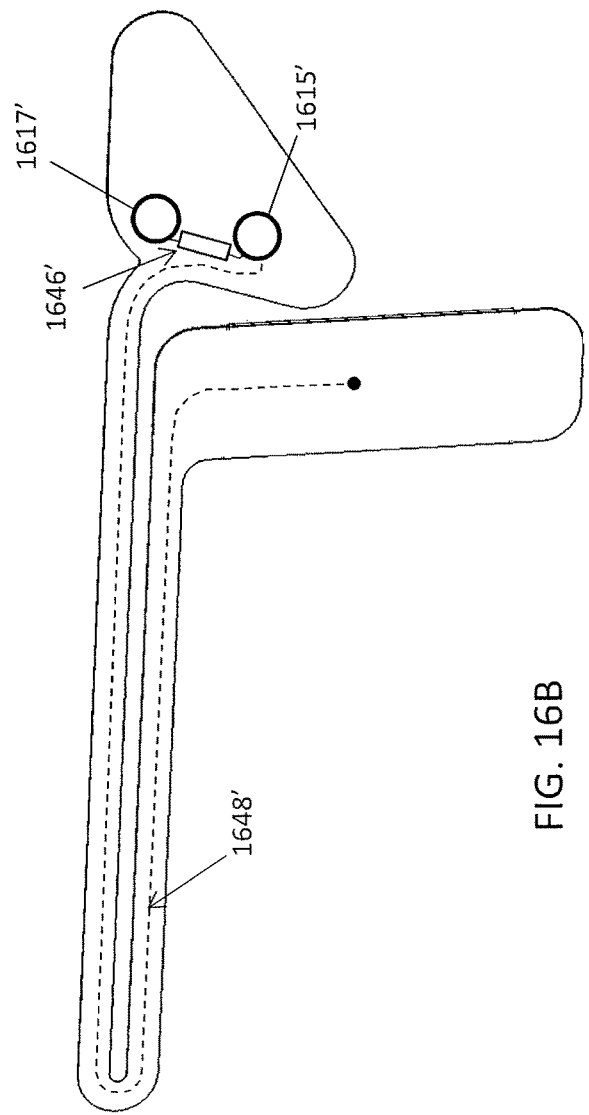
FIG. 16B is another example of a perspective view of a cantilever electrode apparatus having a detectable electrical element between the first and second electrodes that can be sensed by a neurostimulator.

Each sub-region of the active region may be separately or collectively coupled to a trace that connects to the power supply and/or controller. For example, FIG. 18A shows a substrate having multiple (e.g., three) conductive traces printed on an upper surface (though any surface, e.g., the top or bottom surface, may be used). The conductive traces may be printed, silk-screened, etched, soldered, welded, or otherwise attached to the surface. In some embodiments, the conductive surface may include more than two traces (e.g. FIG. 18A, three traces are shown). For example, a first trace 1810 on the back side of the portion of the apparatus shown is coupled though an opening in the substrate (which may be filled with a conductive material) to a first area of an electrode (1814 in FIG. 18C); a second trace 1811 is coupled to second and third electrode areas (1822, 1823 in FIG. 18C), where these regions are electrically shorted (connected) together; a third trace 1813 is coupled to fourth electrode area (1827 in FIG. 18C) or alternatively may be connected to a secondary electrode on either the same assembly or a second assembly. The traces may be connected to an electrical/mechanical connector for coupling to the neurostimulator. This connection may be direct, or they may be coupled to a chip, resistor, capacitor, or the like (including a capacitive element as discussed above). The sub-regions shown in this example may therefore be used to provide a single electrode apparatus that can have one or more (e.g., two) active regions that can have different dimensions, and therefore be used on different regions of the body. In practice this may allow a single electrode apparatus having at least one active region that is configured to have multiple sub-regions in which different combinations of sub-regions may be separately operated together to provide a particular shape and/or pattern for the active region. Thus, whereas separate electrode apparatuses configured for energy and relaxation are described above (e.g., FIGS. 16A and 16B, respectively), in some variations a single electrode apparatus may by dynamically configured or configurable to evoke either "energy" (using a large, relatively circular active region for placement behind the ear/on the mastoid region) or "calm" (using a more rectangular active region for placement behind the neck).

Figure 19D:
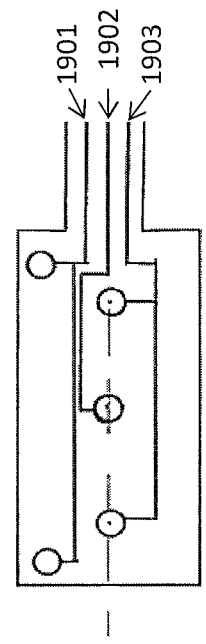
FIGS. 19B-19D show bottom, side sectional, and top views, respectively, of another variation of an electrode apparatus having multiple sub-regions forming an active region of the electrode on the bottom surface.
Figure 19A:
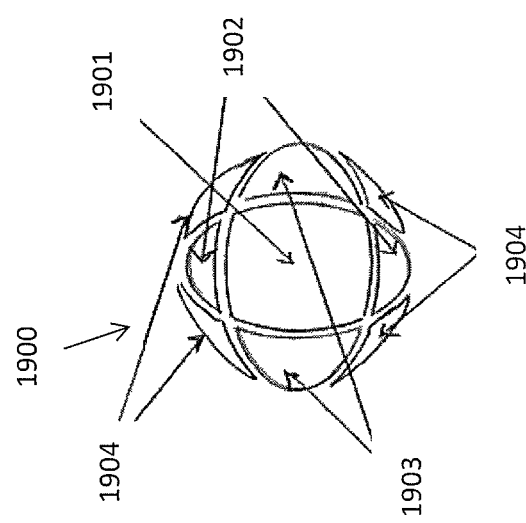
FIG. 19A is a bottom view showing multiple sub-regions forming an active region of the electrode on the bottom surface, similar to that shown in FIG. 18C.
Figure 19B:
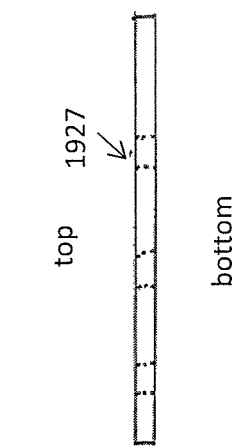
Figure 19C:
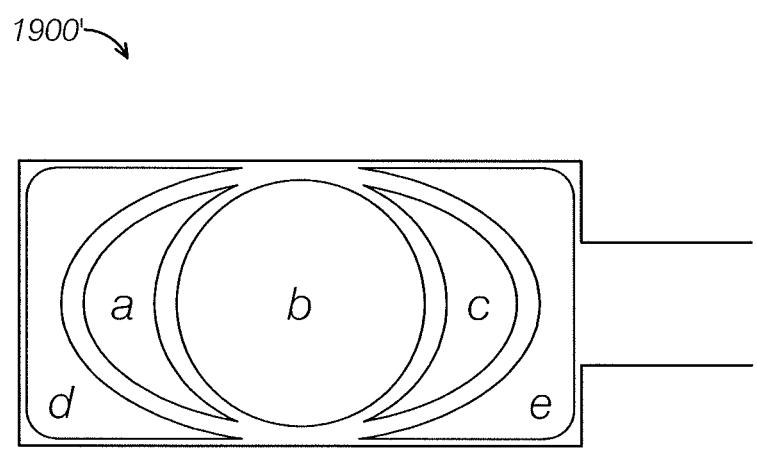

FIGS. 19A-19D show other variations of active region of an electrode apparatus in which the active region is formed of a plurality of sub-regions that may be operated together in different sub-combinations, so that they may be differentially stimulated or read from, and the size or shape of the effective active region on the surface, and thus the electrical stimulation area, may be adjusted to effect different neuromodulation outcomes. Selecting specific sub-regions of the active region from an array of active sub-regions on the surface can be used to focus stimulation to a preferred area, compensate for changes in impedance (e.g. if part of the array shifts away from the skin during use), avoid uncomfortable areas, compensate for changes in electrochemistry to improve comfort (e.g. reduced AgCl in a particular electrode vs. another) or other uses. As shown in FIGS. 19A-19D, a conductive trace on the opposite (top) surface from the active region (see, e.g., FIG. 19D) may extend to a distinct active sub-region on the bottom surface, as shown in FIG. 19B. In this example, FIG. 19D is the top surface and FIG. 19B is the bottom surface of the same electrode region. Each conductive trace may control the electrical stimulation delivered by the sub-region or sub-area to which it is coupled. For example, activating electrode areas 1901 and 1902 may induce a first cognitive effect in a user, while activating electrode areas 1901, 1902, and 1903 may induce an alternative or modified cognitive effect in a user. Any combination of electrode areas may be used to achieve the desired neuromodulation outcome. FIG. 19B illustrates how three conductive traces may be positioned to control three electrode areas. For example, trace 1901 (FIG. 19D) controls areas d and e, trace 1903 controls areas a and c, and trace 1902 controls area b. In some embodiments, any number of electrode areas may be positioned on each electrode. Further, the electrode active sub-regions may be clustered in an area of the flexible assembly or distributed over a region of the flexible assembly. Electrical current from a controller or current delivery device (neurostimulator) may be delivered to the traces through one or more connectors or pins, for example pogo pins or conductive snaps, extending from the controller to the second surface or from the second surface to the controller, such that the pogo pins/snaps are electrically connected with the traces. Further, electrical current from the conductive traces on the top surface may be delivered to the electrode sub-regions on the bottom surface through one or more conductive apertures 1927 or through holes in the nonconductive flexible substrate, as shown in the side sectional view of FIG. 19C. FIG. 19A shows another variation of a bottom portion having an active region for the electrode that includes a plurality of different sub-regions that may be differently operated together to provide different effective active regions (e.g., an active region formed of sub-regions 1902 and 1901 to provide a first oval configuration, an active region formed of sub-regions 1903 and 1901 to provide a second oval configuration, an active region formed of 1904, 1903, 1902 and 1901 to provide a large circular region).

In some variations, a second electrode having an active region formed of multiple sub-regions that may be operated in sub-combinations may be present on the electrode apparatus, e.g., in a spaced relationship from the first electrode. For example, the two electrodes may be spaced apart by about 1 inch, 2 inches, 3 inches, 4 inches, 5 inches, etc. The spacing may be along the connecting region of the substrate, as discussed above (e.g., following the shortest continuous path along the substrate). The electrodes may be spaced apart by any suitable distance so that they may target the two regions on the user's head.

As used herein the path length of the flexible elongate member separating the first and second electrode portions may refer to the length of the connector if it were made straight; this may also be referred to as the distance of travel between the first and second electrode portions. This distance is typically sufficient to allow the first electrode portion to be placed at a first location on the user's head (e.g., the front of the user's head), then adjust (e.g., bend, flex, etc.) the connecting region so that the second connecting region can be placed at a second region on the side of the head, back of the head or neck region. The connecting region extends between the two, so that the path length is the path taken by an electrical trace or wire extending from one of the proud connectors linking the first electrode portion to the electrical stimulator to the second electrode portion.

Within the same overall active region (e.g., 1800 in FIG. 18C, 1900 in FIG. 19A, 1900' in FIG. 19B) the individual sub-regions may be arranged such that current resists traveling through the hydrogel to "inactive" electrode areas, which are not part of an active sub-region being used. Thus, in some variations the adjacent regions may be spaced apart from each other (e.g., so that there is at least 1 mm, 2 mm, etc. between the hydrogel of different regions). In some variations the unused sub-regions may be set to "float" (electrically unconnected to ground or to an active region). In general at least one sub-region is coupled to the first surface and electrically coupled to the second surface through two or more conductive apertures, as described above. Flexible electrode assemblies containing two or more spatially distinct electrodes are advantageous by permitting stimulation between the two electrodes when they are adhered to the skin.

In any of the electrode apparatuses described herein, the first conductive layer (e.g., a Ag layer) connects to the neuromodulation components. This first conductive layer is separated from the sacrificial layer (e.g., Ag/AgCl layer) that connects to the gel (e.g., hydrogel) by the intermediate, less conductive layer. This less conductive layer may also be referred to as a weakly conductive layer, a weakly insulating layer, or a more resistive layer (all in reference to the adjacent first conductive layer and sacrificial layer). In general, this weakly conductive layer has an electrical conductance that is lower than either the adjacent first conductive layer or the sacrificial layer, although the electrical properties of the sacrificial layer may change with use. Thus, in general the weakly conductive layer may be more resistive than the first conductive layer; for example, the weakly conductive layer may have a resistivity that is greater than 3×, 4×, 5×, 6×, 7×, 8×, 9×, 10×, 15×, 20×, etc., the resistivity of the first conductive layer. In some variations, the resistance of the weakly conductive layer is greater than 5× the resistance of the first conductive layer that it covers. In general, each successive layer distal from the flexible substrate (i.e. a polymeric material appropriate for use in a flexible circuit) extends beyond the edge of the more proximal layer along its entire circumference to ensure that current cannot short between non-successive layers.

The weakly conductive layer may be formed of any appropriate material having the electrical properties described herein. For example, the weakly conductive layer may include carbon. For example, the weakly conductive material may be a polymeric material (including rubbers, polyvinyl chlorides, etc.) that is mixed with or incorporates carbon (e.g., carbon particles), etc.

The optional less conductive layer 2044 described above may be helpful to spread the current as it moves from the highly conductive metal layer such as the Ag layer 2005 shown in FIGS. 20A-20F to the sacrificial layer (e.g., Ag/AgCl layer 2007) and into the hydrogel. In effect, this carbon layer (or similar less-conductive layer) may make the electrodes much more comfortable for the user to wear them, even when delivering relatively high intensity current signals, by improving the uniformity of current density and electrochemistry occurring in the consumptive layer and/or hydrogel.

In some embodiments, the electrode apparatus (flexible electrode assembly) may include an adhesive component. The adhesive component may be configured to couple the electrode apparatus to a body portion of a user or any other device or system. An adhesive component may surround and/or be adjacent to the boundary of the consumptive layer. In some embodiments, the adhesive component and the three layers (consumptive, nonconsumptive, and hydrogel) of the electrode active region may be substantially the same thickness, such that substantially all areas of the flexible assembly may be flush with the skin of a user. In some embodiments, the hydrogel layer may extend slightly beyond the adhesive layer so that the hydrogel makes a more uniform contact through slight compression when the electrode is adhered to the skin.

Alternatively, a flexible multi-electrode assembly may be pressed against or held to a body portion of a user. In some embodiments, the flexible transdermal multi-electrode assembly may be pressed against a body portion of the user using a headband, helmet, head scarf, or any other type of wearable device.

As described above, a single flexible transdermal assembly may include two or more electrodes (active regions) for electrical stimulation, such that only one assembly is required for electrical stimulation. For example, a user may stimulate a forehead region with a first electrode region (active region) on the flexible transdermal assembly and the back of the neck with a second electrode region (active region) on the same assembly to achieve the desired neuromodulation effect. Alternatively, the system may utilize two separate or separable assemblies, such that each assembly includes one electrode for electrical stimulation. In some embodiments, the two assemblies may be electrically coupled by a coupling element. For example, a user may position one assembly on the forehead and the second assembly on the back of the neck to achieve the desired neuromodulation outcome. Alternatively, any number of electrodes in each assembly may be used to achieve the desired neuromodulation effect. In some embodiments, any number of electrode areas on the same or different assemblies may be coupled by one or more traces. For example, one trace may couple an electrode area on the forehead to an electrode area on the back of the neck. Alternatively, one or more electrode areas on the same or different assemblies may be independently and directly controlled by the controller, for example through pogo pins as described above.

Figure 11A:
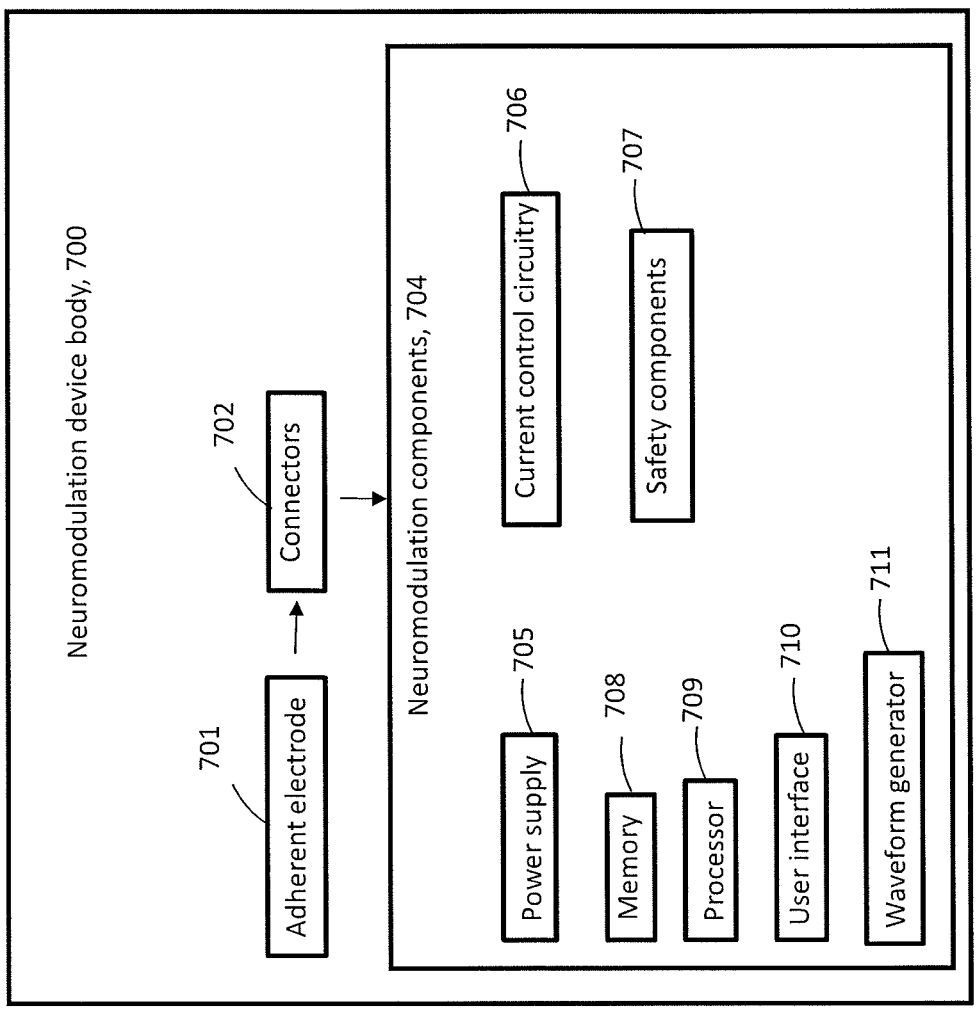
FIG. 11A is a diagram showing the overall configuration of the integrated neuromodulation device.

One improvement over other designs of the neuromodulation device is the miniaturization and integration of these components (i.e. chip, firmware, software) into the main body of the neuromodulation device containing the electrode assembly as can be seen in FIG. 11A. As can be seen in FIG. 11A, the neuromodulation device body contains an electrode assembly 701, and neuromodulation components 704. The neuromodulation components 704 further contain power supply 705, memory 708, processor 709, user interface 710, current control circuitry 706, and safety components 707. A skilled artisan will appreciate that FIG. 11A is one representation of how the neuromodulation device components can be laid out and there are numerous other ways for both the electrodes 701 and neuromodulation components 704 to be integrated.

In order to fit all the necessary neuromodulation components into the body of the electrode assembly, some or all of the neuromodulation components can be contained in the proximal end electrode body or some or all of the relevant neuromodulation components can be contained in the distal end electrode body, or some or all of the relevant neuromodulation components can be contained within the stem portion of the neuromodulation device body. In other variations, the neuromodulation components can be spread throughout the proximal end electrode, the distal end electrode, and the stem portion of the neuromodulation device. In other variations, the electrode apparatus has one contiguous area without a connector region and components may be distributed across the cross section for usability, comfort, and fit.

Another benefit to an integrated electrode and neuromodulation device is that it consumes less power than other configurations of the neuromodulation device when producing the desired waveform sessions (e.g., by eliminating wireless communication components). In one example, the neuromodulation components can be surface mounted components (SMC) and incorporated into the electrode assembly design. Benefits of using SMC is that they are small in size. For example, some SMC components can be approximately 0.25×0.125 mm. Also, components can be placed on either side of the flexible circuit board (ideally restricting components on the first, subject-facing side to the non-adhering (i.e. connector) portion of the flex circuit) for comfort and/or safety. Thus, due to their smaller size and ability to be fitted on either side of the circuit board, a larger number of components can be accommodated within a particular space. Furthermore, SMC components have lower resistance and inductance at the connections compared to traditional electrical components, and as a result, SMC components are able to provide cleaner and more predictable TES waveform frequencies.

In another example, it would be conceivable to design the neuromodulation components in a custom application specific integrated circuit (ASIC) for delivering TES waveform sessions. Because an ASIC would be constructed for a specific task and not a variety of different actions, an ASIC-based neurostimulator circuit may require less energy and may be physically smaller and/or more compact. Requiring less energy to power the neuromodulation components means that smaller batteries and smaller inducers can be used in the device or that the neuromodulation device has a longer overall life. Moreover, with sufficient reductions in power storage capacity, some or all safety circuits may not be necessary to protect the user.

As mentioned earlier, the integration of the electrode elements and the neuromodulation elements of the neuromodulation device could eliminate the need for external software and firmware, and also the need for wireless capabilities. In that case, additional components may be needed to be placed on the neuromodulation device strip. This might include a power on/off switch, a means for selecting the waveform session desired, and/or a means for increasing or decreasing the intensity of stimulation (or another parameter of the stimulation waveform).

Figure 11B:
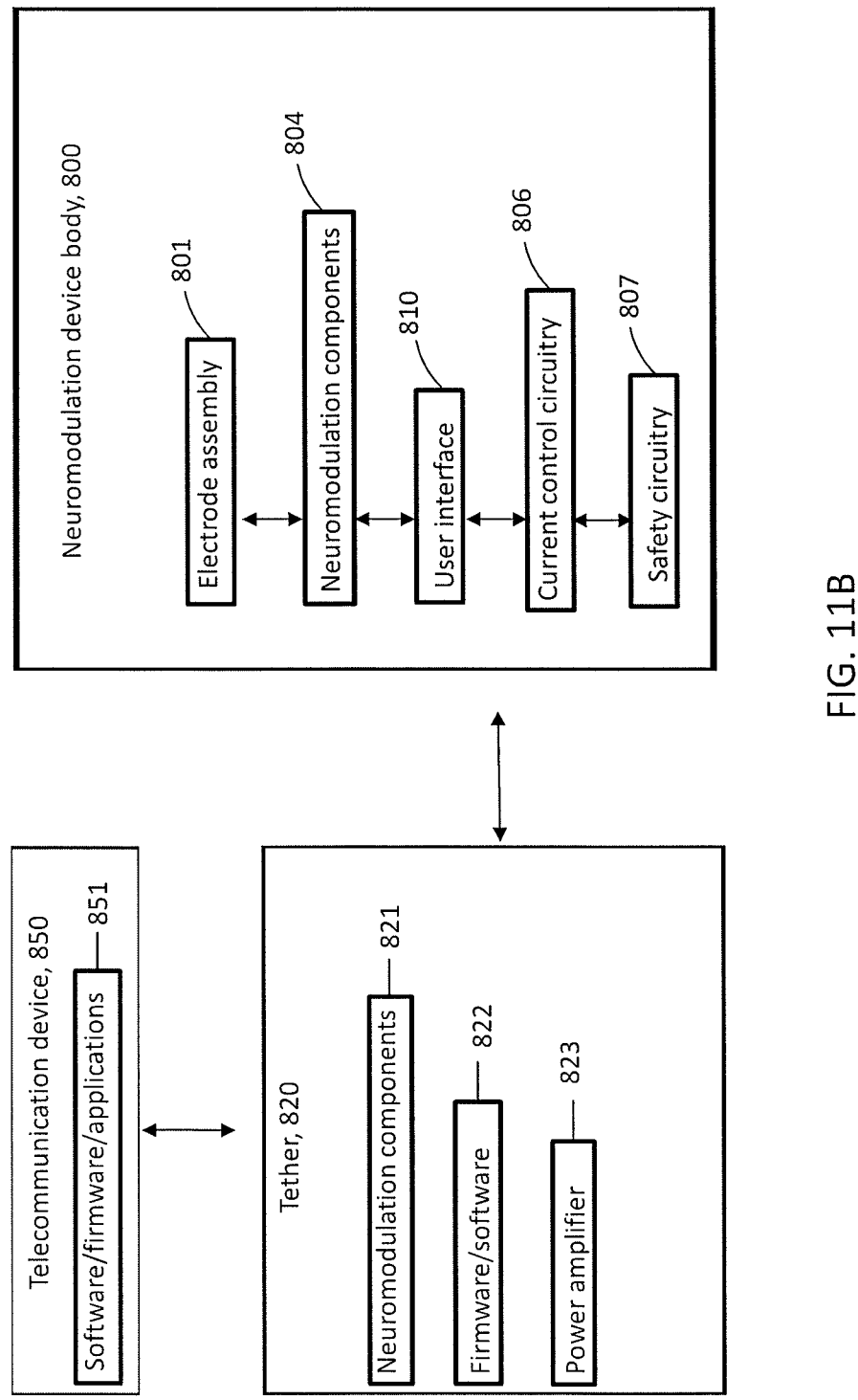
FIG. 11B is a diagram showing the configuration of an integrated neuromodulation device connected to a tether and a telecommunication device.

In a second embodiment of the present neuromodulation device as shown in FIG. 11B, a physical tether, such as a wire or cord, can be established between the neuromodulation device and a communication device (such as a smartphone, smartwatch, virtual reality headset, or a tablet). The tether 820 can contain some of the neuromodulation components 821 as well as firmware/software 822 for controlling the neuromodulation device body 800, and a power amplifier 823 (as part of current control circuitry) for boosting the power available to the neuromodulation device. In this embodiment, the neuromodulation device can also draw power from the communication device for outputting any particular waveform session. This can prove useful, because the primary power drain on the neuromodulation device will be the delivery of the stimuli from the first and second electrode to the subject's skin. Having a secondary source of power to draw from can decrease the size of the power supply used within the actual neuromodulation device. In one example of this second embodiment, the cord or wire used to connect the neuromodulation device to the control device can be a standard wire or cord. In a second example of the second embodiment, some components related to the neuromodulation aspect of the device (such as creating the waveforms, outputting the waveforms) can be placed external to the main neuromodulation device and retained within or hardwired to the cord or wire in a housing.

Figure 24:
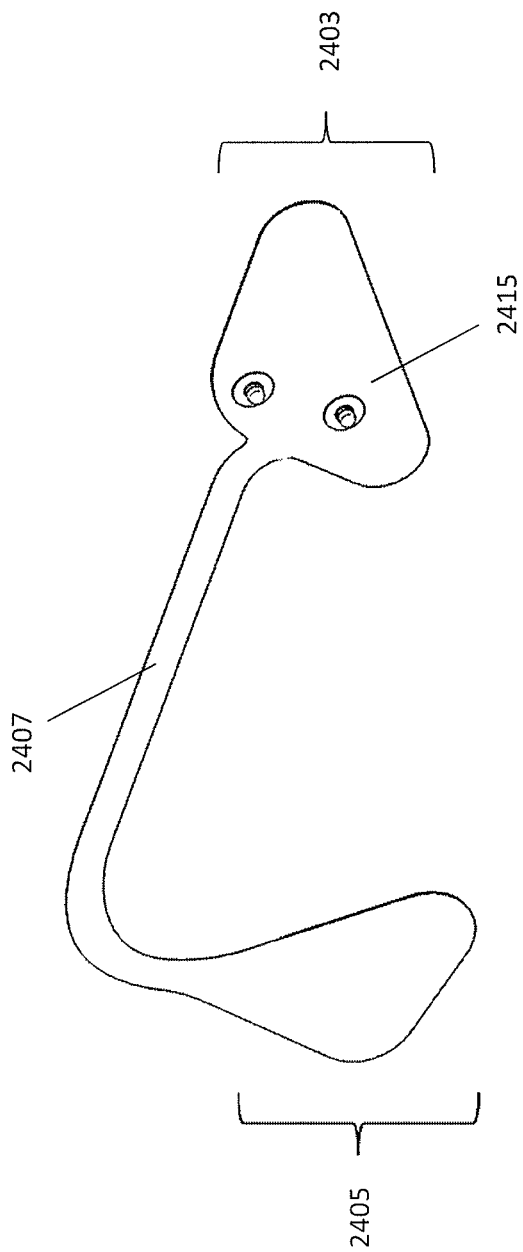
FIG. 24 shows a neuromodulation device with two external connectors for electrically contacting an external tether such as a cord or wire where the two external connectors are situated on the outer surface of the electrode region that contacts the user's head.
Figure 25:
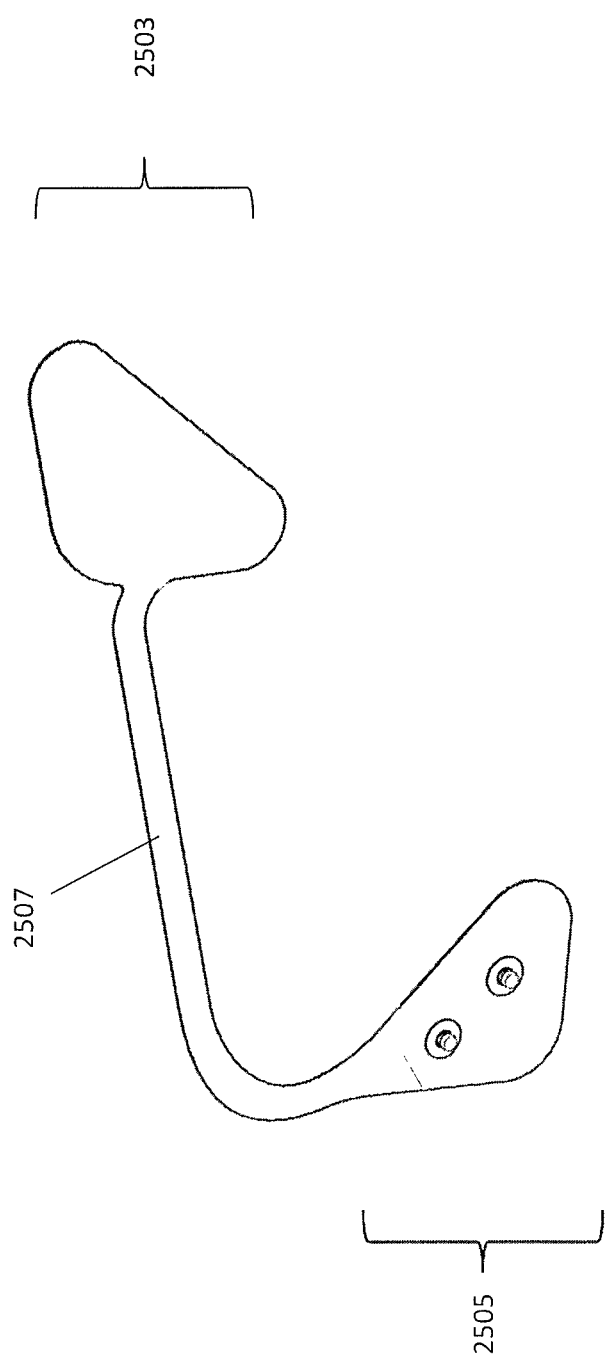
FIG. 25 shows a neuromodulation device with two external connectors for electrically contacting an external tether such as a cord or wire where the two external connectors are situated on the outer surface of the electrode region that contacts the user's neck.

In this second embodiment, the tether connecting the neuromodulation device to the communication device can be disconnected from both the neuromodulation device and the communication device. In order for the neuromodulation components that are external to the main neuromodulation device to communicate and work in concert with the internal neuromodulation components, the neuromodulation device, in this instance, will also include at least one connector port with which the wire or cord may connect to the neuromodulation device with as can be seen in FIG. 24. FIG. 24 shows a connector 2415 configuration on the electrode region of the neuromodulation body with two snaps, to which the tether can couple with. The tether can contain two separate connectors or two active regions of electrical contact within one integrated connector. Alternatively, the at least one connector for contacting the tether can be located on the electrode assembly that contacts the mastoid region as shown in FIG. 25.

Figure 20A:
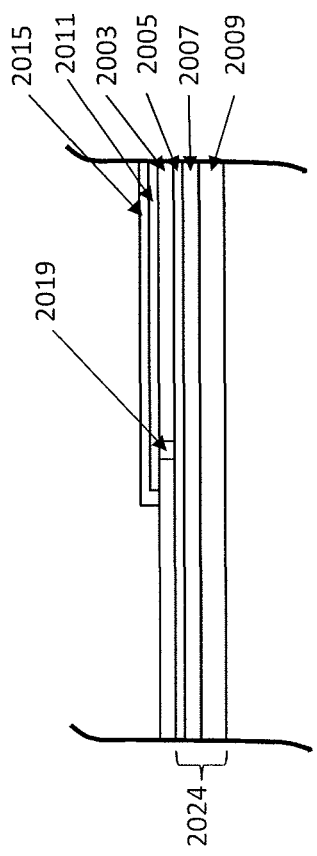
FIG. 20A shows an exemplary (not to scale) sectional view through an active region of an electrode fed by a conductive trace.
Figure 20C:
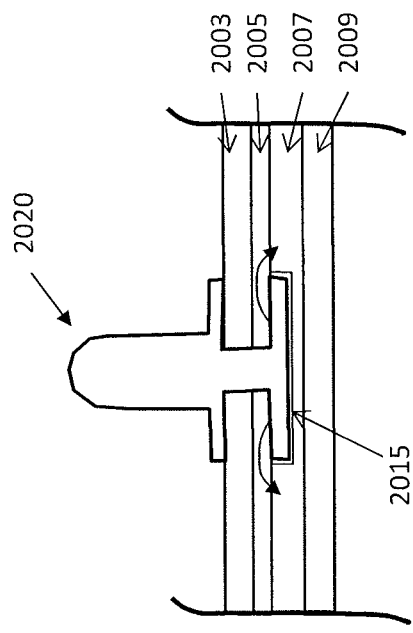
FIG. 20C is a slightly enlarged view of FIG. 20B.

There needs to be appropriate connections between the tether and the internal neuromodulation device components. FIGS. 20 and 21 show how a snap connector can be integrated into the body of the neuromodulation device. In FIG. 20A, an electrode trace 2011 extends on a top surface of a substrate 2003 (such as a polymeric material appropriate for use in a flexible circuit, e.g., Kapton). This trace 2011 may be insulated (e.g., by an insulating covering) 2015. An opening through the flex circuit (e.g., hole 2019) may include a conductive material (e.g., carbon black, silver, etc.) resulting in electrical communication between the trace 2011 and a portion of the electrically active region 2024, that (in this example) includes a layer of conductive metal (e.g., Ag) 2005, a layer of sacrificial conductor (e.g., Ag/AgCl) 2007 that completely covers the Ag layer and an outer, skin-contacting layer of hydrogel 2009 that is in electrical contact with the Ag/AgCl layer, and may also completely cover it (or cover it in conjunction with an insulator). The sacrificial Ag/AgCl layer 2007 in this example may also extend beyond the border of the conductive (i.e. Ag) layer 2005 to avoid shorts between the conductive (i.e. Ag) layer and the skin-contacting layer of hydrogel 2009 (i.e. extends beyond it around its entire circumference, including any internal exclusions or holes in the layer, for instance to permit a snap conductor to be placed).

In some variations, and in particular variations such as those shown in FIGS. 4A-4B, the flexible electrode strip may be configured so that the connectors (e.g., snaps, etc.) to couple to a cable or TES controller device are on the same surface as the electrodes, rather than being on the opposite (e.g., back or second) surface. Thus, all of the connectors and electrical contacts are on the same surface (the dermal facing, front or first surface). Thus connectors to connect to a tether, neurostimulator cable, etc. may be on the first surface of the electrode strip between the distal and proximal end, such as on the first end. This may simplify the manufacturing by having all the electrical traces on one side of the strip.

Figure 20B:
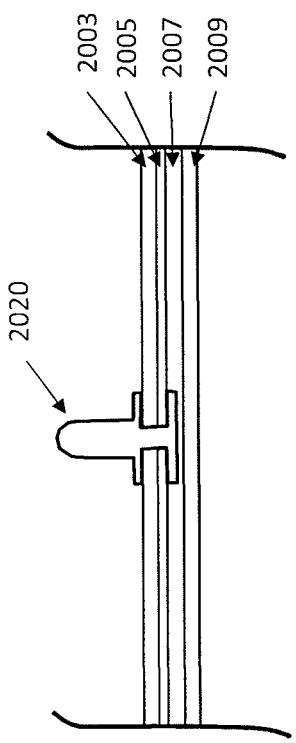
FIG. 20B shows a section view though an active region directly connected to a (snap) connector for coupling to a neurostimulator.
Figure 21:
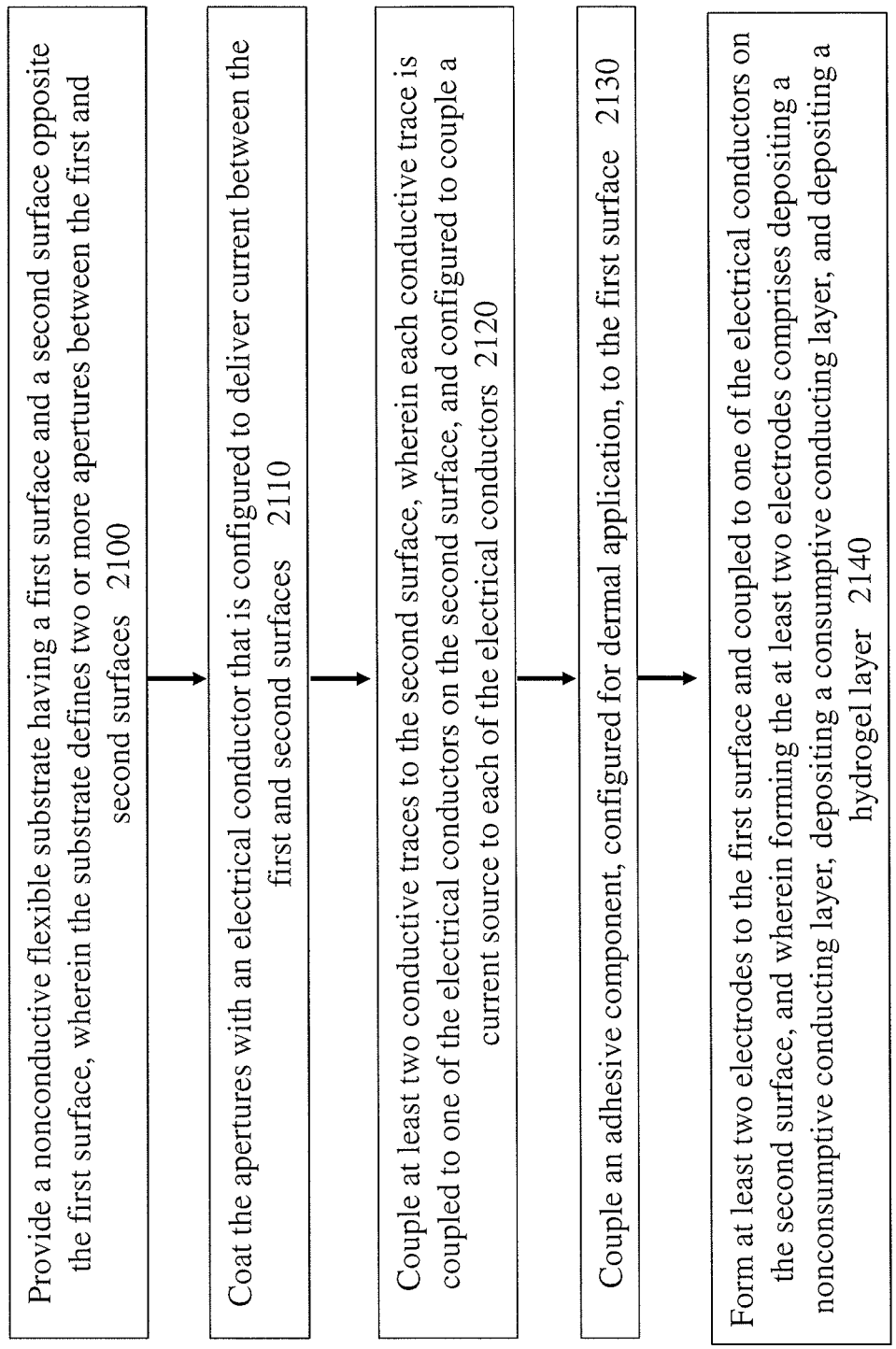
FIG. 21 schematically illustrates one method of forming an electrode apparatus such as a cantilever electrode apparatus.

FIG. 20B shows a partial section through a portion of an active region that is electrically connected to an electrical and/or mechanical connector via an indirect connection pathway and thereby connects to an electrical stimulator (e.g., such as a neurostimulator). This configuration is similar to that seen in the second active region 135 in FIG. 7D or 435 in FIG. 10C. In some variations the electrode includes an active region that is directly connected to the connector, such as the first active region 133 in FIG. 7D or the first active region 433 in FIG. 10C. An example of this arrangement is shown in FIG. 20B and in detail in FIG. 20C.

In FIG. 20B the active region of the electrode includes a contact (shown as a snap or pin) for connection to the electrical stimulator (e.g., neurostimulator). In this example, the connector 2020 penetrates the substrate 2003 and a layer of conductive material (shown as a conductive metal, e.g., Ag) 2005 and makes electrical contact with this Ag layer. The bottom of the post or connector 2020 is electrically insulated (visible in FIG. 20C as the insulating layer 2015). A sacrificial layer of Ag/AgCl covers the Ag layer (and the insulated base of the post 2020), and a skin contacting layer of conductive hydrogel 2009 contacts the Ag/AgCl layer. FIG. 20C shows a slightly enlarged view of FIG. 20B, and schematically illustrates the current flowing from the electrical/mechanical connector 2020 into the hydrogel 2009 through the sacrificial Ag/AgCl layer 2007 and the Ag conductive layer 2005. In this example, the connection is configured so that the current does not flow directly into the Ag/AgCl 2007 or hydrogel 2009, but first passes from an upper surface of the connector that is in electrical contact with the Ag layer 2005 and then down into the Ag/AgCl layer 2007 and the hydrogel to contact the user. Thus, in this example, the portion of the connector base in contact with the silver/silver chloride layer is insulated 2015 so that the current primarily passes through the silver layer 2005.

In general, an electrically active region of an electrode apparatus may include a nonconsumptive conducting layer (e.g., 2005 in FIGS. 20A-20C), a consumptive conducting layer (e.g., 2007 in FIGS. 20A-20C), and a conductive hydrogel layer (e.g., 2009 in FIGS. 20A-20C). In some embodiments, the consumptive layer may be a buffer layer disposed between the nonconsumptive layer and the hydrogel layer. Further, the consumptive layer may extend beyond the boundary of the nonconsumptive layer at each edge of the nonconsumptive layer and may be configured to reduce hydrolysis in the hydrogel layer, such that the consumptive layer donates electrons for redox reactions. Examples of the conductive nonconsumptive layers may include silver, gold, copper, or any other type of conductive metal or nonmetallic material, such as carbon or conductive polymers (e.g. poly(3,4-ethylenedioxythiophene). Preferably, the nonconsumptive and consumptive layers include silver. An important feature of the nonconsumptive layer is that any electrochemical reactions occurring in that layer do not cause the quality of the layer as an electrical conductor (i.e. impedance) to change during a transdermal (e.g., transcranial) stimulation. This feature ensures that current delivered to the layer is, for the most part, distributed evenly over its surface first before entering the consumptive layer. In some variations, an additional, higher impedance, layer is disposed between the nonconsumptive layer and the consumptive layer to more evenly spread current across the nonconsumptive layer before entering the higher impedance layer and, subsequently, the consumptive layer. In some embodiments, the nonconsumptive layer experiences reduced consumption, such that the nonconsumptive layer includes silver. Alternatively, the nonconsumptive layer may experience essentially zero consumption, such that the nonconsumptive layer includes carbon. In some embodiments, the nonconsumptive layer experiences reduced consumption since it does not include an anion that can be electrically consumed during electrical stimulation. The nonconsumptive layer may disperse the electrical current over its surface area before the current reaches the consumptive layer (i.e. there is lower impedance within the nonconsumptive layer than between the nonconsumptive layer and the consumptive layer). If the electrical current is not dispersed over the surface area of the nonconsumptive layer before reaching the consumptive layer, the consumptive layer may be overconsumed, such that AgCl becomes Ag(0) in a local area of the consumptive layer surface, causing uneven current distribution and the potential for local hydrolysis and local pH changes that may lead to discomfort in the subject. In embodiments, the consumptive layer is composed of a ratio of silver to silver chloride (Ag:AgCl) for efficient consumption and electrochemistry. Optimal ratios can be selected based on the charge balance of stimulation. In some embodiments, the ratio of Ag to AgCl particles in the consumptive layer may be between 40%:60% to 95%:5%, preferably 65%:35% to 85%:15%. Alternatively, the consumptive layer may include any suitable ratio of Ag:AgCl such that the chloride may be consumed but not depleted during an electrical stimulation session of sufficient length to induce a beneficial cognitive effect in a subject. The AgCl in the consumptive layer is consumed during alternating current or direct current stimulation (DC) because it acts as a sacrificial anode/cathode and is converted to Ag and a Cl− ion. The Ag+ in the consumptive layer is consumed during alternating current or direct current stimulation (DC) because it acts as a sacrificial anode/cathode and is converted to AgCl. In some embodiments, if the consumptive layer does not fully cover the dermal side of the nonconsumptive layer, the current may travel directly to the hydrogel layer and cause a site of high current density, for example a current hotspot. In some embodiments, the conductive hydrogel layer 37, as shown in FIG. 10i, ensures that the current is transmitted substantially evenly to the skin of a user. Further, the hydrogel layer creates a uniform connection between the multi-electrode assembly and the skin of a user.

Figure 20D:
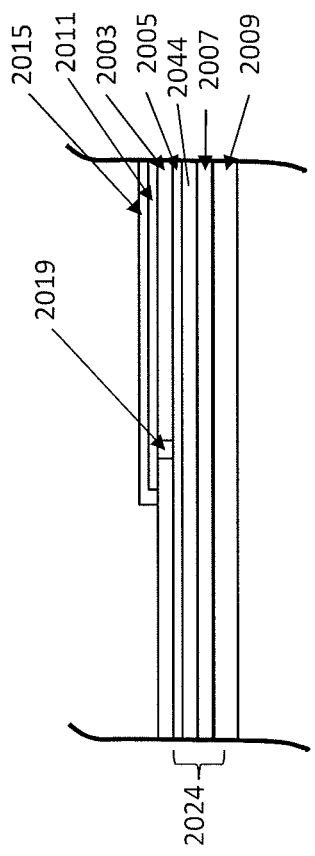
FIG. 20D illustrates another example (not to scale) of a section view though an active region of an electrode fed by a conductive trace; in this example, the active region includes a weakly insulating layer (e.g., a thin carbon layer between the silver and silver chloride layers).
Figure 20F:
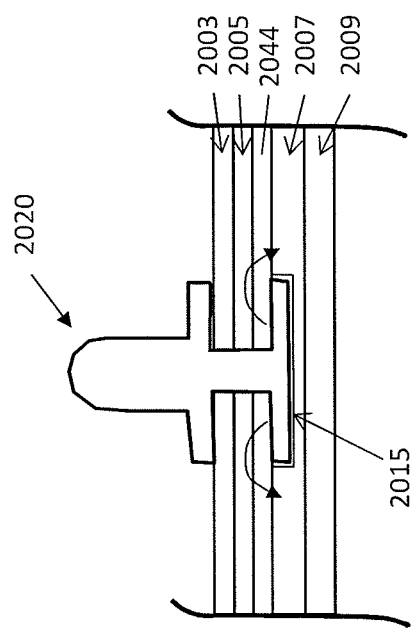
FIG. 20F is a slightly enlarged view of FIG. 20E.
Figure 20E:
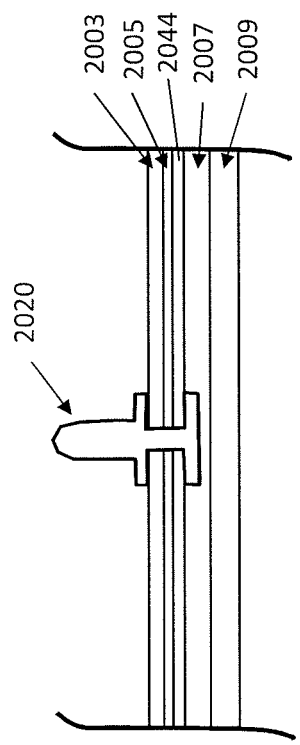
FIG. 20E shows a section view though an active region directly connected to a (snap) connector for coupling to a neurostimulator and including a weakly insulating layer (e.g., carbon).

In any of the electrode apparatuses described herein, an additional layer may be positioned between the conductive layer in electrical contact with the connector (e.g., snap connector) and the sacrificial anode/cathode layer in contact with the hydrogel. The additional layer may be a material that is less conductive than the adjacent conductive metal (e.g., Ag) layer and sacrificial (e.g., Ag/AgCl) layer, or even a weakly insulating material. In this example, the material is carbon, although other materials may be used. In general this layer may be less conductive than the layers immediately above (e.g., Ag) and below (e.g., Ag/AgCl). For example, FIGS. 20D-20F illustrate another variation of section through an active region of an electrode apparatus, showing different regions that may be used to form the active region and including an additional carbon layer. In FIG. 20D, the electrode trace 2011 extends on a top surface of a substrate 2003 (such as a polymeric material appropriate for use in a flexible circuit). This trace 2011 may be insulated (e.g., by an insulating layer 2015). An opening through the flex circuit (e.g., hole 2019) may include a conductive material (e.g., carbon black, silver, etc.) making an electrical communication between the trace 2011 and a portion of the electrically active region 2024, that includes a layer of conductive metal (e.g., Ag) 2005, a layer (e.g., carbon) having a lower conductance than the adjacent layers 2044, a covering layer of sacrificial Ag/AgCl 2007 that completely covers the Ag layer and it itself covered by the carbon layer 2044, and an outer, skin contacting layer of hydrogel 2009 in electrical contact with the Ag/AgCl layer.

The at least one connector port on the neuromodulation device can be either positioned on the proximal end electrode region, which corresponds to the temple area of the user or the distal end electrode region, which corresponds to the neck region of the user. The at least one connector port can make a "snap-on" type connection with the cord or wire. The snap-on connection here can be similar to the snap connectors in other designs where the neuromodulation unit "snapped on" and made connection with the proximal end electrode region. A person skilled in the art will also appreciate that other types of connectors can be used. The connection made between the neuromodulation device port and the cord or wire can electrically connect neuromodulation components outside of the neuromodulation device body to those neuromodulation components within the neuromodulation device, or also connect to the electrode elements contained within the neuromodulation device, or a combination thereof. Thus, to make the connection between the port and a viable region on the neuromodulation device, the connector or connectors need to be in electrical communication with the appropriate internal circuitry of the neuromodulation device.

For the neuromodulation assembly as a whole, a master control can be used to control the integrated neuromodulation components to communicate to the electrode assembly to deliver the desired waveform output and not dependent on the location of the various neuromodulation components relative to each other. The master control can include circuitry for controlling the current delivery, a battery, and other electronic circuitry for communicating with the electrode assembly and other electronic components present. In addition, because the neuromodulation device can function without the need for external controls, the neuromodulation components can be analog for outputting the waveform sessions. The use of purely analog signals simplifies the neuromodulation systems requirement compared to when digital signal are used.

In addition to the electrode assembly and the components controlling the neuromodulation, the incorporation of the neuromodulation components into the body of the device may necessitate some additional controls to allow the user to manipulate which waveform sessions to play. Additional controls can include a means for selecting the waveform sessions and a display for showing the user that the desired waveform session has been selected. Also, there may be an on/off switch for powering on and off the neuromodulation device. Examples for user interfaces include mechanical controls (i.e. toggles, switches, or knobs), touchscreen interfaces, and accelerometer-based controls (e.g. tap the device to cause a discrete movement event detected by a processor connected to an accelerometer). For example, any of the apparatuses described herein may include a touch-sensitive interface for controlling one or more aspects of the TES, such as the intensity, e.g., "swipe" up for higher intensity, "swipe" down for lower intensity, etc. Any of the apparatuses described herein may include an accelerometer to receive user input, such as taps or shakes, e.g., tap once to play/pause, tap twice to choose a different wave form, tap top of module for higher intensity, tap bottom of module for lower intensity, etc.

In use, any of the electrode apparatuses described herein may be connected to the user for neuromodulation. The neurostimulator may then electrically stimulate through the at least two electrodes, such that the neurostimulator delivers stimulation waveforms (or an ensemble of waveforms as discussed above) to the at least two electrodes for transdermal electrical stimulation and modification of the user's cognitive state. The method preferably functions to stimulate neural pathways, the brain, and/or nerves of a user using electrical stimulation delivered by a flexible electrode apparatus and neurostimulator.

Thus, neuromodulation using a multi-electrode assembly may include adhering a multi-electrode assembly to a body portion of a user to position a multi-electrode assembly on a body portion of a user such that the user may begin a transdermal or transcranial electrical stimulation protocol. In some embodiments, the system includes a single assembly containing two or more electrodes sized, configured, stimulated and positioned, as described herein, for achieving the desired neuromodulation effect. In some embodiments, the two or more electrodes within one assembly may include two or more electrode areas, such that the two or more electrode areas may be differentially stimulated to achieve different neuromodulation outcomes with one assembly, as described above. Alternatively, in some embodiments, the system comprises two or more assemblies, each containing at least one electrode for achieving the desired neuromodulation effect. The user may position the adhesive component on the first surface of the multi-electrode assembly, and press, stick, or otherwise secure the adhesive component to a body portion. In some embodiments, a user may remove a protective layer from the adhesive component before securing the adhesive component to a body portion of the user.

In some embodiments, the multi-electrode assembly may include sensors or other detectors that may detect a location or position of the multi-electrode assembly on the user. The multi-electrode assembly may begin delivering stimulation waveforms as soon as it is positioned in the correct location or position. Alternatively, the multi-electrode assembly may prevent a user from positioning the multi-electrode assembly in an inappropriate or incorrect location, such that the multi-electrode assembly may not deliver stimulation waveforms until it is repositioned or relocated.

Neuromodulation using a multi-electrode assembly may include coupling a controller to the at least two electrodes of the multi-electrode assembly through one or more connectors. The neurostimulator may be coupled to the multi-electrode assembly through a coupling element that couples the neurostimulator to the connectors on the electrode apparatus, as described above. Alternatively, the neurostimulator may be embedded in the flexible substrate (i.e. circuit components such as resistors, capacitors, current sources, microcontroller, switches, etc.) and electrically coupled to the electrodes in the electrode apparatus, such that all components are self-contained in the flexible substrate.

Neuromodulation using an electrode assembly may include electrically stimulating the at least two electrodes with the neurostimulator, such that the neurostimulator delivers stimulation waveforms to the at least two electrodes for transdermal/transcranial electrical stimulation. This may deliver stimulation waveforms to the electrode apparatus from the neurostimulator. Stimulation waveforms may include one or more waveforms selected from the group including: constant direct current; pulsed direct current stimulation (also referred to as pulsed monophasic alternating current stimulation); pulsed direct current stimulation with a constant direct current offset; alternating current stimulation (also referred to as biphasic alternating current stimulation); pulsed biphasic stimulation; or combined direct current stimulation and alternating current stimulation (also referred to as biased alternating current stimulation).

In some variations, any waveform described above can be combined in series or in parallel (i.e. concurrently) to create a hybrid waveform, or ensemble waveform. In embodiments, any waveform described above can be added, subtracted, convolved, or otherwise amplitude modulated. Moreover, in embodiments, any waveform above can have its amplitude ramped using linear, exponential, or another ramp shape including by one or more controllers that the user may manually adjust during stimulation.

The stimulation waveforms may include constant direct current stimulation above 3 mA maximum intensity. Alternatively, a constant direct current stimulation may be of any suitable maximum intensity such that a cognitive effect is induced. The stimulation waveforms may include a pulsed direct current stimulation above 5 mA (e.g., above 7 mA, etc.). Alternatively, a pulsed biphasic stimulation may be of any suitable magnitude such that a cognitive effect is induced. The stimulation waveforms may include an alternating current stimulation above 2 mA maximum intensity. Alternatively, an alternating current stimulation may be of any suitable maximum intensity such that a cognitive effect is induced. The stimulation waveforms may include a biased alternating current stimulation with a direct current offset less than 1.5 mA and maximum alternating current amplitude above 3 mA. Alternatively, the direct current offset and the maximum alternating current amplitude may be of any suitable magnitude such that a cognitive effect is induced. The values of the direct current offset and the maximum alternating current amplitude for the biased alternating current stimulation may be in any combination to achieve the desired stimulation waveform.

In some embodiments, using alternating current stimulation or pulsed direct current stimulation, pulses can comprise square waves, sine waves, sawtooth waves, triangular waves, rectified (unimodal) waves, pulse-width modulated, amplitude-modulated, frequency-modulated, or other pattern of alternating current waveform. For preferred embodiments using alternating current stimulation or pulsed biphasic or unimodal stimulation, a primary frequency of stimulation is between 0.5 Hz and 1 MHz; optionally between 650 Hz and 50 kHz; optionally between 650 Hz and 20 kHz; and optionally between 750 Hz and 20 kHz. Alternatively, the primary frequency stimulation may be in any suitable range such that a cognitive effect is induced.

In some embodiments, for pulsed biphasic stimulation and alternating current stimulation, the maximum intensity delivered to a subject transcranially is generally greater than 3.0 mA; optionally greater than 3.5 mA; optionally greater than 4 mA; optionally greater than 5 mA; optionally greater than 7.5 mA; optionally greater than 10 mA; optionally greater than 15 mA; and optionally greater than 20 mA. Alternatively, the maximum intensity may be of any suitable maximum intensity such that a cognitive effect is induced. In preferred embodiments using pulsed direct current stimulation and/or alternating current stimulation, efficacious peak current intensities are generally between about 3 mA and about 25 mA.

In some embodiments, for constant direct current stimulation, the maximum intensity delivered to a subject transcranially is greater than 3.0 mA; optionally greater than 3.5 mA; optionally greater than 4 mA; optionally greater than 5 mA; optionally greater than 7.5 mA; and optionally greater than 10 mA. Alternatively, the maximum intensity may be of any suitable maximum intensity such that a cognitive effect is induced.

In use, a user may interact with a controller (e.g., a smartphone controlled by application software/firmware) that pairs with the neurostimulator (e.g. by Bluetooth). The user may operate the controller to select the operational mode, e.g., the type of cognitive effect to be induced, such as an energy mode or calm mode, and/or the device could automatically detect based on the configuration of an electrode to which the apparatus is attached. The user may select, for example, from a set of ensemble waveforms which ensemble waveform to execute. There may be separate waveforms to evoke a desired experience/effect (e.g., "calm" or "energy" ensemble waveforms). An ensemble waveform may generally be between about 3-90 min (e.g., between about 3-60 min, between about 5-60 min, between about 5-40 min, etc., between about 3-25 minutes, etc.) long, or longer (e.g., greater than 3 min, greater than 5 min, greater than 10 min, greater than 12 min, etc.). In general, an ensemble waveform may be broken up into segments with specific pulsing parameters, i.e. current amplitude, frequency, duty cycle, charge imbalance, shorting/capacitive discharge, etc., and these parameters may change at pre-specified times as they change to new segments; a transition period may be included to switch between block properties. Once the user selects an ensemble waveform, they can start the neurostimulation and the user can control or change the perceived intensity (e.g., by dialing the perceived intensity up or down), pause, or stop the session using the phone (app). In general, the perceived intensity can be scaled by the user between 0-100% of a target perceived intensity (e.g., a target current, frequency, duty cycle, charge imbalance, and/or shorting/capacitive discharge), using a control such as one or more buttons, sliders, dials, toggles, etc., that may be present on the controller (e.g., smartphone) in communication with the neurostimulator. The controller may also allow a user to activate ("on demand") a waveform configuration that is designed to evoke a predetermined response. For example, the control device could be adapted to display one or more icons to trigger phosphenes or an intensification of the perceived cognitive effect of skin sensation intensity. In addition, the controller may be configured to allow the user to press an icon to help in applying the electrode apparatus and/or neurostimulator. For example, activating this control may cause the smartphone to activate a front-facing camera on the phone to help the user to attach the apparatus to the head. During or after a session, a user can access help screens, a profile page, social sharing interfaces (i.e. tweet your experience), feedback about a session, and analysis and history of previous use. In general, the system may also be configured to pass data to and from the controller and/or the neurostimulator and to/from a remote server via the Internet. These data may include user information, waveform data, information about the function or state of the hardware device or electrode assembly, etc.

In addition, the integrated neurostimulator and electrode apparatus may fit under the temple portion of an eyeglass frame for users wearing glasses; thus the portion of the combined assembly should ideally be thin enough to fit between glasses and the temple region. However, it may also be beneficial to have some portions of the system be sufficiently thick to allow the apparatus to contain a sufficient battery (or other power portion) so that the unit can be used for a reasonable amount of time between charges (e.g. at least 20 minutes of electrical stimulation, at least 30 minutes of electrical stimulation, at least 40 minutes of electrical stimulation, at least 50 minutes of electrical stimulation, at least 60 minutes of electrical stimulation, at least 120 minutes of electrical stimulation, etc.). Thus one portion of the apparatus may be thick enough to allow a standard battery and/or circuitry at one end region (e.g., an end that is worn higher up on the face).

In general, a user may wear a neuromodulation device and apply one or more waveforms (e.g., waveform ensembles) using the neuromodulation device to induce a cognitive effect. The apparatuses described herein may be configured to provide one or more cognitive effects. In general, a cognitive effect may include any induced cognitive effect that is perceived subjectively by the recipient as a sensory perception, movement, concept, instruction, other symbolic communication, or modifies the recipient's cognitive, emotional, physiological, attentional, or other cognitive state. For example, an effect of electrical stimulation is one or more of inhibition, excitation, or modulation of neuronal activity. Specific examples of cognitive effects may include relaxation, enhanced attention, mood elevation, increased energy (e.g., physiological arousal, increased subjective feelings of energy), or the like. Cognitive effects may be stereotypical across a population (though with individual variation and degree) and may be demonstrated by any appropriate means, including by subject reporting, objective testing, imaging, physiological recording, etc. Particular cognitive effects evoked may depend upon the position of the electrodes of the apparatus with respect to the subject, and/or the stimulation parameters described herein. The apparatuses described herein may be optimized to achieve a specific cognitive effect.

A cognitive effect of neuromodulation may cause a change in a user's level of energy, fatigue, sleepiness, alertness, wakefulness, anxiety, stress, sensory experience, motor performance, formation of ideas and thoughts, sexual arousal, creativity, relaxation, empathy, and/or connectedness that is detectable by an objective measurement (e.g. behavioral assay) and/or subjective report by the user.

For example, a cognitive effect of neuromodulation may cause a change in an emotional state of the user where the change is detectable by an objective measurement (e.g. behavioral assay) and/or subjective report by the user and an emotion affected is selected from the list including but not limited to: affection, anger, angst, anguish, annoyance, anxiety, apathy, arousal, awe, boredom, confidence, contempt, contentment, courage, curiosity, depression, desire, despair, disappointment, disgust, distrust, dread, ecstasy, embarrassment, envy, euphoria, excitement, fear, frustration, gratitude, grief, guilt, happiness, hatred, hope, horror, hostility, hurt, hysteria, indifference, interest, jealousy, joy, loathing, loneliness, love, lust, outrage, panic, passion, pity, pleasure, pride, rage, regret, relief, remorse, sadness, satisfaction, self-confidence, shame, shock, shyness, sorrow, suffering, surprise, terror, trust, wonder, worry, zeal, and zest.

In some variations, the cognitive effects evoked by the apparatuses described herein may be positive cognitive effects; positive cognitive effects may refer to cognitive effects resulting in an increase in alertness, an increase in relaxation, a decrease in fatigue, and a decrease in anxiety, an enhancement in motor performance, an increase in recall, and an increase in empathy.

A cognitive effect of neuromodulation may cause a change in brain activity measured by one or a plurality of: electroencephalography (EEG), magnetoencephalography (MEG), functional magnetic resonance imaging (fMRI), functional near-infrared spectroscopy (fNIRS), positron emission tomography (PET), single-photon emission computed tomography (SPECT), computed tomography (CT), functional tissue pulsatility imaging (fTPI), xenon 133 imaging, or other techniques for measuring brain activity known to one skilled in the art.

A cognitive effect of neuromodulation may be detectable by a physiological measurement of a subject, including but not limited to measurements of the following: brain activity, body temperature, electromyogram (EMG), galvanic skin conductance (GSC), heart rate, blood pressure, respiration rate, pulse oximetry, pupil dilation, eye movement, gaze direction, measurement of circulating hormone (e.g. cortisol or testosterone), protein (e.g. amylase), or gene transcript (i.e., mRNA); functional infrared thermography (e.g. of facial temperature); and other physiological measurement. A cognitive effect of neuromodulation may be detectable by a cognitive assessment that takes the form of one or more of: a test of motor control, a test of cognitive state, a test of cognitive ability, a sensory processing task, an event related potential assessment, a reaction time task, a motor coordination task, a language assessment, a test of attention, a test of emotional state, a behavioral assessment, an assessment of emotional state, an assessment of obsessive compulsive behavior, a test of social behavior, an assessment of risk-taking behavior, an assessment of addictive behavior, a standardized cognitive task, an assessment of "cognitive flexibility" such as the Stroop task, a working memory task (such as the n-back task), tests that measure learning rate, or a customized cognitive task.

In general, subjects treated with TES with appropriate electrode configurations (positions) and TES waveforms (waveform ensembles) may experience neuromodulation with cognitive effects including, but not limited to: enhanced focus and attention; enhanced alertness; increased focus and/or attention; enhanced wakefulness; increased subjective feeling of energy; increased objective (i.e. physiological) energy levels; higher levels of motivation (e.g. to work, exercise, complete chores, etc.); increased energy (e.g., physiological arousal, increased subjective feelings of energy); and a physical sensation of warmth in the chest.

In general, subjects treated with TES with appropriate electrode configurations (positions) and TES waveforms experience neuromodulation with cognitive effects including, but not limited to: a state of calm, including states of calm that can be rapidly induced (i.e. within about 5 minutes of starting a TES session); a care-free state of mind; a mental state free of worry; induction of sleep; a slowing of the passage of time; enhanced physiological, emotional, or and/or muscular relaxation; enhanced concentration; inhibition of distractions; increased cognitive and/or sensory clarity; a dissociated state; a state akin to mild intoxication by a psychoactive compound (i.e. alcohol); a state akin to mild euphoria induced by a psychoactive compound (i.e. a morphine); the induction of a state of mind described as relaxed and pleasurable; enhanced enjoyment of auditory and visual experiences (i.e. multimedia); reduced physiological arousal; increased capacity to handle emotional or other stressors; a reduction in psychophysiological arousal as associated with changes in the activity of the hypothalamic-pituitary-adrenal axis (HPA axis) generally associated with a reduction in biomarkers of stress, anxiety, and mental dysfunction; anxiolysis; a state of high mental clarity; enhanced physical performance; promotion of resilience to the deleterious consequences of stress; a physical sensation of relaxation in the periphery (i.e. arms and/or legs); and a physical sensation of being able to hear your heart beating.

Figure 17:
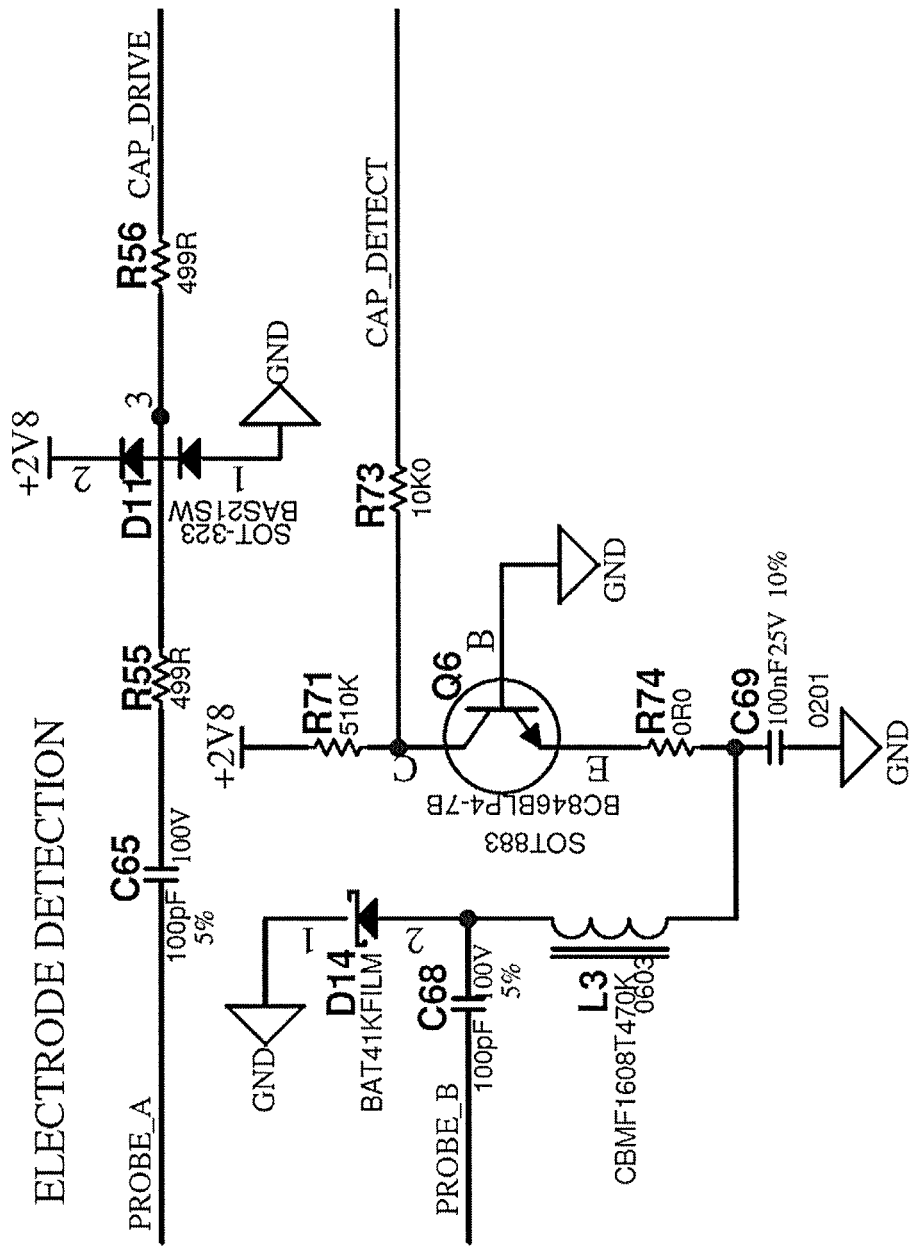
FIG. 17 is one example of a detection circuit that may be used to detect connection and or the type or identity of an electrode apparatus; the detection circuit may be included on a neurostimulator (e.g. cable neurostimulator) to detect some variations of the electrode apparatuses described herein.

Any of the apparatuses described herein may include a detection circuit to detect a connection between the strip electrode (including an electrode with integrated TES circuitry) an other apparatus, such as a TES cable neurostimulator. The detection circuit may be included on a neurostimulator (e.g. cable neurostimulator) to detect some variations of the electrode apparatuses described herein. FIG. 17 illustrates one example of such a circuit.

Instead of or in addition to the detection capacitor described above, any of the variations described herein may also include one or more sensors. These sensors may be read by the neurostimulator, which may analyze, store, and/or transmit the sensed information to the controller and/or a third party platform. For example, any of the electrode apparatuses described herein may include one or more sensors that may provide information useful to determine when the electrode apparatus has degraded, and/or requires replacement, refurbishing, or removal. Although in many of the examples provided herein the electrode apparatus is configured to be single use, and disposable, in any of the examples described herein the electrode apparatus may be durable or multi-use.

For example, the apparatuses (including devices and systems) and methods described herein may be configured to determine when (or if) the electrode apparatus for TES neuromodulation has degraded and requires replacement, refurbishing, or removal. Using only electrode apparatuses that meet quality criteria is beneficial so that TES neuromodulation is comfortable for a subject and reliably induces a desired cognitive effect.

For example, a TES apparatus may incorporate an electrode apparatus or a set of electrode apparatuses. Disposability and replaceability may be important features for components of the system that contain electrodes, because electrodes typically degrade in important ways that affect comfort, efficacy, and usability.

As used herein, a disposable element may refer to a limited-use item (e.g., single-use or limited multiple-use, including 2-3 uses, 2-5 uses, 2-7 uses, 2-10 uses, or less than 5 uses, less than 10 uses, etc.). A disposable element may be used once (or 2-3 times, etc.) and then removed from the apparatus and replaced with a new element. In particular, the electrode apparatuses described herein may be disposable elements that include a conductive material (e.g., conductive gel, conductive adhesive, etc.) and/or adhesive that is only reliably useful a limited number of times before needing to be replaced or refurbished.

Beneficial features of transdermal electrodes that degrade over time and over use include adherence, pH buffering, and uniform distribution of current across the face of the electrode. In general, an electrode apparatus may define use cases for which properties (e.g., adhesion, pH buffering, uniform distribution of charge) are within acceptable ranges. Methods for determining when an electrode apparatus requires replacement or refurbishing may use one or more product specification, compare that value to one expected after a detected amount and type of electrode apparatus use, determine whether or not the electrode apparatus quality is outside a specified range, and then either inform a user that the electrode apparatus requires replacement or refurbishment or automatically stop a neurostimulation (or lock out the neurostimulator so that a waveform ensemble cannot be started).

Adherence is a first beneficial property of electrode apparatuses that degrades over time. In general, apparatuses and methods for maintaining adhesive properties over time and use may include a way to determine or estimate when the adhesive properties of an electrode apparatus have degraded such that the electrode requires replacement or refurbishment. The quality of an adherent active region of the electrode apparatus may be reduced each cycle of adherence to a subject and removal from the subject. For instance, a hydrocolloid adhesive component of an electrode apparatus on the dermal-facing portion of a disposable electrode apparatus may degrade when it is used or if it gets wet (e.g. due to rain, sweat, or a liquid spill). An adherent electrode apparatus will also generally require a storage device such as wax paper or plastic between uses to protect the adhesive for subsequent adherences of the unit on the subject's skin. The act of placing an adherent electrode apparatus onto a protective covering (or equivalently placing a protective covering on the electrode) may also somewhat degrade the adhesive properties of the electrode apparatus despite the composition of the covering being selected so as to minimally affect the adhesive. Transdermal electrode components of the system that become less adherent are less than ideal for any number of reasons, including that an electrode apparatus may partially or completely separate from a user's skin (e.g. fall off); or the impedance of electrical connection between an active region and a user's skin may increase because the physical connection is not uniform across the electrically conductive portion of the electrode apparatus.

Adhesive materials of an adhesive electrode apparatus may include a portion of the active region intended for delivering electrical stimulation (i.e. adhesive and conductive) and/or a portion of the electrode apparatus that is not intended for delivering electrical stimulation that is configured to cause an active region/portion of the electrode to be in close physical contact (i.e., low impedance) contact with a user's skin.

Buffering pH is a second beneficial property of electrode apparatuses that degrades over time. Causing current to be distributed evenly across the transdermal face of an electrode is a third beneficial property of electrode apparatuses that degrades over time. Uniform current distribution and pH buffering can be improved by features of electrode apparatuses, including the water composition of a hydrogel component of an electrode apparatus for TES and the amount of Ag and Ag/AgCl contained in a component that couples an electric current through the active region to the skin. Water in a hydrogel component of an electrode apparatus (or other water-containing conductive material) is consumed as net charge is transferred into a subject's body. Ag/AgCl components of an electrode (including components coated with Ag/AgCl and Ag/AgCl ink) improve the efficiency of charge transfer to tissue (essentially a salt solution) and are also consumed during electrical stimulation.

Charge imbalanced TES waveforms are often necessary for inducing cognitive effects, but these waveforms can consume Ag, Ag/AgCl, and water, causing the degradation of transdermal electrodes and limiting their effective use.

If too much water in an active region is consumed, the efficiency of redox reactions is reduced leading to pH changes that may cause skin irritation, pain, and/or tissue damage. Thus, in some variations a pH sensor may be sufficiently sensitive such that a user (or the neurostimulator and/or controller, for automated systems) can stop or turn down the net charge of stimulation or replace an electrode apparatus before irritation, pain, or tissue damage occurs. A pH-sensitive material may be incorporated in a visible portion of an electrode apparatus so that a user (or third party) can determine if pH changes are occurring. Alternatively, a pH sensor may be configured to detect pH changes and transmit this information to a visible part of an electrode apparatus, to a durable portion of a neurostimulator/controller, or to a computing device connected to a durable portion of a neurostimulator/controller in a wired or wireless fashion.

A TES system can automatically or by user input keep track of parameters of use that affect electrode quality, including but not limited to: number of adherence and removal cycles from the skin; number of TES sessions; duration of stimulation; cumulative net charge delivered; cumulative absolute charge delivered; peak current delivered; and the like. A Coulomb counter may be included in the electronic circuitry of a neurostimulator system to determine the amount of charge transferred to a subject during a stimulation session.

In some variations, a sensor contained in an electrode apparatus can be used to determine when the electrode apparatus has been placed on a user. This may be advantageous, because it does not require a self-report by a user each time an electrode apparatus is adhered or removed from the skin. Effective sensors for determining whether an electrode apparatus has been adhered to or removed from a subject's skin include, but are not limited to: an accelerometer, a capacitive sensor, an EMG sensor, an optical sensor (e.g. a light-emitting diode or other light source and a diode, CMOS, or other detector to measure reflectivity), a microphone, or another sensor effective for determining whether an electrode apparatus is adhered to or removed from a user's skin. For example, one or more accelerometers may be contained within an electrode assembly; in a durable assembly coupled to the electrode apparatus; or both.

In general, an appropriate signal processing and algorithm workflow may be applied to data from the one or more sensors in the above list to determine whether an electrode apparatus has been adhered to or removed from a user. Determining whether an electrode apparatus has been placed (adhered) onto a subject's body (generally, a subject's skin) may be achieved by a non-transitory computer-readable storage medium storing a set of instructions capable of being executed by a remote processor (including a smartphone, smartwatch, tablet computer, or the like), that when executed by the computing device containing the remote processor causes sampling of at least one sensor (e.g. a single-axis or multi-axis accelerometer) over time, and applies appropriate signal processing and signal detection algorithms to identify when an electrode is adhered to a subject or removed from a subject.

For example, with an accelerometer sensor, adherence of an electrode apparatus to a subject could be determined or estimated based on a sequence of accelerometer signals corresponding to a subject holding the electrode apparatus in their hand; followed by the user slowly placing the electrode apparatus onto his/her skin; followed by a period of time when accelerometer signals that are consistent with the biomechanics of the part of the body to which the electrode was adhered are detected (which can be known by the type of electrode apparatus and thus appropriate body positioning thereof; or by other means such as an image taken by a smartphone camera). One skilled in the art of wearable sensors and signal processing will recognize that signals from each of the sensors listed above can be used to define an algorithm that determines electrode-dermal connections with an appropriate reliability and sensitivity.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A neuromodulation apparatus for delivering transdermal electrical stimulation (TES) to a wearer, the apparatus comprising:
   a flat and flexible substrate having a first end, wherein the first end comprises a first end top surface and a first end bottom surface, and a second end, wherein the second end comprises a second end top surface and a second end bottom surface;
   a first electrode portion at the first end, a first electrode active region disposed on the first end bottom surface;
   a second electrode portion comprising a second electrode active region disposed on the second end, wherein the first electrode active region and the second electrode active region are configured to deliver energy to the wearer's skin;
   a flexible elongated substrate region separating the first end and the second end by a path length of at least two inches, the flexible elongated substrate region configured to take on a flat configuration that defines a plane, wherein the flexible elongated substrate region is flexible out of the plane and rigid in the plane, wherein the flexible elongated substrate region includes a bend within the plane; and
   an assembly of neuromodulation components integrated onto the first end, or the second end, or the flexible elongated substrate region, or a combination thereof, configured to control the first electrode portion and the second electrode portion to deliver at least one preprogrammed TES waveform to the wearer's skin at the first electrode active region and at the second electrode active region, the assembly including a near-field communication circuit and a near-field communication selector adhered to or near the near-field communication circuit, wherein the near-field communication selector encodes one or more ensemble waveforms for delivery to the wearer.

2. The apparatus of claim 1, wherein the assembly of neuromodulation components comprises a waveform generator.

3. The apparatus of claim 1, further comprising a power source.

4. The apparatus of claim 1, further comprising at least one of: a controller, a memory, a skin-impedance sensing circuit, and a timer.

5. The apparatus of claim 1, further comprising an adhesive on the first end bottom surface for securing the apparatus to the wearer's skin.

6. The apparatus of claim 1, wherein the first electrode portion is configured to fit against a temple region of the wearer.

7. The apparatus of claim 1, wherein the first electrode active region extends from a first edge of the first electrode portion, across a lower surface of the first electrode portion, to a second edge of the first electrode portion.

8. The apparatus of claim 1, wherein the flexible elongated substrate region comprises a wire.

9. The apparatus of claim 1, wherein the flexible elongated substrate region comprises a planar region that is flexible in a first direction but not flexible in a direction normal to the first direction.

10. The apparatus of claim 1, wherein the assembly of neuromodulation components comprises surface mounted components, custom application specific integrated circuits, micro-electronic mechanical devices, or a combination thereof.

11. The apparatus of claim 1, further comprising at least one of: an on/off switch, a control for selecting a waveform, and a display for showing the wearer a particular waveform selected.

12. The apparatus of claim 1, further comprising a cord configured to connect the assembly of neuromodulation components to a handheld computing device.

13. The apparatus of claim 12, wherein the cord is configured to connect the assembly of neuromodulation components to the handheld computing device comprising a smartphone.

14. The apparatus of claim 1, wherein the flexible elongated substrate region doubles back at the bend when in the flat configuration.

15. The apparatus of claim 1, wherein the flexible elongated substrate includes an electrical path defined by the path length, wherein the electrical path doubles back at the bend when the flexible elongated substrate region is in the flat configuration.

16. The apparatus of claim 1, wherein the near-field communication selector includes a coil and circuitry encoding control information for the one or more ensemble waveforms.

17. The apparatus of claim 1, wherein the one or more ensemble waveforms includes sequences of different component waveforms having one or more: different peak current amplitudes, different frequencies, different percent duty cycles, different percent charge imbalances, different capacitive discharge periods, different bursting frequency, and different bursting duty cycles.

18. The apparatus of claim 1, wherein the one or more ensemble waveforms includes added, subtracted, convolved, or amplitude modulated waveforms.

19. The apparatus of claim 1, wherein the one or more ensemble waveforms includes segments with different pulsing parameters.

20. The apparatus of claim 1, wherein the near-field communication selector is a sticker or stamp.

21. A system for delivering transdermal electrical stimulation (TES) to a subject's head or head and neck, the system comprising:
   a substrate having a first end and a second end, the first end comprising a top surface and a bottom surface;

a first electrode portion disposed on the first end;

a first electrode active region disposed on the bottom surface of the first end;

wherein the second end comprises a top surface and a bottom surface:

a second electrode portion, comprising a second electrode active region, disposed on the second end;

wherein the first electrode active region and the second electrode active region are configured to deliver energy to the subject's skin;

a flexible elongated member separating the first end and the second end by a path length of at least two inches, the flexible elongated member configured to take on a flat configuration that defines a plane, wherein the flexible elongated member is flexible out of the plane and rigid in the plane, the flexible elongated member including a bend within the plane to accommodate wrapping of the flexible elongated member around at least a portion of the subject's head or head and neck;

a tether for connecting the substrate to a telecommunication device; and an assembly of neuromodulation components integrated into the first end, the second end, the flexible elongated member, the tether, or a combination thereof, the assembly of neuromodulation components configured to control the first electrode portion and the second electrode portion to deliver at least one pre-programmed waveform stimuli to the subject's skin at the first active electrode region and at the second active electrode region, the assembly including a near-field communication circuit and a near-field communication selector adhered to or near the near-field communication circuit, wherein the near-field communication selector is configured to unlock one or more ensemble waveforms for delivery to the subject.

22. The system of claim 21, further comprising the telecommunication device configured to control the at least one pre-programmed waveform stimuli to be outputted by the first electrode active region and the second electrode active region.

23. The system of claim 22, wherein the telecommunication device comprises an application for controlling the at least one pre-programmed waveform stimuli to be outputted.

24. The system of claim 22, wherein the tether comprises a first end for connecting to a neuromodulation device and a second end for connecting to the telecommunication device.

25. The system of claim 21, wherein the tether is a cord or a wire.

26. The system of claim 21, wherein the tether comprises an amplifier for boosting the at least one pre-programmed waveform stimuli to be outputted.

27. The system of claim 21, wherein the tether comprises electronic circuitry for controlling the at least one pre-programmed waveform stimuli.

28. The system of claim 21, wherein the first end further comprises at least one connector for connecting to the tether.

29. The system of claim 21, wherein the second end further comprises at least one connector for connecting to the tether.

30. The system of claim 21, further comprising an adhesive on the bottom surface of the first end and an adhesive on the second electrode portion for securing the substrate to the subject's skin.

31. The system of claim 21, wherein the first electrode portion is of a shape and a size that can fit in a wearer's temple region.

32. The system of claim 21, wherein the first electrode active region extends from a first edge of the first electrode portion, across the bottom surface of the first electrode portion, to a second edge of the first electrode portion.

33. The system of claim 21, wherein the flexible elongated member comprises a wire.

34. The system of claim 21, wherein the flexible elongated member comprises a planar substrate that is flexible in a first direction but not flexible in a direction normal to the first direction.

35. The system of claim 21, wherein the assembly of neuromodulation components comprises surface mounted components, custom application specific integrated circuits, micro-electronic mechanical devices, or a combination thereof.

36. The system of claim 21, further comprising one or more of an on/off switch, a control for selecting a particular waveform, and a display for showing the subject the particular waveform selected.

* * * * *